United States Patent
Lu et al.

(10) Patent No.: US 6,514,978 B2
(45) Date of Patent: Feb. 4, 2003

(54) THROMBORESISTANT MATERIALS INCORPORATING PYRAZINONE PROTEASE INHIBITORS

(75) Inventors: Tianbao Lu, Collegeville, PA (US); Bruce E. Tomczuk, Collegeville, PA (US); Thomas P. Markotan, Morgantown, PA (US)

(73) Assignee: 3-Dimensional Pharmaceuticals, Inc., Exton, PA (US)

( * ) Notice: Subject to any disclaimer, the term of this patent is extended or adjusted under 35 U.S.C. 154(b) by 0 days.

(21) Appl. No.: 09/773,730

(22) Filed: Feb. 2, 2001

(65) Prior Publication Data

US 2001/0021713 A1 Sep. 13, 2001

Related U.S. Application Data

(62) Division of application No. 09/330,128, filed on Jun. 11, 1999, now Pat. No. 6,204,263.
(60) Provisional application No. 60/088,989, filed on Jun. 11, 1998.

(51) Int. Cl.[7] .................. A61K 31/4965; A61M 5/178; A61M 25/00; A61M 39/00; B01D 61/28
(52) U.S. Cl. .................. 514/255.06; 427/2.3; 604/199; 604/269; 623/1.46
(58) Field of Search ...................... 427/2.3; 514/255.06; 544/408; 604/195, 265; 623/1.46

(56) References Cited

U.S. PATENT DOCUMENTS

| | | | |
|---|---|---|---|
| 4,418,052 A | 11/1983 | Wong | 424/1.1 |
| 4,980,148 A | 12/1990 | Dean | 424/9 |
| 5,011,686 A | 4/1991 | Pang | 424/94.1 |
| 5,024,829 A | 6/1991 | Berger et al. | 424/1.1 |
| 5,122,361 A | 6/1992 | Kung et al. | 424/1.1 |
| 5,466,811 A | 11/1995 | Alexander | 546/283 |
| 5,656,600 A | 8/1997 | Abelman et al. | 514/13 |

FOREIGN PATENT DOCUMENTS

| | | |
|---|---|---|
| CA | 2164684 | 6/1996 |
| EP | 0 604 022 A1 | 6/1994 |
| EP | 0 761 251 A1 | 3/1997 |
| EP | 0 363 284 B1 | 5/1997 |
| WO | WO 95/07291 | 3/1995 |
| WO | WO 96/11668 | 4/1996 |
| WO | WO 96/18644 | 6/1996 |
| WO | WO 96/32143 | 10/1996 |
| WO | WO 96/38136 | 12/1996 |
| WO | WO 97/01338 | 1/1997 |
| WO | WO 97/11693 | 4/1997 |
| WO | WO 97/30708 | 8/1997 |
| WO | WO 97/36580 | 10/1997 |
| WO | WO 97/40024 | 10/1997 |
| WO | WO 97/46207 | 12/1997 |
| WO | WO 98/09987 | 3/1998 |
| WO | WO 98/23565 | 6/1998 |
| WO | WO 99/11267 | 3/1999 |
| WO | WO 02/09711 A1 | *2/2002 |

OTHER PUBLICATIONS

Brown, F.J. et al., "Design of Orally Active, Non–Peptidic Inhibitors of Human Leukocyte Elastase," *J. Med. Chem.* 37:1259–1261, American Chemical Society (1994).

Claeson, G., "Synthetic peptides and peptidomimetics as substrates and inhibitors of thrombin and other proteases in the blood coagulation system," *Blood Coagulation & Fibrinolysis* 5:411–436, Rapid Communications of Oxford Ltd (1994).

Coughlin, S.R., "Molecular Mechanisms of Thrombin Signaling," *Semin. Hematol.* 31:270–277, W.B. Saunders Company (1994).

de Roos, A. et al., "Myocardial infarct sizing and assessment of reperfusion by magnetic resonance imaging: a review," *Intl. J. Cardiac Imaging* 7:133–138, Kluwer Academic Publishers (1991).

Edwards, P.D. et al., "Design, Synthesis, and Kinetic Evaluation of a Unique Class of Elastase Inhibitors, the Peptidyl α–Ketobenzoxazoles, and the X–ray Crystal Structure of the Covalent Complex between Porcine Pancreatic Elastase and Ac–Ala–Pro–Val–2–Benzoxazole," *J. Am. Chem. Soc.* 114:1854–1863, American Chemical Society (1992).

(List continued on next page.)

Primary Examiner—Mukund J. Shah
Assistant Examiner—Thomas McKenzie
(74) Attorney, Agent, or Firm—Sterne, Kessler, Goldstein & Fox P.L.L.C.

(57) ABSTRACT

Thromboresistant materials are described which incorporate pyrazinone compounds of the Formula I:

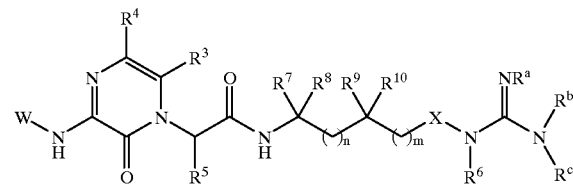

I wherein X is O, $NR^{11}$ or CH=N, $R^3$-$R^{11}$, $R^a$, $R^b$, $R^c$, W, m, and n are set forth in the specification, as well as hydrates, solvates or pharmaceutically acceptable salts thereof. The compounds of the invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin. Compositions for inhibiting loss of blood platelets, inhibiting formation of blood platelet aggregates, inhibiting formation of fibrin, inhibiting thrombus formation, and inhibiting embolus formation are described. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents. Additionally, the compounds can be detectably labeled and employed for in vivo imaging of thrombi.

25 Claims, No Drawings

OTHER PUBLICATIONS

Harker, L.A., "Strategies for inhibiting the effects of thrombin," *Blood Coagulation & Fibrinolysis* 5:s47–s58, Rapid Communications of Oxford Ltd (1994).

Jeong, J.–H. et al., "Cyclic Guanidino–Sugars with Low $pK_a$ as Transition–State Analog Inhibitors of Glycosidases: Neutral Instead of Charged Species Are the Active Forms," *J. Am. Chem. Soc.* 118:4227–4234, American Chemical Society (1996).

Kim, K.S. et al., "Preparation of Argatroban Analog Thrombin Inhibitors with Reduced Basic Guanidine Moiety, And Studies of Their Cell Permeability and Antithrombotic Activities," *Med. Chem. Res.* 6:377–383, Birkhäuser Boston (1996).

Kimball, S.D., "Challenges in the development of orally bioavailable thrombin active site inhibitors," *Blood Coagulation & Fibrinolysis* 6:511–519, Rapid Science Publishers (1995).

Lefkovits, J. and Topol, E.J., "Direct Thrombin Inhibitors in Cardiovascular Medicine," *Circulation* 90:1522–1536, American Heart Association, Inc. (1994).

Mack, H. et al., "Design, Synthesis and Biological Activity of Novel Rigid Amidino–Phenylalanine Derivatives as Inhibitors of Thrombin," *J. Enzyme Inhibiton* 9:73–86, Harwood Academic Publishers GmbH (1995).

Powers, W.J. et al., "Indium–111 platelet scintigraphy in cerebrovascular disease," *Neurology* 32:938–943, The American Academy of Neurology (1982).

Ripka, W.C. and Vlasuk, G.P., "Chapter 8. Antithrombotics/ Serine Proteases," *Ann. Rep. Medicinal Chem.* 32:71–89, Academic Press, Inc. (1997).

Saulnier, M.G. et al., "An Efficient Method for the Synthesis of Guanidino ProDrugs," *Bioorg. & Medicinal Chem. Letters* 4:1985–1990, Elsevier Science Publishers Ltd (1994).

Tapparelli, C. et al., "Synthetic low–molecular weight thrombin inhibitors: molecular design and pharmacological profile," *TiPS* 14:366–376, Elsevier Science Publishers Ltd (1993).

Thakur, M.L. et al., "Indium–111 Labeled Platelets: Studies on Preparation and Evaluation of In Vitro and In Vivo Functions," *Thrombosis Res.* 9:345–357, Pergamon Press, Inc. (1976).

Dialog File 351: Derwent WPI, English Language abstract of WO 96/32143 (Document AL2).

\* cited by examiner

THROMBORESISTANT MATERIALS INCORPORATING PYRAZINONE PROTEASE INHIBITORS

CROSS REFERENCE TO RELATED APPLICATION

This application claims benefit under 35 U.S.C. §120 as a divisional of U.S. application Ser. No. 09/330,128, now U.S. Pat. No. 6,204,263 filed Jun. 11, 1999, now U.S. Pat. No. 6,204,263, which claims benefit under 35 U.S.C. §119 (e) of U.S. Provisional Application No. 60/088,989, filed Jun. 11, 1998, the contents of which applications are fully incorporated by reference herein.

BACKGROUND OF THE INVENTION

1. Field of the Invention

The present invention relates to novel compounds that function as proteolytic enzyme inhibitors, and particularly to a new class of thrombin inhibitors.

2. Related Art

Proteases are enzymes that cleave proteins at single, specific peptide bonds. Proteases can be classified into four generic classes: serine, thiol or cysteinyl, acid or aspartyl, and metalloproteases (Cuypers et al., *J. Biol. Chem.* 257:7086 (1982)). Proteases are essential to a variety of biological activities, such as digestion, formation and dissolution of blood clots, reproduction and the immune reaction to foreign cells and organisms. Aberrant proteolysis is associated with a number of disease states in man and other mammals. The human neutrophil proteases, elastase and cathepsin G, have been implicated as contributing to disease states marked by tissue destruction. These disease states include emphysema, rheumatoid arthritis, corneal ulcers and glomerular nephritis. (Barret, in *Enzyme Inhibitors as Drugs*, Sandler, ed., University Park Press, Baltimore, (1980)). Additional proteases such as plasmin, C-1 esterase, C-3 convertase, urokinase, plasminogen activator, acrosin, and kallikreins play key roles in normal biological functions of mammals. In many instances, it is beneficial to disrupt the function of one or more proteolytic enzymes in the course of therapeutically treating a mammal.

Serine proteases include such enzymes as elastase (human leukocyte), cathepsin G, plasmin, C-1 esterase, C-3 convertase, urokinase, plasminogen activator, acrosin, chymotrypsin, trypsin, thrombin, factor Xa and kallikreins.

Human leukocyte elastase is released by polymorphonuclear leukocytes at sites of inflammation and thus is a contributing cause for a number of disease states. Cathepsin G is another human neutrophil serine protease. Compounds with the ability to inhibit the activity of these enzymes are expected to have an anti-inflammatory effect useful in the treatment of gout, rheumatoid arthritis and other inflammatory diseases, and in the treatment of emphysema. Chymotrypsin and trypsin are digestive enzymes. Inhibitors of these enzymes are useful in treating pancreatitis. Inhibitors of urokinase and plasminogen activator are useful in treating excessive cell growth disease states, such as benign prostatic hypertrophy, prostatic carcinoma and psoriasis.

The serine protease thrombin occupies a central role in hemostasis and thrombosis, and as a multifactorial protein, induces a number of effects on platelets, endothelial cells, smooth muscle cells, leukocytes, the heart, and neurons. Activation of the coagulation cascade through either the intrinsic pathway (contact activation) or the extrinsic pathway (activation by exposure of plasma to a non-endothelial surface, damage to vessel walls or tissue factor release) leads to a series of biochemical events that converge on thrombin. Thrombin cleaves fibrinogen ultimately leading to a hemostatic plug (clot formation), potently activates platelets through a unique proteolytic cleavage of the cell surface thrombin receptor (Coughlin, *Seminars in Hematology* 31(4):270–277 (1994)), and autoamplifies its own production through a feedback mechanism. Thus, inhibitors of thrombin function have therapeutic potential in a host of cardiovascular and non-cardiovascular diseases.

Factor Xa is another serine protease in the coagulation pathway. Factor Xa associates with factor Va and calcium on a phospholipid membrane thereby forming a prothrombinase complex. This prothrombinase complex then converts prothrombin to thrombin (Claeson, *Blood Coagulation and Fibrinolysis* 5:411–436 (1994); Harker, *Blood Coagulation and Fibrinolysis* 5 (*Suppl* 1):S47-S58 (1994)). Inhibitors of factor Xa are thought to offer an advantage over agents that directly inhibit thrombin since direct thrombin inhibitors still permit significant new thrombin generation (Lefkovits and Topol, *Circulation* 90(3):1522–1536 (1994); Harker, *Blood Coagulation and Fibrinolysis* 5 (*Suppl* 1):S47-S58 (1994)).

In vivo diagnostic imaging methods for intravascular thrombi have been previously reported. These imaging methods use compounds that are detectably labeled with radioactive or paramagnetic atoms. For example, platelets labeled with the gamma emitter, In-111, can be employed as an imaging agent for detecting thrombi (Thakur, M. L. et al., *Thromb Res.* 9:345 (1976); Powers et al., *Neurology* 32:938 (1982)). The thrombolytic enzyme streptokinase labeled with Tc-99m has been proposed as an imaging agent (Wong, U.S. Pat. No. 4,418,052(1983)). The fibrin-binding domains of *Staphylococcus aureus* derived protein A labeled with the gamma emitters, I-125 and I-131, have been proposed as imaging agents (Pang, U.S. Pat. No. 5,011,686 (1991)). Monoclonal antibodies having specificity for fibrin (in contrast to fibrinogen) and labeled with Tc-99m have been proposed as imaging agents (Berger et al., U.S. Pat. No. 5,024,829 (1991); Dean et al., U.S. Pat. No. 4,980,148 (1990)). The use of the paramagnetic contrasting agent, gadolinium diethylenetriaminepentaacetic acid in magnetic resonance imaging of patients treated by thrombolysis for acute myocardial infarction has been reported (De Roos, A. et al., *Int. J. Card. Imaging* 7:133 (1991)). Radiolabeled and paramagnetically labeled alpha-ketoamide derivatives have also been proposed as thrombus imaging agents (Abelman et al., U.S. Pat. No. 5,656,600).

A need continues to exist for non-peptidic compounds that are potent and selective protease inhibitors, and which possess greater bioavailability and fewer side-effects than currently available protease inhibitors. Accordingly, new classes of potent protease inhibitors, characterized by potent inhibitory capacity and low mammalian toxicity, are potentially valuable therapeutic agents for a variety of conditions, including treatment of a number of mammalian proteolytic disease states.

SUMMARY OF THE INVENTION

The present invention is directed to novel aminoguanidine (hydrazinoamidine) and alkoxyguanidine (alkoxyaminoamidine) pyrazinones having Formula I (below). Also provided are processes for preparing compounds of Formula I. The novel compounds of the present invention are potent inhibitors of proteases, especially trypsin-like serine proteases, such as chymotrypsin, trypsin, thrombin, plasmin and factor Xa. Certain of the compounds exhibit antithrombotic activity via direct, selective inhibition of thrombin, or are intermediates useful for forming compounds having antithrombotic activity. Also provided are methods of inhibiting or treating aberrant proteolysis in a mammal and methods of treating thrombosis, ischemia, stroke, restenosis or inflammation in a mammal by administering an effective amount of a compound of Formula I.

The invention includes a composition for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compositions may optionally include anticoagulants, antiplatelet agents, and thrombolytic agents. The compositions can be added to blood, blood products, or mammalian organs in order to effect the desired inhibitions.

Also provided are methods of inhibiting or treating aberrant proteolysis in a mammal, and methods for treating myocardial infarction; unstable angina; stroke; restenosis; deep vein thrombosis; disseminated intravascular coagulation caused by trauma, sepsis or tumor metastasis; hemodialysis; cardiopulmonary bypass surgery; adult respiratory distress syndrome; endotoxic shock; rheumatoid arthritis; ulcerative colitis; induration; metastasis; hypercoagulability during chemotherapy; Alzheimer's disease; Down's syndrome; fibrin formation in the eye; and wound healing. Other uses of compounds of the invention are as anticoagulants either embedded in or physically linked to materials used in the manufacture of devices used in blood collection, blood circulation, and blood storage, such as catheters, blood dialysis machines, blood collection syringes and tubes, blood lines and stents.

The invention also includes a method for reducing the thrombogenicity of a surface in a mammal by attaching to the surface, either covalently or noncovalently, a compound of the invention.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are useful for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

DETAILED DESCRIPTION OF THE PREFERRED EMBODIMENTS

Compounds of the present invention include compounds of Formula I:

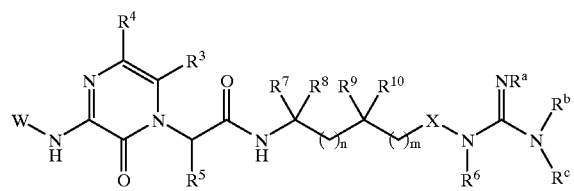

or a solvate, hydrate or pharmaceutically acceptable salt thereof; wherein:

W is hydrogen, $R^1$, $R^1OCO$, $R^1CO$, $R^1(CH_2)_sNHCO$, or $(R^1)_2CH(CH_2)_sNHCO$, wherein s is 0–4;

$R^1$ is $R^2$, $R^2(CH_2)_tC(R^{12})_2$, where t is 0–3, and each $R^{12}$ can be the same or different, $(R^2)(OR^{12})CH(CH_2)_p$, where p is 1–4, $(R^2)_2(OR^{12})C(CH_2)_p$, where p is 1–4, $R^2C(R^{12})_2(CH_2)_t$, wherein t is 0–3, and each $R^{12}$ can be the same or different, wherein $(R^{12})_2$ can also form a ring with C represented by $C_{3-7}$ cycloalkyl, $R^2CF_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl, $R^2CH_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl, $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7-membered mono- or bicyclic heterocyclic ring which can be saturated or unsaturated, and which contains from one to three heteroatoms selected from the group consisting of N, O and S, $R^2O(CH_2)_p$, wherein p is 2–4, $(R^2)_2CF(CH_2)_r$, wherein r is 0–4 and each $R^{12}$ can be the same different, wherein $(R^{12})_2$ can also form a ring with C represented by $C_{3-7}$ cycloalkyl, $C_{7-12}$ bicyclic alkyl, $C_{10-16}$ tricyclic alkyl, or a 5- to 7-membered mono- or bicyclic heterocyclic ring which can be saturated or unsaturated, and which contains from one to three heteroatoms selected from the group consisting of N, O and S,

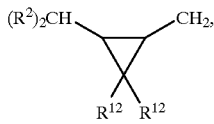

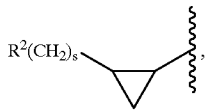

where s is 0 or 1, or $R^2CF_2C(R^{12})_2$;

$R^2$ is phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, $CONH_2$, or $SO_2NH_2$, a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy, $C_{1-7}$ alkyl, unsubstituted or substituted with one or more of hydroxy, COOH, amino, aryl, $C_{3-7}$ cycloalkyl, $CF_3$, $N(CH_3)_2$, —$C_{1-3}$alkylaryl, heteroaryl, or heterocycloalkyl, $CF_3$, $C_{3-7}$ cycloalkyl, unsubstituted or substituted with aryl, $C_{7-12}$ bicyclic alkyl, or $C_{10-16}$ tricyclic alkyl;

$R^3$ is hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_2R^x$, —$CH_2OR^x$ or —$OR^x$, where $R^x$, in each instance, is independently one of hydrogen, alkyl or cycloalkyl wherein said alkyl or cycloalkyl groups may optionally have one or more unsaturations;

$R^4$ is hydrogen or halogen;

$R^{12}$ is hydrogen, phenyl, naphthyl, or biphenyl, each of which is unsubstituted or substituted with one or more of $C_{1-4}$ alkyl, $C_{1-4}$ alkoxy, halogen, hydroxy, $CF_3$, $OCF_3$, COOH, or $CONH_2$, a 5- to 7-membered mono- or a 9- to 10-membered bicyclic heterocyclic ring which can be saturated or unsaturated, and which contains from one to four heteroatoms selected from the group consisting of N, O and S, $C_{1-4}$ alkyl, unsubstituted or substituted with one or more of hydroxy, COOH, amino, aryl, heteroaryl, or heterocycloalkyl, $CF_3$, $C_{3-7}$ cycloalkyl, $C_{7-12}$ bicyclic alkyl, or $C_{10-16}$ tricyclic alkyl;

$R^5$ is hydrogen, $C_{1-4}$alkyl, or $C_{2-4}$ alkenyl;

$R^6$ is hydrogen, alkyl, alkenyl, aralkyl, aryl, hydroxyalkyl, aminoalkyl, monoalkylamino($C_{2-10}$)alkyl, dialkylamino($C_{2-10}$)alkyl or carboxyalkyl;

$R^7$, $R^8$, $R^9$ and $R^{10}$ are independently hydrogen, alkyl, aralkyl, aryl, hydroxyalkyl, aminoalkyl, monoalkylaminoalkyl, dialkylaminoalkyl or carboxyalkyl;

or $R^7$ and $R^8$ are taken together to form —$(CH_2)_u$—, where u is 2 to 7, preferably 2 to 5, while $R^9$ and $R^{10}$ are defined as above;

or $R^9$ and $R^{10}$ are taken together to form —$(CH_2)_v$—, where v is 2 to 7, preferably 2 to 5, while $R^7$ and $R^8$ are defined as above;

or $R^7$ and $R^9$ are taken together to form —$(CH_2)_y$—, where y is 0 (a bond) or 1 to 7, preferably 0–4, while $R^8$ and $R^{10}$ are defined as above;

X is oxygen, $NR^{11}$, or CH=N (where N is bonded to $NR^6$)

where $R^{11}$ is hydrogen, alkyl, cycloalkyl or aryl, wherein said alkyl, cycloalkyl or aryl can be optionally substituted with amino, monoalkylamino, dialkylamino, alkoxy, hydroxy, carboxy, alkoxycarbonyl, aryloxycarbonyl, aralkoxycarbonyl, aryl, heteroaryl, acylamino, cyano or trifluoromethyl;

$R^a$, $R^b$ and $R^c$ are independently hydrogen, alkyl, hydroxy, alkoxy, aryloxy, aralkoxy, alkoxycarbonyloxy, cyano or —$CO_2R^w$, where $R^w$ is alkyl, cycloalkyl, phenyl, benzyl,

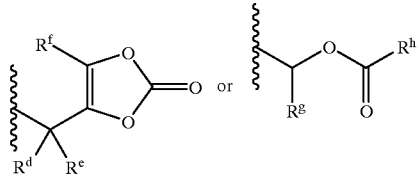

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;

n is from zero to 8; and m is from zero to 6.

In one class of compounds and pharmaceutically acceptable salts thereof, $R^3$ is hydrogen, $C_{1-4}$ alkyl, $C_{3-7}$ cycloalkyl, or $CF_3$; preferably $C_{1-4}$ alkyl, and m and n are each 0 to 4.

In a subclass of this class of compounds and pharmaceutically acceptable salts thereof, $R^4$ is hydrogen or halogen.

In a group of this subclass of compounds and pharmaceutically acceptable salts thereof, W is H or $R^1$.

In a subgroup of this group of compounds and pharmaceutically acceptable salts thereof, $R^1$ is $R^2$, $R^2(CH_2)_tC(R^{12})_2$, where t is 0–3, and each $R^{12}$ can be the same or different, $R^2C(R^{12})_2(CH_2)_t$, wherein t is 0–3, and each $R^{12}$ can be the same or different, wherein $(R^{12})_2$ can also form a ring with C represented by $C_{3-7}$ cycloalkyl, $R^2CH_2C(R^{12})_2(CH_2)_q$, wherein q is 0–2, and each $R^{12}$ can be the same or different, wherein $(R^{12})_2$ can also form a ring with C represented by $C_{3-7}$cycloalkyl, $(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7-membered mono- or bicylic heterocyclic ring which can be saturated or unsaturated, and which contains from one to three hetero atoms selected from the group consisting of N, O and S, $R^2CF_2C(R^{12})_2(CH_2)_q$, wherein q is 0–2, and each $R^{12}$ can be the same or different, wherein $(R^{12})_2$ can also form a ring with C represented by $C_{3-7}$cycloalkyl, or $R^2O(CH_2)_p$, wherein p is 2–4;

$R^2$ is phenyl or naphthyl, each of which is unsubstituted or substituted with one or more of $C_{1-4}$ alkyl, $C_{1-4}$ alkoxy, halogen, hydroxy, $CF_3$, $OCF_3$, or $SO_2NH_2$, a 5- to 7-membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen or hydroxy, $C_{1-7}$ alkyl, unsubstituted or substituted with one or more of hydroxy, COOH, $C_{3-7}$ cycloalkyl, $CF_3$, $N(CH_3)_2$, —$C_{1-3}$alkylaryl, heteroaryl, or heterocycloalkyl, $CF_3$, or $C_{3-7}$ cycloalkyl, unsubstituted or substituted with aryl; and $R^{12}$ is hydrogen, or $C_{1-4}$ alkyl, unsubstituted or substituted with one or more of hydroxy, COOH, amino, aryl, heteroaryl, or heterocycloalkyl.

In a family of this subgroup of compounds and pharmaceutically acceptable salts thereof, $R^3$ is H, $CH_3$, or $CH_2CH_3$;

$R^4$ is H or chloro; and

W is $PhCH_2CH_2$, $(CH_3)_3C$—, $HOOCCH_2$, $CF_3CH_2$, $(CH_3)_2N(CH_2)_2$, $PhCH_2O(CH_2)_2$, $PhCH(CH_3)$, $PhCH_2CH(COOH)$, $CH_3(CH_2)_5$, $PhCH_2$, H, $CH_3(CH_2)_4$, $CH_3CH_2CH(CH_3)CH_2$, $(Ph)_2CHCH_2$, $PhCH_2CH(CH_3)$, $PhCH(CH_3)CH_2$, $(CH_3)_2CH$, $PhCH(OH)CH_2$, $PhC(CH_3)_2CH_2$, $(Ph)_2CHCH_2$, or

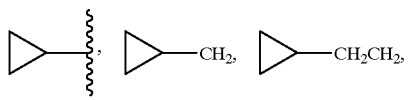

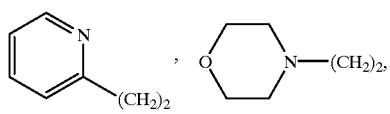

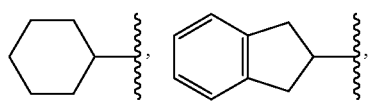

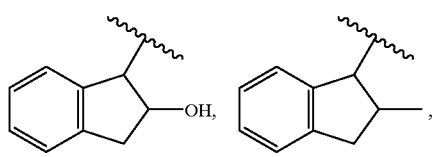

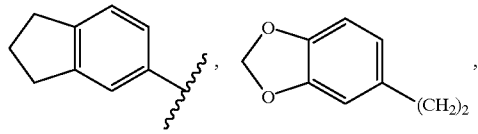

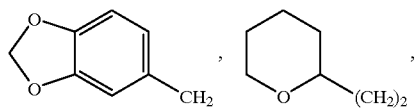

-continued

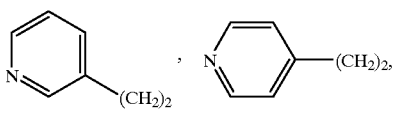

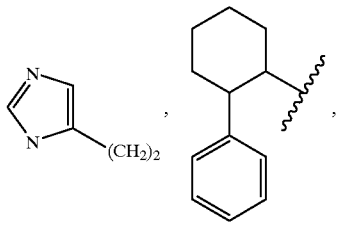

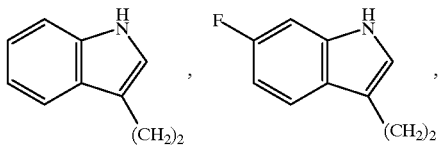

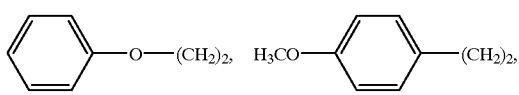

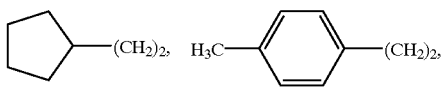

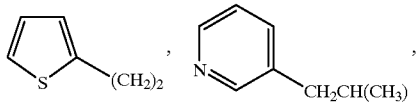

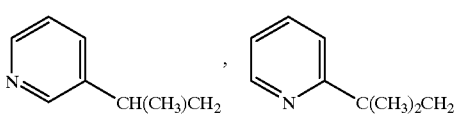

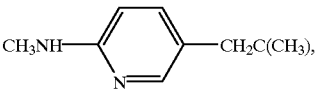

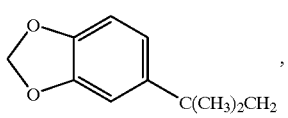

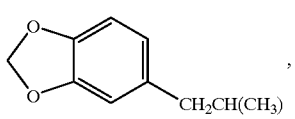

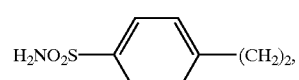

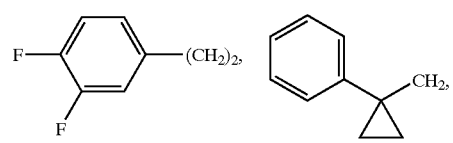

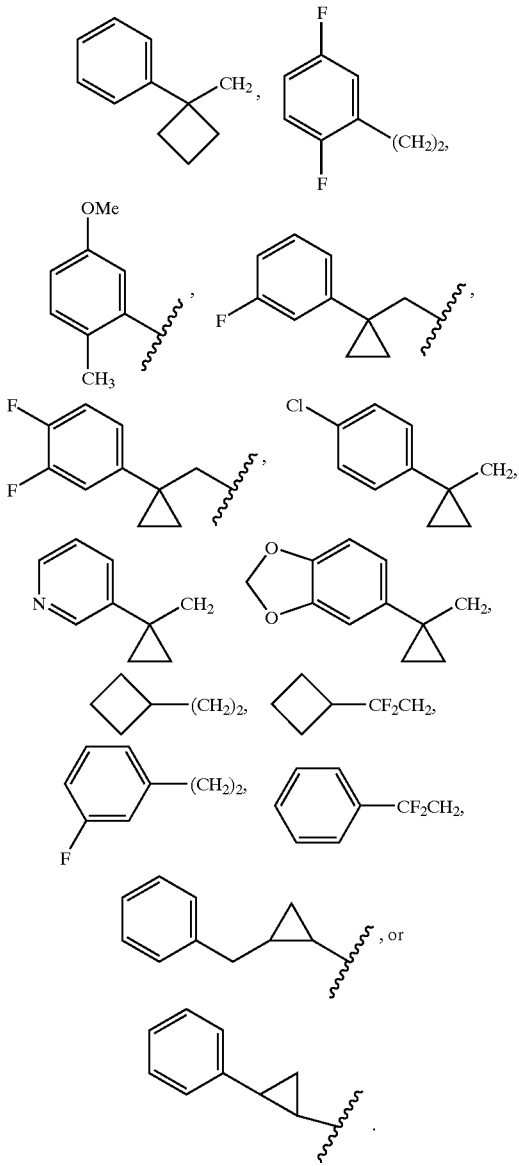

A preferred $R^5$ group is hydrogen.

Preferred compounds when X is $NR^{11}$ are those wherein $R^{11}$ is hydrogen or $C_{1-6}$ alkyl, optionally substituted by one, two or three, preferably one, of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

Suitable values of $R^{11}$ include hydrogen, methyl, ethyl, propyl, n-butyl, benzyl, phenethyl, 2-hydroxyethyl, 3-hydroxypropyl, 4-hydroxybutyl, carboxymethyl and carboxyethyl.

Most preferred compounds are those where X is oxygen.

Preferred compounds are those of Formula I, where $R^6$ is hydrogen or $C_{1-6}$ alkyl.

Preferred compounds are those of Formula I, where $R^7$, $R^8$, $R^9$ and $R^{10}$ are independently one of hydrogen, $C_{1-6}$ alkyl, $C_{6-10}$ ar($C_{1-6}$)alkyl, $C_{6-10}$ aryl, $C_{2-10}$ hydroxyalkyl or $C_{2-7}$ carboxyalkyl. Useful values of $R^7$, $R^8$, $R^9$ and $R^{10}$ include hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl and 4-carboxypropyl.

Also preferred are compounds where either $R^7$ and $R^8$, or $R^9$ and $R^{10}$ combine as an alkylene linker, $—(CH_2)_u—$ and $—(CH_2)_v—$ respectively, where u and v are each 2–5, most preferably 2 or 3.

Preferred values of $R^a$, $R^b$ and $R^c$ in Formula I are hydrogen, hydroxy, $C_{1-6}$ alkyl, $C_{1-6}$ alkoxy, cyano or $—CO_2R^w$, where $R^w$, in each instance, is preferably one of $C_{1-4}$alkyl, $C_{4-7}$cycloalkyl or benzyloxycarbonyl. Suitable values of $R^a$, $R^b$ and $R^c$ include hydrogen, methyl, ethyl, propyl, n-butyl, hydroxy, methoxy, ethoxy, cyano, $—CO_2CH_3$, $—CO_2CH_2CH_3$ and $—CO_2CH_2CH_2CH_3$. In the most preferred embodiments, $R^a$, $R^b$ and $R^c$ are each hydrogen.

Also preferred at $R^a$, $R^b$ and $R^c$ is the group $—CO_2R^w$, where $R^w$ is one of

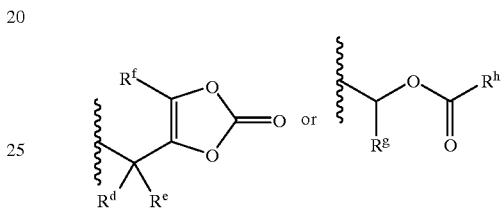

where $R^d$–$R^h$ are defined as above. When $R^a$, $R^b$ and $R^c$ are $—CO_2R^w$, where $R^w$ is one of these moieties, the resulting compounds are prodrugs that possess desirable formulation and bioavailability characteristics. A preferred value for each of $R^d$, $R^e$ and $R^g$ is hydrogen, $R^w$ is methyl, and preferred values for $R^h$ include benzyl and tert-butyl.

Preferred values of n in Formula I include from zero to 6, more preferably from zero to 4, and most preferably zero, 1 or 2.

Preferred values of m are from zero to 4, most preferably zero, 1 or 2.

Especially preferred compounds are represented by Formulae II, III and IV:

II

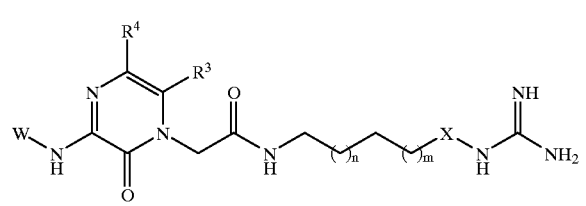

III

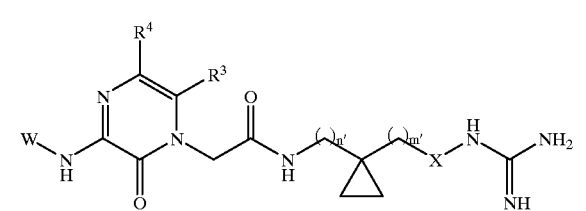

-continued

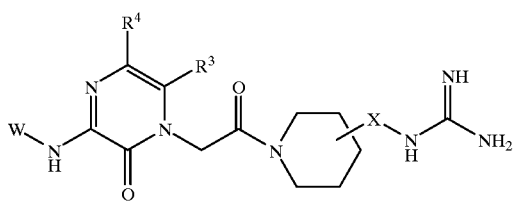

IV or a solvate, hydrate or pharmaceutically acceptable salt thereof; wherein

W is as defined, and has the preferred values, as for Formula I, above;

X is —O—, —NH— or —CH=N— (an amidinohydrazone group, where the NH is attached to the NH group of the parent formula). X is preferably attached to the 3- or 4- position of the ring, most preferably the 4- position.

$R^3$ is hydrogen, $C_{1-3}$ alkyl, halogen or $C_{1-2}$ alkoxy;

$R^4$ is hydrogen or halogen;

n is 0, 1, 2 or 3, preferably 0, 1 or 2;

m is 0, 1, 2 or 3, preferably 0 or 1;

n' is 0, 1, 2 or 3, preferably 0, 1 or 2; and m' is 0, 1, 2 or 3, preferably 0 or 1.

Specific compounds within the scope of the invention include the following:

1-{N-[2-(amidinoaminooxy)ethyl]amino}carbonylmethyl-6-methyl-3-(phenethylamino)-pyrazinone, 1-{N-[2-(amidinoaminooxy)ethyl]amino}carbonylmethyl-6-methyl-3-(2,2-diphenylethylamino)-pyrazinone, 1-{N-[2-(amidinoaminooxy)ethyl]amino}carbonymethyl-6-methyl-3-(4-methylphenethylamino)-pyrazinone, 1-{N-[2-(amidinoaminooxy)ethyl]amino}carbonylmethyl-6-methyl-3-(4-methoxyphenethylamino)-pyrazinone, 1-{N-[2-(amidinoaminooxy)ethyl]amino}carbonylmethyl-6-methyl-3-(1-phenylcyclobutyl)methylamino-pyrazinone, 1-{N-[2-(amidinoaaminooxy)ethyl]amino}carbonylmethyl-6-methyl-3-[2-(1-naphthalene)ethyl]amino-pyrazinone, 1-{N-[2-(amidinoaminooxy)ethyl]amino}carbonylmethyl-6-methyl-3-(2-phenyl-1-butylamino)-pyrazinone, 1-{N-[2-(amidinoaminooxy)ethyl]amino}carbonylmethyl-6-methyl-3-(2-[3,4-methylenedioxyphenyl]ethylamino)-pyrazinone, 1-{N-[2-(amidinoaminooxy)ethyl]amino}carbonylmethyl-6-methyl-3-(2-[2-pyridyl]ethylamino)-pyrazinone, 1-{N-[2-(amidinoaminooxy)ethyl]amino}carbonylmethyl-6-methyl-3-(2-[2-methylphenyl]ethylamino)-pyrazinone, 1-{N-[2-(amidinoaminooxy)ethyl]amino}carbonylmethyl-6-methyl-3-(2-[3-methylphenyl]ethylamino)-pyrazinone, 1-{N-[2-(amidinoaminooxy)ethyl]amino}carbonylmethyl-6-methyl-3-(2-[2-trifluoromethylphenyl]ethylamino)-pyrazinone, 1-{N-[2-(amidinoaminooxy)ethyl]amino}carbonylmethyl-6-methyl-3-(2-[3-trifluoromethylphenyl]ethylamino)-pyrazinone, 1-{N-[2-(amidinoaminooxy)ethyl]amino}carbonylmethyl-6-methyl-3-(2-[4-trifluoromethylphenyl]ethylamino)-pyrazinone, 1-{N-[2-(amidinoaminooxy)ethyl]amino}carbonylmethyl-6-methyl-3-(2-[3,5-dimethylphenyl]ethylamino)-pyrazinone, 1-{N-[2-(amidinoaminooxy)ethyl]amino}carbonylmethyl-6-methyl-3-(2-indanylamino)-pyrazinone, 1-{N-[2-(amidinoaminooxy)ethyl]amino}carbonylmethyl-6-methyl-3-(2-[3,4-difluorophenyl]ethylamino)-pyrazinone, 1-{N-[2-(amidinoaminooxy)ethyl]amino}carbonylmethyl-6-methyl-3-(2-[5-indanyl]ethylamino)-pyrazinone, 1-{N-[2-(amidinoaminooxy)ethyl]amino}carbonylmethyl-6-methyl-3-(2-fluorophenethylamino)-pyrazinone, 1-{N-[2-(amidinoaminooxy)ethyl]amino}carbonylmethyl-6-methyl-3-(3,4-dimethoxyphenethylamino)-pyrazinone, 1-{N-[2-(amidinoaminooxy)ethyl]amino}carbonylmethyl-6-methyl-3-(4-fluorophenethylamino)-pyrazinone, 1-{N-[2-(amidinoaminooxy)ethyl]amino}carbonylmethyl-6-methyl-3-(4-ethylphenethylamino)-pyrazinone, 1-{N-[2-(amidinoaminooxy)ethyl]amino}carbonylmethyl-6-methyl-3-(2-phenylpropylamino)-pyrazinone, 1-{N-[2-(amidinoaminooxy)ethyl]amino}carbonylmethyl-6-methyl-3-(3,4-dimethylphenethylamino)-pyrazinone, 1-{N-[2-(amidinoaminooxy)ethyl]amino}carbonylmethyl-6-methyl-3-(2-naphthaleneethylamino)-pyrazinone, 1-{N-[2-(amidinoaminooxy)ethyl]amino}carbonylmethyl-6-methyl-3-(2,2-diphenylpropylamino)-pyrazinone, 1-{N-[2-(amidinoaminooxy)ethyl]amino}carbonylmethyl-6-methyl-3-(2-(3-indolyl)-ethylamino-pyrazinone, 1-{N-[2-(amidinoaminooxy)ethyl]amino}carbonylmethyl-6-methyl-3-(2-[1-(4-methylnaphthalene)]ethylamino)-pyrazinone, 1-{N-[2-(amidinoaminooxy)ethyl]amino}carbonylmethyl-6-methyl-3-(2-[2,4-difluorophenyl]ethylamino)-pyrazinone.

1-{N-[2-(amidino-N'-methylaminooxy)ethyl]amino}carbonylmethyl-6-methyl-3-(2-[4-methylphenyl]ethylamino)-pyrazinone, 1-{N-[2-(amidinoaminooxy)ethyl]amino}carbonylmethyl-5-chloro-6-methyl-3-(phenethylamino)-pyrazinone, 1-{N-[2-(amidinoaminooxy)ethyl]amino}carbonylmethyl-5-chloro-6-methyl-3-(2,2-diphenylethylamino)-pyrazinone, 1-{N-[2-(amidinohydrazino)ethyl]amino}carbonylmethyl-6-methyl-3-(phenethyl)-pyrazinone, 1-{N-[2-(amidinohydrazino)ethyl]amino}carbonylmethyl-6-methyl-3-(1-methyl-2-phenylethyl)-pyrazinone, 1-{N-[2-(amidinohydrazino)ethyl]amino}carbonylmethyl-6-ethyl-3-(phenethyl)-pyrazinone, 1-{N-[2-(amidinohydrazino)ethyl]amino}carbonylmethyl-6-methyl-3-(4-methylphenylethyl)-pyrazinone, 1-{N-[2-(amidinoaminooxy)ethyl]amino}carbonylmethyl-6-methyl-3-(1-methyl-2-(4-methylamino-3-pyridyl)ethyl-pyrazinone, 1-{N-[2-(amidinoaminooxy)ethyl]amino}carbonylmethyl-6-methyl-3-(1-methyl-2-(3-pyridyl)ethyl-pyrazinone, 1-{N-[2-(amidinoaminooxy)ethyl]amino}carbonylmethyl-6-methyl-3-(2-cyclopropyl-2-(3,4-dimethoxyphenyl)ethyl)-pyrazinone, 1-{N-[2-(amidinoaminooxy)ethyl]amino}carbonylmethyl-6-methyl-3-(2-cyclobutylethyl)-pyrazinone, 1-{N-[2-(amidinoaminooxy)ethyl]amino}carbonylmethyl-6-methyl-3-(2-cyclobutyl-2,2-difluoroethyl)-pyrazinone, 1-{N-[2-(amidinoaminooxy)ethyl]amino}carbonylmethyl-6-methyl-3-(2-(3-fluorophenyl)ethyl)-pyrazinone, 1-{N-[2-(amidinoaminooxy)ethyl]amino}carbonylmethyl-6-methyl-3-(2,2-difluoro-2-phenylethyl)-pyrazinone, 1-{N-[2-(amidinoaminooxy)ethyl]amino}carbonylmethyl-6-methyl-3-(2-phenylcyclopropyl)-pyrazinone, 1-{N-[2-(amidinoaminooxy)ethyl]amino}carbonylmethyl-6-methyl-3-(2-(4-chlorophenyl)-2-cyclopropylethyl)-pyrazinone, 1-{N-[2-(amidinoaminooxy)ethyl]amino}carbonylmethyl-6-methyl-3-(2-cyclopropyl-2-(3-pyridyl)ethyl)-pyrazinone, 1-{N-[2-(amidinoaminooxy)ethyl]amino}carbonylmethyl-6-methyl-3-(2-benzylcylopropyl)-pyrazinone, 1-{N-[2-(amidinoaminooxy)ethyl]amino}carbonylmethyl-6-methyl-3-(2-cyclopropyl-2-(3-fluorophenyl)ethyl)-pyrazinone, 1-{N-[2-(amidinoaminooxy)ethyl]amino}carbonylmethyl-6-methyl-3-(2-cyclopropyl-2-(3,4-difluorophenyl)ethyl)-pyrazinone, 1-{N-[2-(amidinoaminooxy)ethyl]amino}carbonylmethyl-6-methyl-3-(2,2-difluoro-2-phenylethylamino)-pyrazinone, as well as pharmaceutically acceptable salts thereof, for example the hydrochloride, acetate and trifluoroacetate salts thereof.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present series. The compounds of the present invention may also have polymorphic crystalline forms, with all polymorphic crystalline forms being included in the present invention.

The compounds of Formula I may also be solvated, especially hydrated. Hydration may occur during manufacturing of the compounds or compositions comprising the compounds, or the hydration may occur over time due to the hygroscopic nature of the compounds.

Certain compounds within the scope of Formula I are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process. Useful prodrugs are those where $R^a$, $R^b$ and/or $R^c$ are —$CO_2R^w$, where $R^w$ is defined above. See, U.S. Pat. No. 5,466,811 and Saulnier et al., *Bioorg. Med. Chem. Lett.* 4:1985–1990 (1994).

When any variable occurs more than one time in any constituent or in Formula I, its definition on each occurrence is independent of its definition at every other occurrence. Also, combinations of substituents and/or variables are permissible only if such combinations result in stable compounds.

In another aspect, the present invention includes compositions which are useful for in vivo imaging of thrombi in a mammal, comprising a compound of the present invention which is capable of being detected outside the body. Preferred are compositions comprising a compound of the present invention and a detectable label, such as a radioactive or paramagnetic atom.

In another aspect, the present invention provides diagnostic compositions which are used for in vivo imaging of thrombi in a mammal, comprising a pharmaceutically acceptable carrier and a diagnostically effective amount of a compound or composition of the present invention.

In another aspect, the present invention includes methods which are useful for in vivo imaging of thrombi in a mammal.

According to a preferred aspect, useful compounds are those wherein the $R^1$ substituent is substituted with a detectable label, such as a radioactive iodine atom, such as I-125, I-131 or I-123. In this aspect, $R^1$ is preferably phenyl, having a para I-123, para I-125 or para I-131 substitution, or benzyl, having a meta I-123, meta I-125 or meta I-131 substitution.

The detectable label can also be a radioactive or paramagnetic chelate in which a suitable ligand (L) is attached to an $R^1$ substituent, either directly or via a divalent linking group A". Alternatively, the group —A"—L substitutes for the groups W in Formula I. By suitable ligand is meant an organic moiety that is capable of chelating a radioactive or paramagnetic metal ion.

In these compounds, the divalent linking group A" includes groups that are capable of covalently bonding with a free amino group and the chelating means. For example, A" may be —C(=S)—, —C(=O)—, —C(=NH)—$(CH_2)_6$—C(=NH)—, —C(=O)—$(CH_2)_6$—C(=O)—,

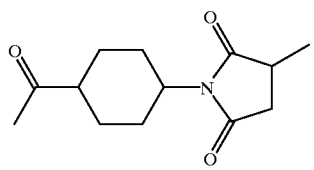

and the like.

Also, in the compounds represented by Formula I, the chelating ligand, L, includes groups capable of covalently bonding to or noncovalently binding to either a radioactive or paramagnetic atom. The chelating means including those which are customarily used for complexing radioactive or paramagnetic atoms. These include chelating means containing 3 to 12, preferably 3 to 8, methylene phosphonic acid groups, methylene carbohydroxamic acid groups, carboxyethylidene groups, or especially carboxymethylene groups, which are bonded to a nitrogen atom. If only one or two of the acid groups are bonded to a nitrogen atom, then that nitrogen is bonded to another nitrogen atom having such groups by an optionally substituted ethylene groups or by up to four separated ethylene units separated by a nitrogen or oxygen or sulfur atom. Preferred as a completing means is diethylenetrimine-N,N,N',N'',N''-pentaacetic acid (DTPA). DTPA is well known in the art as a chelating means for the radioactive atom indium-111 (In-111), technetium-99m (Tc-99m), and the paramagnetic atom gadolinium (Gd). Khaw, et al., *Science* 209:295 (1980); Paik C. H. et al., U.S. Pat. No. 4,652,440 (1987); Gries, H. et al., U.S. Pat. No. 4,957,939 (1990). An preferred chelating ligand, L, is 1-(p-aminobenzyl)-diethylenetriaminepentaacetic acid. Also included as chelating means are compounds which contain sulfhdryl or amine moieties, the total of which in any combination is at least four. These sulfhydryl or amine moieties are separated from each other by at least two atoms which can be either carbon, nitrogen, oxygen, or sulfur. Especially preferred for chelating means, L, is metallothionein which is well known in the art as a chelating means for Tc-99m.

The term "alkyl" as employed herein by itself or as part of another group refers to both straight and branched chain radicals of up to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" is used herein to mean a straight or branched chain radical of 2–20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" is used herein to mean a straight or branched chain radical of 2–20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

In all instances herein where there is an alkenyl or alkynyl moiety as a substituent group, the unsaturated linkage, i.e., the vinylene or acetylene linkage is preferably not directly attached to a nitrogen, oxygen or sulfur moiety.

The term "alkoxy" is used herein to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length.

The term "aryl" as employed herein by itself or as part of another group refers to monocyclic or bicyclic aromatic groups containing from 6 to 12 carbons in the ring portion, preferably 6–10 carbons in the ring portion, such as phenyl, naphthyl or tetrahydronaphthyl.

The term "heteroaryl" as employed herein refers to groups having 5 to 14 ring atoms; 6, 10 or 14π electrons shared in a cyclic array; and containing carbon atoms and 1, 2 or 3 oxygen, nitrogen or sulfur heteroatoms (where examples of heteroaryl groups are: thienyl, benzo[b]thienyl, naphtho[2, 3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimindinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, 4αH-carbazolyl, carbazolyl, β-carbolinyl, phenanthridinyl, acridinyl, perimidinyl, phenanthrolinyl, phenazinyl, isothiazolyl, phenothiazinyl, isoxazolyl, furazanyl and phenoxazinyl groups).

The term "aralkyl" or "arylalkyl" as employed herein by itself or as part of another group refers to $C_{1-6}$alkyl groups as discussed above having an aryl substituent, such as benzyl, phenylethyl or 2-naphthylmethyl.

The term "cycloalkyl" as employed herein by itself or as part of another group refers to cycloalkyl groups containing 3 to 9 carbon atoms, preferably 3 to 7 carbon atoms. Typical examples are cyclopropyl, cyclobutyl, cyclopentyl, cyclohexyl, cycloheptyl, cyclooctyl and cyclononyl.

The term "$C_{7-12}$ bicyclic alkyl" is intended to include bicyclo[2.2.1]heptyl (norbornyl), bicyclo[2.2.2]octyl, 1,1,3-trimethylbicyclo[2.2.1]heptyl(bornyl), and the like.

The term "$C_{10-16}$ tricyclic alkyl" is intended to include tricyclo[5, 2, 1, $0^{2,6}$]decyl, adamantyl, and the like.

The term "halogen" or "halo" as employed herein by itself or as part of another group refers to chlorine, bromine, fluorine or iodine with chlorine being preferred.

The term "monoalkylamine" as employed herein by itself or as part of another group refers to an amino group which is substituted with one alkyl group having from 1 to 6 carbon atoms.

The term "dialkylamine" as employed herein by itself or as part of another group refers to an amino group which is substituted with two alkyl groups, each having from 1 to 6 carbon atoms.

The term "hydroxyalkyl" as employed herein refers to any of the above alkyl groups substituted by one or more hydroxyl moieties.

The term "carboxyalkyl" as employed herein refers to any of the above alkyl groups substituted by one or more carboxylic acid moieties.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The hetero cyclic ring may be attached at any hetero atom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "heteroatom" is used herein to mean an oxygen atom ("O"), a sulfur atom ("S") or a nitrogen atom ("N"). It will be recognized that when the heteroatom is nitrogen, it may form an $NR^aR^b$ moiety, wherein $R^a$ and $R^b$ are, independently from one another, hydrogen or $C_1$ to $C_8$ alkyl, or together with the nitrogen to which they are bound, form a saturated or unsaturated 5-, 6-, or 7-membered ring.

Schemes 1 and 2 outline the synthetic steps to produce compounds of Formula I.

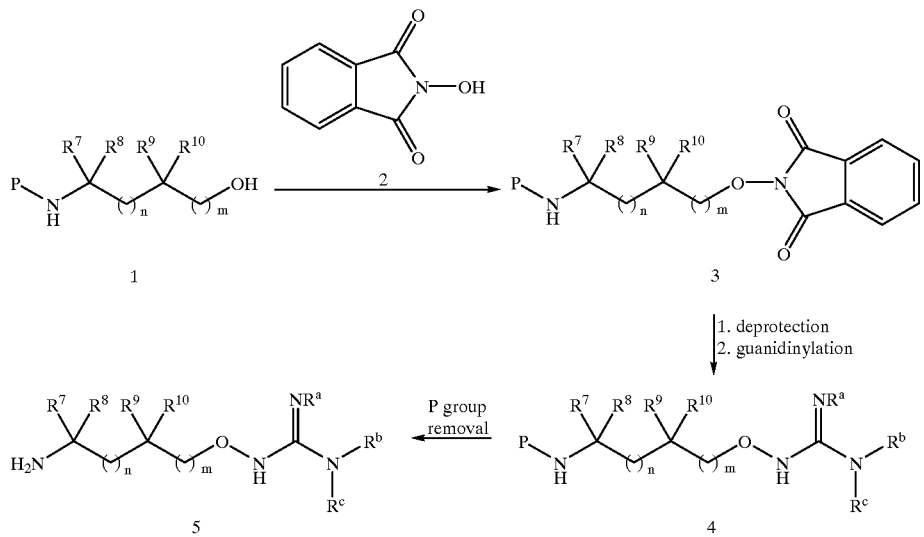

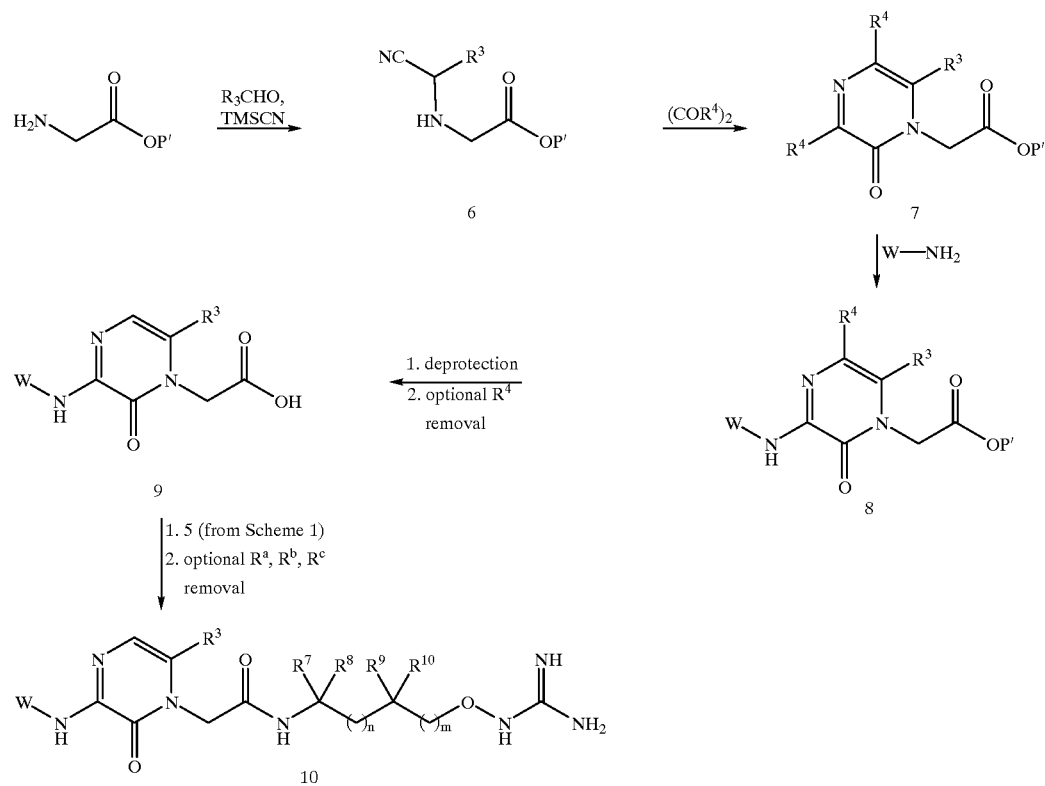

In Schemes 1 and 2, W, $R^3$, $R^7$, $R^8$, $R^9$, $R^{10}$, $R^a$, $R^b$, $R^c$, n and m are as defined above; $R^4$=Cl or Br; P is an amino protecting group, such as benzyloxycarbonyl (Cbz), and P' is an ester protecting group, such as benzyl.

In Scheme 1, protected aminoalcohol 1 is coupled to N-hydroxyphthalimide 2 using a Mitsunobu coupling procedure (Mitsunobu, O. *Synthesis* 1 (1981)) to provide compound 3. Preferred coupling conditions include using a trialkylphosphine or triarylphosphine, such as triphenylphosphine, in a suitable solvent, such as tetrahydrofuran or methylene chloride, and a dialkyl azodicarboxylate, such as diethyl azodicarboxylate. Unveiling of the phthalimide protecting group is accomplished using standard conditions well known in the art (Greene, T. W., Wuts, P. G. M., *Protective Groups in Organic Synthesis*, 2nd edition, John Wiley and Sons, Inc. New York (1991)), such as methylamine or hydrazine, in an appropriate solvent, such as ethanol or isopropanol. Guanidinylation of the resulting alkoxyamine to 4 using substituted guanidinylating reagents such as N,N'-bis(tert-butoxycarbonyl)-S-methylisothiourea (Bergeron, R. J. and McManis, J. S., *J Org. Chem.* 52:1700 (1987)) or N-$R^a$, N-$R^b$, N-$R^c$-1H-pyrazole-1-carboxamidine (Bernatowicz, M. S. et al., *Tetrahedron Letter* 34:3389 (1993)). Deprotection of the amino group to give intermediate 5 is accomplished using standard procedure well known in the art (Greene, T. W., Wuts, P. G. M., *Protective Groups in Organic Synthesis*, 2nd edition, John Wiley and Sons, Inc. New York (1991)), such as palladium on carbon, in a suitable solvent, such as methanol or ethanol. In some cases, it is advantageous to add an acid, such as hydrochloric acid.

In Scheme 2, an ester protected glycine, such as P'=benzyl, or ethyl, is condensed with an aldehyde, such as acetaldehyde, and a cyanide, such as cyanotrimethylsilane (TMSCN), in a suitable solvent, such as methylene chloride to afford the aminonitrile 6. The aminonitrile is reacted with oxalyl chloride or oxalyl bromide in an appropriate solvent, such as 1,2-dichlorobenzene to give the pyrazinone 7. The 3-chloro or 3-bromo of pyrazinone 7 is then displaced by an appropriate amine, such as phenethylamine, 2,2-diphenylethylamine or 4-methoxyphenethylamine, in an appropriate solvent, such as ethyl acetate, to give compound 8. The ester 8 is converted to the acid 9 by standard procedures well known in the art (Greene, T. W., Wuts, P. G. M., *Protective Groups in Organic Synthesis*, 2nd edition, John Wiley and Sons, Inc. New York (1991)), such as hydrolysis using base, such as LiOH or NaOH, in a suitable solvent, such as tetrahydrofuran/methanol/water. The remaining chlorine or bromine is then optionally removed by hydrogenolysis using a catalyst, such as palladium on carbon or Raney nickel, in an appropriate solvent, such as water to effort 9. Alternatively, in the case of P'=benzyl, deprotection of the benzyl ester and removal of the remaining chlorine or bromine can be achieved simultaneously using palladium on carbon in a suitable solvent, such as tetrahydrofuran/ethanol to give 9. The acid is then coupled to amine 5 using typical amino acid coupling procedures, such as BOP or PyBOP, in an appropriate solvent, such as N,N-dimethylformamide, and base, such as di-isopropylethylamine (DIEA), followed by optional removing of $R^a$, $R^b$, $R^c$, in the case of $R^a$ and $R^b$=tert-butyloxycarbonyl (Boc) and $R^c$=hydrogen. The Boc groups are removed by treatment with an acid, such as trifluoroacetic acid or hydrochloric acid, in an appropriate solvent, such as methylene chloride or dioxane to provide target compound 10.

Compounds wherein X is —CH=$NR^{11}$— or $NR^{11}$ can be formed using the steps exhibited in Scheme 3.

Scheme 3

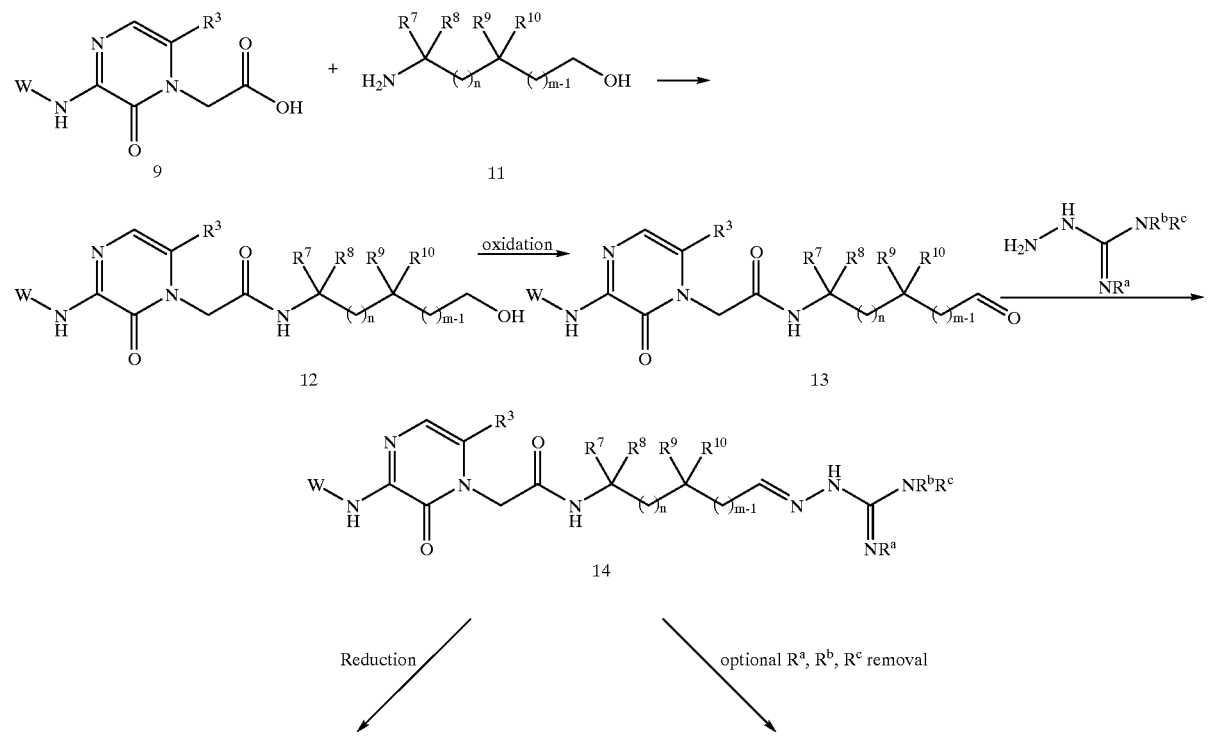

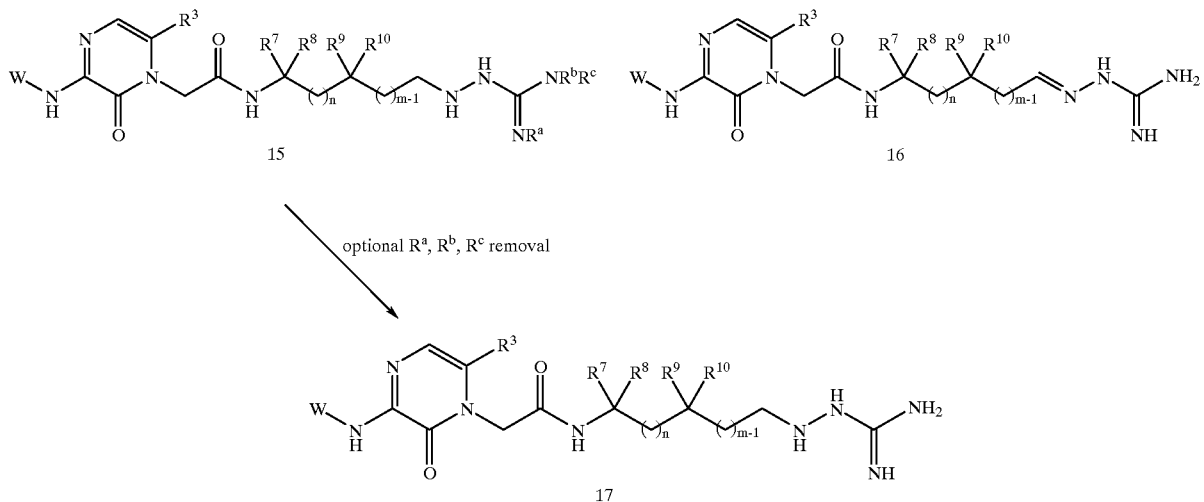

Acid 9 (as synthesized in Scheme 2) is coupled with an aminoalcohol 11 using standard amino acid coupling procedures, such as BOP or PyBOP in a solvent such as N,N-dimethylformamide, and base, such as DIEA, to form compound 12. The corresponding aldehyde 13 is synthesized using routine procedures for the oxidation of alcohols (see for example Carey, F. A., and Sundberg, R. J., *Advanced Organic Chemistry, Part B.: Reactions and Synthesis,* 3rd edition, Plenum Press, New York (1990)) such as the Swern oxidation (Mancuso, A. J. et al., *Journal of Organic Chemistry* 3329 (1976)) pyridinium chlorochromate (Corey, E. J. and Suggs, J. W. *Tetrahedron Letters* 2647 (1975)) pyridinium dichromate (Corey, E. J. and Schmidt, G. *Tetrahedron Letters* 399 (1979)), or sulfur trioxide pyridine complex/dimethylsulfoxide (*Tetrahedron Letters* 28:1603 (1987)).

The aldehyde 13 is then converted to amidinohydrazone 14 using standard conditions, for example, treatment with an aminoguanidine or a substituted aminoguanidine, such as aminoguanidine or 2-hydrazinoimidazoline, optionally in the presence of an acid such as nitric acid, hydrogen chloride, or hydrogen bromide, in an appropriate solvent, for example, ethanol or methanol, which, in addition, may contain other solvents such as dichloromethane or tetrahydrofuran.

Conversion of the amidinohydrazone 14 to the aminoguanidine 15 is accomplished under reducing conditions well known in the art, for example, lithium borohydride in appropriate solvent such as tetrahydrofuran or methanol at various temperatures up to reflux. As an alternative method, catalytic hydrogenation with palladium on carbon catalyst can be employed.

$R^a$, $R^b$, and $R^c$ in compounds 14 and 15 can optionally be removed by using conditions well known in the art. In the case of $R^a$ and $R^b$=tert-butyloxycarbonyl (Boc) and $R^c$=hydrogen, the Boc groups are removed by treatment with an acid, such as trifluoro acetic acid or hydrochloric acid, in an appropriate solvent, such as methylene chloride or dioxane to provide compounds 16 and 17 respectively.

The pharmaceutically-acceptable salts of the compounds of Formula I (in the form of water- or oil-soluble or dispersible products) include the conventional non-toxic salts or the quaternary ammonium salts which are formed, e.g., from inorganic or organic acids or bases. Examples of such acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Preferred acids for forming acid addition salts include HCl and acetic acid.

The compounds of the present invention represent a novel class of potent inhibitors of metallo, acid, thiol and serine proteases. Examples of the serine proteases inhibited by compounds within the scope of the invention include leukocyte neutrophil elastase, a proteolytic enzyme implicated in the pathogenesis of emphysema; chymotrypsin and trypsin, digestive enzymes; pancreatic elastase, and cathepsin G, a chymotrypsin-like protease also associated with leukocytes; thrombin and factor Xa, proteolytic enzymes in the blood coagulation pathway. Inhibition of thermolysin, a metalloprotease, and pepsin, an acid protease, are also contemplated uses of compounds of the present invention. The compounds of the present invention are preferably employed to ininbit trypsin-like proteases.

For their end-use application, the potency and other biochemical parameters of the enzyme-inhibiting characteristics of the compounds of the present invention is readily ascertained by standard biochemical techniques well known in the art. For example, an end use application of the compounds that inhibit chymotrypsin and trypsin is in the treatment of pancreatitis. Actual dose ranges for their specific end-use application will, of course, depend upon the nature and severity of the disease state of the patient or animal to be treated, as determined by the attending diagnostician. It is expected that a useful dose range will be about 0.01 to 10 mg per kg per day for an effective therapeutic effect.

Compounds of the present invention that are distinguished by their ability to inhibit thrombin may be employed for a number of therapeutic purposes. As thrombin inhibitors, compounds of the present invention inhibit thrombin production. Therefore, these compounds are useful for the treatment or prophylaxis of states characterized by abnormal venous or arterial thrombosis involving either thrombin production or action. These states include, but are not limited to, deep vein thrombosis; disseminated intravascular coagulopathy which occurs during septic shock, viral infections and cancer; myocardial infarction; stroke; coronary artery bypass; fibrin formation in the eye; hip replacement; and thrombus formation resulting from either thrombolytic therapy or percutaneous transluminal coronary angioplasty (PCTA). Other uses include the use of said thrombin inhibitors as anticoagulants either embedded in or physically linked to materials used in the manufacture of devices used in blood collection, blood circulation, and blood storage, such as catheters, blood dialysis machines, blood collection syringes and tubes, and blood lines. The compounds of the present invention may also be used as an anticoagulant in extracorporeal blood circuits.

Metal stents have been shown to reduce restenosis, but are thrombogenic. A strategy for reducing the thrombogenicity of stents is to coat, embed, adsord or covalently attach a thrombin-inhibiting agent to the stent surface. The compounds of the present invention can be employed for this purpose. Compounds of the invention can be attached to, or embedded within soluble and/or biodegradeable polymers as and thereafter coated onto stent materials. Such polymers can include polyvinylpyrrolidone, polyhydroxy-propylmethacrylamide-phenol, polyhydroxyethyl-aspartamide-phenol, or polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels. See European Application 761 251, European Application 604,022, Canadian Patent 2,164,684 and PCT Published Applications WO 96/11668, WO 96/32143 and WO 96/38136.

By virtue of the effects of thrombin on a host of cell types, such as smooth muscle cells, endothelial cells and neutrophils, the compounds of the present invention find additional use in the treatment or prophylaxis of adult respiratory distress syndrome; inflammatory responses; wound healing; reperfusion damage; atherosclerosis; and restenosis following an injury such as balloon angioplasty, atherectomy, and arterial stent placement.

The compounds of the present invention may be useful in treating neoplasia and metastasis as well as neurodegenerative diseases, such as Alzheimer's disease and Parkinson's disease.

When employed as thrombin inhibitors, the compounds of the present invention may be administered in an effective amount within the dosage range of about 0.1 to about 500 mg/kg, preferably between 0.1 to 10 mg/kg body weight, on a regimen in single or 2–4 divided daily doses.

When employed as inhibitors of thrombin, the compounds of the present invention may be used in combination with thrombolytic agents such as tissue plasminogen activator, streptokinase, and urokinase. Additionally, the compounds of the present invention may be used in combination with other antithrombotic or anticoagulant drugs such as, but not limited to, fibrinogen antagonists and thromboxane receptor antagonists.

The thrombin inhibitors may also be coupled with soluble polymers as targetable drug carriers. Such polymers can include polyvinylpyrrolidone, pyran copolymer, polyhydroxy-propylmethacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogens.

Human leucocyte elastase is released by polymorphonuclear leukocytes at sites of inflammation and thus is a contributing cause for a number of disease states. Compounds of the present invention are expected to have an anti-inflammatory effect useful in the treatment of gout, rheumatoid arthritis and other inflammatory diseases, and in the treatment of emphysema. The leucocyte elastase inhibitory properties of compounds of the present invention are determined by the method described below. Cathepsin G has also been implicated in the disease states of arthritis, gout and emphysema, and in addition, glomerulonephritis and lung infestations caused by infections in the lung. In their end-use application the enzyme inhibitory properties of the compounds of Formula I is readily ascertained by standard biochemical techniques that are well-known in the art.

The Cathepsin G inhibitory properties of compounds within the scope of the present invention are determined by the following method. A preparation of partially purified human Cathepsin G is obtained by the procedure of Baugh et al., *Biochemistry* 15: 836 (1979). Leukocyte granules are a major source for the preparation of leukocyte elastase and cathepsin G (chymotrypsin-like activity). Leukocytes are lysed and granules are isolated. The leukocyte granules are extracted with 0.20 M sodium acetate, pH 4.0, and extracts are dialyzed against 0.05 M Tris buffer, pH 8.0 containing 0.05 M NaCl overnight at 4° C. A protein fraction precipitates during dialysis and is isolated by centrifugation. This fraction contains most of the chymotrypsin-like activity of leukocyte granules. Specific substrates are prepared for each enzyme, namely N—Suc—Ala—Ala—Pro—Val-p-nitroanilide and Suc—Ala—Ala—Pro—Phe-p-nitroanilide. The latter is not hydrolyzed by leukocyte elastase. Enzyme preparations are assayed in 2.00 mL of 0.10 M Hepes buffer, pH 7.5, containing 0.50 M NaCl, 10% dimethylsulfoxide and 0.0020 M Suc—Ala—Ala—Pro—Phe-p-nitroanilide as a substrate. Hydrolysis of the p-nitroanilide substrate is monitored at 405 nm and at 25° C.

Useful dose range for the application of compounds of the present invention as neutrophil elastase inhibitors and as Cathepsin G inhibitors depend upon the nature and severity of the disease state, as determined by the attending diagnostician, with a range of 0.01 to 10 mg/kg body weight, per day, being useful for the aforementioned disease states.

Compounds of the present invention that inhibit urokinase or plasminogen activator are potentially useful in treating excessive cell growth disease state. As such compounds of the present invention may also be useful in the treatment of benign prostatic hypertrophy and prostatic carcinoma, the treatment of psoriasis, and as abortifacients. For their end-use application, the potency and other biochemical parameters of the enzyme inhibiting characteristics of compounds of the present invention are readily ascertained by standard biochemical techniques well known in the art. Actual dose ranges for this application will depend upon the nature and severity of the disease state of the patient or animal to be treated as determined by the attending diagnostician. It is to be expected that a general dose range will be about 0.01 to 10 mg per kg per day for an effective therapeutic effect.

Additional uses for compounds of the present invention include analysis of commercial reagent enzymes for active site concentration. For example, chymotrypsin is supplied as a standard reagent for use in clinical quantitation of chymotrypsin activity in pancreatic juices and feces. Such assays are diagnostic for gastrointestinal and pancreatic disorders. Pancreatic elastase is also supplied commercially as a reagent for quantitation of $\alpha_1$-antitrypsin in plasma. Plasma $\alpha_1$-antitrypsin increases in concentration during the course of several inflammatory diseases, and $\alpha_1$-antitrypsin deficiencies are associated with increased incidence of lung disease. Compounds of the present invention can be used to enhance the accuracy and reproducibility of these assays by titrametric standardization of the commercial elastase supplied as a reagent. See, U.S. Pat. No. 4,499,082.

Protease activity in certain protein extracts during purification of particular proteins is a recurring problem which can complicate and compromise the results of protein isolation procedures. Certain proteases present in such extracts can be inhibited during purification steps by compounds of the present invention, which bind tightly to various proteolytic enzymes.

The pharmaceutical compositions of the invention can be administered to any animal that can experience the beneficial effects of the compounds of the invention. Foremost among such animals are humans, although the invention is not intended to be so limited.

The pharmaceutical compositions of the present invention can be administered by any means that achieve their intended purpose. For example, administration can be by parenteral, subcutaneous, intravenous, intramuscular, intraperitoneal, transdermal, buccal, or ocular routes. Alternatively, or concurrently, administration can be by the oral route. The dosage administered will be dependent upon the age, health, and weight of the recipient, kind of concurrent treatment, if any, frequency of treatment, and the nature of the effect desired.

In addition to the pharmacologically active compounds, the new pharmaceutical preparations can contain suitable pharmaceutically acceptable carriers comprising excipients and auxiliaries that facilitate processing of the active compounds into preparations that can be used pharmaceutically.

The pharmaceutical preparations of the present invention are manufactured in a manner that is, itself, known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders, such as, starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents can be added, such as, the above-mentioned starches and also carboxymethyl-starch, cross-linked polyvinyl pyrrolidone, agar, or alginic acid or a salt thereof, such as, sodium alginate. Auxiliaries are, above all, flow-regulating agents and lubricants, for example, silica, talc, stearic acid or salts thereof, such as, magnesium stearate or calcium stearate, and/or polyethylene glycol. Dragee cores are provided with suitable coatings that, if desired, are resistant to gastric juices. For this purpose, concentrated saccharide solutions can be used, which may optionally contain gum arabic, talc, polyvinyl pyrrolidone, polyethylene glycol, and/or titanium dioxide, lacquer solutions and suitable organic solvents or solvent mixtures. In order to produce coatings resistant to gastric juices, solutions of suitable cellulose preparations, such as, acetylcellulose phthalate or hydroxypropylmethyl-cellulose phthalate, are used. Dye stuffs or pigments can be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer, such as, glycerol or sorbitol. The push-fit capsules can contain the active compounds in the form of granules that may be mixed with fillers such as lactose, binders such as starches, and/or lubricants such as talc or magnesium stearate and, optionally, stabilizers. In soft capsules, the active compounds are preferably dissolved or suspended in suitable liquids, such as, fatty oils or liquid paraffin. In addition, stabilizers may be added.

Suitable formulations for parenteral administration include aqueous solutions of the active compounds in water-soluble form, for example, water-soluble salts, alkaline solutions and cyclodextrin inclusion complexes. Especially preferred alkaline salts are ammonium salts prepared, for example, with Tris, choline hydroxide, Bis-Tris propane, N-methylglucamine, or arginine. One or more modified or unmodified cyclodextrins can be employed to stabilize and increase the water solubility of compounds of the present invention. Useful cyclodextrins for this purpose are disclosed in U.S. Pat. Nos. 4,727,064, 4,764,604, and 5,024,998.

In addition, suspensions of the active compounds as appropriate oily injection suspensions can be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions can contain substances that increase the viscosity of the suspension, for example, sodium carboxymethyl cellulose, sorbitol, and/or dextran. Optionally, the suspension may also contain stabilizers.

Compounds of Formula I can be labeled with radioactive iodine by using an exchange reaction. Exchange of hot iodine for cold iodine is well known in the art. Alternatively, a radio iodine labeled compound can be prepared from the corresponding bromo compound via a tributylstannyl intermediate. See, U.S. Pat. No. 5,122,361, herein incorporated by reference.

The present invention also includes compositions which are useful for in vivo imaging of thrombi in a mammal, wherein the compositions are comprised of a compound of Formula I complexed with a radioactive atom.

For the compounds of Formula I, suitable radioactive atoms include Co-57, Cu-67, Ga-67, Ga-68, Ru-97, Tc-99m, In-111, In-113m, Hg-197, Au-198, and Pb-203. Some radioactive atoms have superior properties for use in radiochemical imaging techniques. In particular, technetium-99m (Tc-99m) is an ideal radioactive atom for imaging because of its nuclear properties. It is a gamma emitter and has a single photon energy of 140 ke V, a half-life of about 6 hours, and it is readily available from a Mo-99/Tc-99 generator. Rhenium-186 and -188 also have gamma emission which allows it to be imaged. Preferred compositions contain the radioactive atom, Tc-99m.

Compositions of the present invention are conveniently prepared by complexing a compound of Formula I with radioisotopes which are suitable for detection externally. The gamma emitters, indium-111m and technetium-99m, are preferred as radioactive atoms because they are detectable with a gamma camera and have favorable half-lives in vivo.

The compounds of Formula I can be labeled by any of the many techniques known in the art to provide a composition of the present invention. For example, these compounds can be labeled through a chelating agent such as diethylenetriaminepentaacetic acid (DTPA) or metallothionein, both of which can be covalently attached to the compound of Formula I.

In general, the compositions of the present invention containing technetium-99m are prepared by forming an aqueous mixture of technetium-99m and a reducing agent and a water-soluble ligand, and then contacting the mixture with a compound of the present invention represented by Formula I. For example, the imaging compounds of this invention are made by reacting technetium-99m (in an oxidized state) with the compounds of the present invention having a chelating means in the presence of a reducing agent to form a stable complex between technetium-99m in a reduced state (IV or V valence state).

One embodiment of the composition of the present invention is prepared by labeling a compound of Formula I having a DTPA chelating means with technetium-99m. This may be accomplished by combining a predetermined amount (as 5 µg to 0.5 mg) of compound of the present invention with an aqueous solution containing citrate buffer and stannous reducing agent, then adding freshly eluted sodium pertechnetate containing a predetermined level of radioactivity (as 15 mCi). After allowing an incubation of the mixture at room temperature, the reaction mixture is loaded into a shielded syringe through a sterile filter (0.2–0.22 micron), then is dispensed into 0.9% saline for injection, if desired.

Another embodiment of the compositions of the present invention is prepared by labeling a compound of Formula I having a metallothionein chelating means with technetium-99m. This may be accomplished by combining aqueous sodium pertechnetate-99m with aqueous stannous glucoheptonate to form a soluble complex of technetium-99m (in reduced state) with two glucoheptonate molecules, then combining this solution with a compound of the Formula I having a metallothionein attached thereto. After incubating the mixture for a period of time and under conditions which allow for an exchange of the technetium-99m from the glucoheptonate complex to the metallothionein of the compound of Formula I, the technetium-labeled composition of the present invention is formed.

The source of technetium-99m should preferably be water soluble. Preferred sources are alkali and alkaline earth metal pertechnetate ($TcO_4$—). Technetium-99m is most preferably obtained in the form of fresh sodium pertechnetate from a sterile technetium-99m generator (as from a conventional Mo-99/Tc-99m generator). However, any other source of physiologically acceptable technetium-99m may be used.

Reducing agents for use in the method are physiologically acceptable for reducing technetium-99m from its oxidized state to the IV or V valence state or for reducing rhenium from its oxidized state. Reducing agents which can be used are stannous chloride, stannous fluoride, stannous glucoheptonate, stannous tartarate, and sodium dithionite. The preferred agents are stannous reducing agents, especially stannous chloride or stannous glucoheptonate. The amount of reducing agent is that amount necessary to reduce the technetium-99m to provide for the binding to the chelating means of a compound of Formula I in this radioisotope's reduced state. For example, stannous chloride ($SnCl_2$) is the reducing agent and can be used in range from 1–1,000 µg/mL. Especially preferred concentrations are about 30–500 µg/mL.

Citric acid complexes with technetium-99m quickly to form a stable technetium-99m-citrate complex. Upon contact with a compound of Formula I substantially quantitative transfer of technetium-99m from its citrate complex to the chelating means of the compound of Formula I is achieved rapidly and under mild conditions. The amount of citric acid (as sodium citrate) can range from about 0.5 mg/ml up to the amount maximally soluble in the medium. Preferred amounts of citric acid range from 15 to 30 µg/ml.

The amount of compound of Formula I having a chelating means can range from 0.001 to about 3 mg/mL, preferably about 0.017 to about 0.15 mg/mL. Finally, technetium-99m in the form of pertechnetate can be used in amounts of preferably about 1–50 mCi. The amount of mCi per mg of compound of the present invention is preferably about 30–150.

The reaction between the compound of Formula I and the metal ion-transfer ligand complex is preferably carried out in a aqueous solution at a pH at which the compound of Formula I is stable. By "stable", it is meant that the compound remains soluble and retains its inhibitory activity against α-thrombin. Normally, the pH for the reaction will be from about 5 to 9, the preferred pH being above 6–8. The technetium-99m-citrate complex and a compound of Formula I are incubated, preferably at a temperature from about 20° C. to about 60° C., most preferably from about 20° C. to about 37° C., for a sufficient amount of time to allow transfer of the metal ion from the citrate complex to the chelating means of the compound of Formula I. Generally, less than one hour is sufficient to complete the transfer reaction under these conditions.

Alternative compositions of the present invention include an In-111 labeled compound of the present invention.

The present invention also includes compositions of the compounds of the present invention which are useful for in vivo imaging of thrombi in a mammal, comprised of a compound represented by Formula I complexed to a paramagnetic atom.

Preferred paramagnetic atoms are divalent or trivalent ions of elements with an atomic number of 21 to 29, 42, 44 and 58 to 70. Suitable ions include chromium(III), manganese(II), iron(III), iron(II), cobalt(II), nickel(II), copper(II), praseodymium(III), neodymium(III), samarium (III) and ytterbium(III). Because of their very strong magnetic moments, gadolinium(III), terbium(III), dysoprosium (III), holmium(III), and erbium(III) are preferred. Especially preferred for the paramagnetic atom is gadolinium(III).

The compositions of the present invention may be prepared by combining a compound of Formula I with a paramagnetic atom. For example, the metal oxide or a metal salt (for example, nitrate, chloride or sulfate) of a suitable paramagnetic atom is dissolved or suspended in a medium comprised of water and an alcohol, such as methyl, ethyl or isopropyl alcohol. This mixture is added to a solution of an equimolar amount of the compound of Formula I in a similar aqueous medium and stirred. The reaction mixture may be heated moderately until the reaction is completed. Insoluble compositions formed may be isolated by filtering, while soluble compositions may be isolated by evaporation of the solvent. If acid groups on the chelating means are still present in the composition of the present invention, inorganic or organic bases, and even amino acids, may be added to convert the acidic complex into a neutral complex to facilitate isolation or purification of homogenous composition. Organic bases or basic amino acids may be used as neutralizing agents, as well as inorganic bases such as hydroxides, carbonates or bicarbonates of sodium, potassium or lithium.

The present invention also include diagnostic compositions which are useful for in vivo imaging of thrombi in a mammal, comprising a pharmaceutically acceptable carrier and a diagnostically effective amount of compositions derived from the compounds of Formula I.

The "diagnostically effective amount" of the composition required as a dose will depend on the route of administration, the type of mammal being treated, and the physical characteristics of the specific mammal under consideration. These factors and their relationship to determining this dose are well known to skilled practitioners in the medial diagnostic arts. Also, the diagnostically effective amount and method of administration can be tailored to achieve optimal efficacy but will depend on such factors as weight, diet, concurrent medication and other factors which those skilled in the medical arts will recognize. In any regard, the dose for imaging should be sufficient for detecting the presence of the imaging agent at the site of a thrombus in question. Typically, radiologic imaging will require that the dose provided by the pharmaceutical composition position of the present invention be about 5 to 20 $\mu$Ci, preferably about 10 $\mu$Ci. Magnetic resonance imaging will require that the dose provided be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

"Pharmaceutically acceptable carriers" for in vivo use are well known in the pharmaceutical art, and are described, for example, in Remington's Pharmaceutical Sciences, Mack Publishing Co. (A. R. Gennaro edit. 1985). The pharmaceutical compositions of the present invention may be formulated with a pharmaceutically acceptable carrier to provide sterile solutions or suspensions for injectable administration. In particular, injectables can be prepared in conventional forms, either as liquid solutions or suspensions, solid forms suitable for solution or suspensions in liquid prior to injection, or as emulsions. Suitable excipients are, for example, water, saline, dextrose, mannitol, lactose, lecithin, albumin, sodium glutamate, cysteine hydrochloride, or the like. In addition, if desired, the injectable pharmaceutical compositions may contain minor amounts of nontoxic auxiliary substances, such as wetting agents, pH buffering agents, and the like. If desired, absorption enhancing preparations (e.g., liposomes) may be utilized.

The present invention also encompasses diagnostic compositions prepared for storage or administration. These would additionally contain preservatives, stabilizers and dyes. For example, sodium benzoate, sorbic acid and esters of p-hydroxybenzoic acid may be added as preservatives. Id. at 1449. In addition, antioxidants and suspending agents may be used.

The in vivo imaging methods of the present invention also offer several advantages over previous imaging techniques for the detection or monitoring of the presence, size, regression or increase of a thrombus. In particular, the present invention provides compounds, compositions and diagnostic compositions have been designed to bind extremely tightly to the thrombin associated with a thrombus and thereby reduce "background" due to circulating radioactivity or paramagnetism arising from unbound imaging agent. Furthermore, in vivo imaging by intracoronary injection of the compounds, compositions or diagnostic compositions of the present invention, is expected to be almost instantaneous since these imaging agents would saturate the thrombin bound to the thrombus immediately.

Accordingly, the present invention also includes methods for in vivo imaging of a thrombus in a mammal, comprising the steps of: (1) administering to a mammal a diagnostically acceptable amount of a compound, composition, or diagnostic composition of the present invention and (2) detecting a thrombus in a blood vessel.

The term "in vivo imaging" as used herein relates to methods of the detection of a thrombus in a mammal, as well as the monitoring of the size, location and number of thrombi in a mammal, as well as dissolution or growth of the thrombus.

In employing the compounds, compositions or diagnostic compositions in vivo by this method, "administering" is accomplished parenterally, in either a systemic or local targeted manner. Systemic administration is accomplished by injecting the compounds, compositions by diagnostic compositions of the present invention into a convenient and accessible vein or artery. This includes but is not limited to administration by the ankecubutal vein. Local targeted administration is accomplished by injecting the compounds, compositions or diagnostic compositions of the present invention proximal in flow to a vein or artery suspected to contain thrombi distal to the injection site. This includes but is not limited to direct injection into the coronary arterial vasculature to image coronary thrombi, into the carotid artery to image thrombi in the cerebral vasculature, or into a pedal vein to image deep vein thrombosis of the leg.

Also, the manner of delivery of a composition of the present invention to the site of a thrombus is considered within the scope of the term "administering". For example, a compound represented by Formula I having a chelating means attached thereto may be injected into the mammal, followed at a later time by the radioactive atom thereby forming in vivo at the site of the thrombus the composition comprising the compound of formula complexed to radioactive atom. Alternatively, a composition comprising the compound of formula complexed to radioactive atom may be injected into the mammal.

The "diagnostically effective amount" of the compounds, compositions or diagnostic compositions used in the methods of the present invention will, as previously mentioned, depend on the route of administration, the type of mammal being treated, and the physical characteristics of the specific mammal under treatment. These factors and their relationship to determining this dose are well known to skilled practitioners in the medical diagnostic arts. In any regard, the dose for in vivo imaging should be sufficient for detecting the presence of the imaging agent at the site of a thrombus in question. Typically, radiologic imaging will require that the dose provided by the diagnostic composition of the present invention be about 5 to 20 $\mu$Ci, preferably about 10 $\mu$Ci. Magnetic resonance imaging will require that the dose provided by the diagnostic composition be about 0.001 to 5 mmole/kg, preferably about 0.005 to 0.5 mmole/kg of a compound of Formula I complexed with paramagnetic atom. In either case, it is known in the art that the actual dose will depend on the location of the thrombus.

The detecting of a thrombus by imaging is made possible by the presence of radioactive or paramagnetic atoms localized at such thrombus.

The radioactive atoms associated with the compositions and diagnostic compositions of the present invention are preferably imaged using a radiation detection means capable of detecting gamma radiation, such as a gamma camera or the like. Typically, radiation imaging cameras employ a conversion medium (wherein the high energy gamma ray is absorbed, displacing an electron which emits a photon upon its return to the orbital state), photoelectric detectors arranged in a spatial detection chamber (to determine the position of the emitted photons), and circuitry to analyze the photons detected in the chamber and produce an image.

The paramagnetic atoms associated with the compositions and diagnostic compositions of the present invention are detected in magnetic resonance imaging (MRI) systems. In such systems, a strong magnetic field is used to align the nuclear spin vectors of the atoms in a patient's body. The field is disturbed by the presence of paramagnetic atoms localized at a thrombus and an image of the patient is read as the nuclei return to their equilibrium alignments.

The following examples are illustrative, but not limiting, of the method and compositions of the present invention. Other suitable modifications and adaptations of the variety of conditions and parameters normally encountered and obvious to those skilled in the art are within the spirit and scope of the invention.

EXAMPLE 1

1-{N-[2-(amidinoaminooxy)ethyl]amino}carbonylmethyl-6-methyl-3-(phenethylamino)-pyrazinone trifluoroacetate

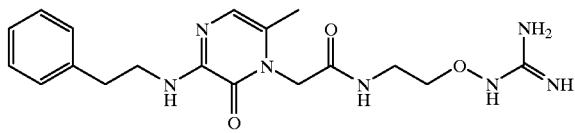

a. N-[2-(Benzyloxycarbonylamino)ethoxy]phthalimide

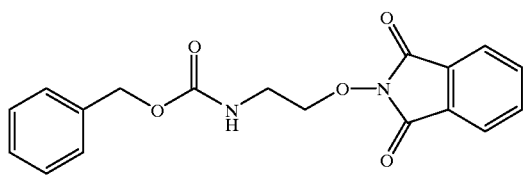

To a solution of benzyl N-(2-hydroxyethyl)carbamate (5.9 g, 30 mmol), N-hydroxyphthalimide (4.9 g, 30 mmol), and triphenylphosphine (7.9 g, 30 mmol) in tetrahydrofuran (100 mL) was added diethyl azodicarboxylate (5.2 g, 30 mmol). The reaction mixture was stirred at room temperature overnight. Ethyl acetate (200 mL) was added, washed with saturate NaHCO$_3$ (2×100 mL) and brine (100 mL), dried over Na$_2$SO$_4$, and filtered. After evaporating the filtrate, the residue was purified by flash column chromatography (methylene chloride to 4% ethyl acetate in methylene chloride) to give the title compound as a white solid (9.3 g, 91%). $^1$H-NMR (300 MHz, CDCl$_3$) $\delta$ 7.84 (m, 2H), 7.78 (m, 2H), 7.37 (m, 5H), 5.97 (br s, 1H), 5.14 (s, 2H), 4.27 (t, J=4.9 Hz, 2H), 3.51 (q, J=5.2 Hz, 2H).

b. 2-(Benzyloxycarbonylamino)ethoxyamine

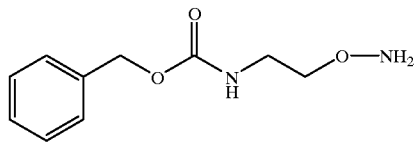

To a solution of N-[2-(benzyloxycarbonylamino)ethoxy]phthalimide (1.36 g, 4.0 mmol), as prepared in the preceding step, in ethanol (20 mL) and tetrahydrofuran (20 mL) was added 40% methylamine (2.0 mL, 25 mmol) and stirred at room temperature for 1 h. After evaporating the solvent, the residue was passed through silica gel (3:1 ethyl acetate:hexane to ethyl acetate) to give the title compound as a white solid (800 mg, 95%). $^1$H-NMR (300 MHz, CDCl$_3$) $\delta$ 7.36 (m, 5H), 5.47 (br s, 2H), 5.21 (br s, 1H), 5.10 (s, 2H), 3.72 (t, J=5.0 Hz, 2H), 3.44 (q, J=5.0 Hz, 2H).

c. [N,N'-Di(tert-butoxycarbonyl)]2-(benzyloxycarbonylamino) ethoxyguanidine

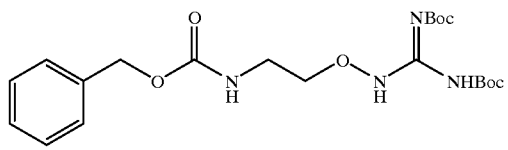

To a solution of 2-(benzyloxycarbonylamino) ethoxyamine (780 mg, 3.7 mmol), as prepared in the preceding step, in N,N-dimethylformamide (20 mL) was added [N,N'-di(tert-butoxycarbonyl)] amidinopyrazole (1.25 g, 4.0 mmol). The mixture was stirred at room temperature overnight, and the solvent evaporated under high vacuum. The residue was purified by flash column chromatography (0–5% ethyl acetate in methylene chloride) to give the title compound as a colorless oil (1.55 g, 93%). $^1$H-NMR (300 MHz, CDCl$_3$) $\delta$ 9.08 (s, 1H), 7.67 (s, 1H), 7.33 (m, 5H), 6.21 (br s, 1H), 5.21 (br s, 1H), 5.11 (s, 2H), 4.12 (t, J=4.8 Hz, 2H), 3.54 (q, J=4.9 Hz, 2H), 1.49 (s, 9H), 1.46 (s, 9H).

d. [N,N'-Di(tert-butoxycarbonyl)]2-aminoethoxyguanidine

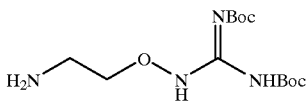

A mixture of [N,N'-di(tert-butoxycarbonyl)]2-(benzyloxycarbonylamino) ethoxyguanidine (730 mg, 1.5 mmol), as prepared in the preceding step, 10% palladium on carbon (70 mg) in ethanol (20 mL) and tetrahydrofuran (20 mL) was hydrogenated under hydrogen (balloon) for 30 min. The catalysts were removed by filtration through Celite and the filtrate was concentrated in vacuo. The residue was purified on a Waters Sep-Pak (10 g, 95:5 methylene chloride:methanol saturated with ammonia) to give the title compound as a colorless oil (290 mg, 61%). $^1$H-NMR (300 MHz, CDCl$_3$) $\delta$ 9.08 (br s, 1H), 4.08 (t, J=5.2 Hz, 2H), 2.99 (q, J =5.1 Hz, 2H), 1.50 (s, 9H), 1.48 (s, 9H).

e. Benzyl-N-(1-cyanoethyl)glycine hydrochloride

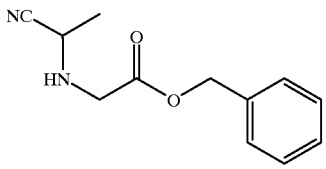

Trimethylsilyl cyanide (TMSCN) (4.0 mL, 30 mmol) was added cautiously to a stirred solution of benzyl glycine free base (5.0 g, 30 mmol) and acetaldehyde (1.7 mL, 30 mmol) in methylene chloride (15 mL) under argon atmosphere. After 15 h, the volatile components were removed in vacuo, and the residue was dissolved in ethyl acetate (200 mL), washed with brine (100 mL), dried ($Na_2SO_4$) and evaporated to an oil. The oil was redissolved in ether (30 mL) and ethanol (30 mL), and 1M HCl in ether (33 mL) was added dropwise to give the title compound (6.60 g, 100%) as an off-white crystalline precipitate. mp: 137–138° C.; $^1$H-NMR (300 MHz, $CD_3OD$) δ 7.31–7.48 (m, 5H), 5.32 (s, 2H), 4.68 (q, J=7.0 Hz, 1H), 4.22 (s, 2H), 1.73 (d, J=7.1 Hz, 3H); CI MS m/z=192 (M+H). Anal. Calcd. for $C_{12}H_{14}N_2O_2$. HCl: C, 56.49; H, 5.95; N, 11.00. Found: C, 56.32; H, 5.88, N, 10.89.

f. 1-Benzyloxycarbonylmethyl-3,5-dichloro-6-methylpyrazinone

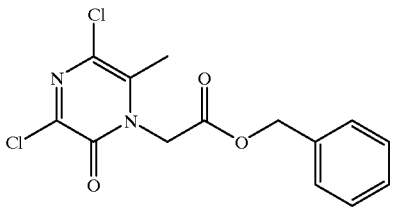

A stirred mixture of oxalyl chloride (5.3 mL, 60 mmol) and benzyl-N-(1-cyanoethyl)glycine hydrochloride (3.82 g, 15 mmol), as prepared in the preceding step, in 1,2-dichlorobenzene (30 mL) was heated to 100° C. overnight. The solvent was evaporated in vacuo and the residue was purified by flash column chromatography (20–30% ethyl acetate in hexane) to give a solid. 10% Ethyl acetate in hexane (100 mL) was added and the solid was collected to give the title compound as an orange crystalline solid (2.7 g, 55%). $^1$H-NMR (300 MHz, $CDCl_3$) δ 7.38 (m, 5H), 5.24 (s, 2H), 4.89 (s, 2H), 2.34 (S, 3H).

g. 3-(2-Phenethylamino)-5-chloro-6-methyl-1-(benzyloxycarbonylmethyl)-pyrazinone

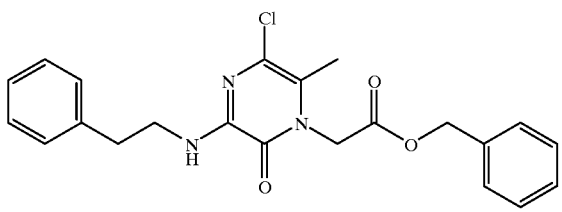

Phenethylamine (1.5 mL, 12 mmol) was added to a stirred solution of 1-benzyloxycarbonylmethyl-3,5-dichloro-6-methylpyrazinone (1.31 g, 4.0 mmol), as prepared in the preceding step, in ethyl acetate (10 mL) and the resulting mixture was heated to reflux under nitrogen. After 2 h, the reaction mixture was cooled, diluted with methylene chloride (100 mL), washed with 5% citric acid (2×50 mL), brine (50 mL), dried ($Na_2SO_4$) and filtered. After evaporating the filtrate in vacuo, the solid was collected and washed with 20% ethyl acetate in hexane to give the title compound as a crystalline solid (1.5 g, 91%). $^1$H-NMR (300 MHz, $CDCl_3$) δ 7.22–7.38 (m, 10 H), 6.11 (t, J=5.8 Hz, 1H), 5.21 (s, 2H), 4.79 (s, 2H), 3.68 (q, J=7.0 Hz, 2H), 2.93 (t, J=7.0 Hz, 2H), 2.22 (s, 3H).

h. Mixture of 3-(2-phenethylamino)-6-methyl-1-carboxymethylpyrazinone and 3-(2-phenethylamino)-5-chloro-6-methyl-1-carboxymethylpyrazinone

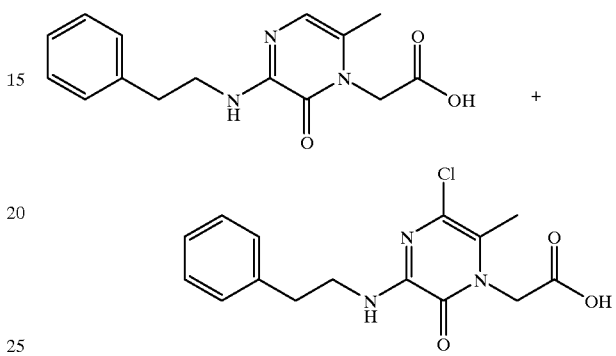

A mixture of 3-(2-phenethylamino)-5-chloro-6-methyl-1-(benzyloxycarbonylmethyl)-pyrazinone (412 mg, 1.0 mmol), as prepared in the preceding step, and palladium on carbon (10%, 100 mg) in tetrahydrofuran (10 mL) and ethanol (40 mL) was stirred under hydrogen (balloon) for two days. The reaction was filtered through Celite, the frit was washed with ethanol, and filtrate was evaporated in vacuo to give a mixture of 3-(2-phenethylamino)-6-methyl-1-carboxymethylpyrazinone and 3-(2-phenethylamino)-5-chloro-6-methyl-1-carboxymethylpyrazinone as a slightly red solid (210 mg) that was directly used in the next step without further purification.

i. 1-{N-[2-(N',N"-Bis(tert-butoxycarbonyl)amidinoaminooxy)ethyl]amino}carbonylmethyl-6-methyl-3-(phenethylamino)-pyrazinone and 1-{N-[2-(N',N"-bis(tert-butoxycarbonyl)amidinoaminooxy)ethyl]amino}carbonylmethyl-5-chloro-6-methyl-3-(phenethylamino)-pyrazinone

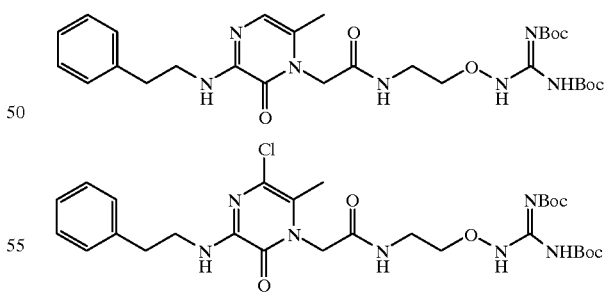

To a solution of the mixture of 3-(2-phenethylamino)-6-methyl-1-carboxymethylpyrazinone and 3-(2-phenethylamino)-5-chloro-6-methyl-1-carboxymethylpyrazinone (200 mg), as prepared in the preceding step, [N,N'-di(tert-butoxycarbonyl)]2-aminoethoxyguanidine (225 mg, 0.7 mmol), as prepared in step d of Example 1, di-isopropylethylamine (180 μL, 1.0 mmol) in N,N-dimethylformamide (10 mL) was added Castro's reagent (BOP) (442 mg, 1.0 mmol). The mixture was stirred at room temperature overnight, the solvent was removed under high vacuum, and the residue was dissolved in methylene chloride (100 mL), washed with 10% citric acid (2×50 mL) and brine (50 mL), and dried over Na$_2$SO$_4$. After evaporating the solvent in vacuo, the residue was purified by column chromatography (2:1 to 3:1 ethyl acetate:hexane) to give 1-{N-[2-(N',N''-bis(tert-butoxycarbonyl)amidinoaminooxy)ethyl]amino}carbonylmethyl-5-chloro-6-methyl-3-(phenethylamino)-pyrazinone as a colorless foam (100 mg, 23%). $^1$H-NMR (300 MHz, CDCl$_3$/CD$_3$OD) δ 8.42 (t, J=4.8 Hz, 1H), 7.26 (m, 5H), 6.68 (s, 1H), 4.75 (s, 2H), 4.11 (t, J=4.6Hz, 2H), 3.60 (m 4H), 2.91 (m, 2H), 2.15 (s, 3H), 1.52 (s, 9H), 1.49 (s, 9H). Also isolated was 1-{N-[2-(N',N''-bis(tert-butoxycarbonyl)amidinoaminooxy)ethyl]amino}carbonylmethyl-6-methyl-3-(phenethylamino)-pyrazinone as a colorless foam (130 mg, 32%). $^1$H-NMR (300 MHz, CDCl$_3$/CD$_3$OD) δ 8.47 (t, J=4.9 Hz, 1H), 7.44–7.87 (m,3H), 7.25 (m, 5H), 4.80 (s, 2H), 4.11 (mn, 2H), 3.65 (t, J=7.0 Hz, 2H), 3.59 (m, 2H), 2.93 (t, J=7.1 Hz, 2H), 2.28 (s, 3H), 1.52 (s, 9H), 1.48 (s, 9H).

j. 1-{N-[2-(Amidinoaminooxy)ethyl]amino}carbonylmethyl-6-methyl-3-(phenethylamino)-pyrazinone trifluoroacetate

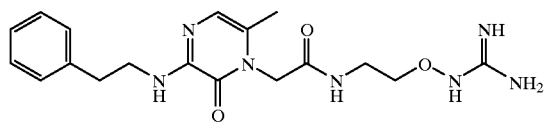

A mixture of 1-{N-[2-(N',N''-bis(tert-butoxycarbonyl)amidinoaminooxy)ethyl]amino}carbonylmethyl-6-methyl-3-(phenethylamino)-pyrazinone (120 mg, 0.2 mmol), as prepared in the preceding step, and trifluoroacetic acid (2 mL) in methylene chloride (4 mL) was stirred at room temperature for 1 h. After evaporatimg the solvent in vacuo, the residue was purified on a Waters Sep-Pak (5 g, 10% methanol in methylene chloride) to give the title compound as a white solid (90 mg, 89%). $^1$H-NMR (300 MHz, DMSO-d$_6$) δ 10.95 (s, 1H), 8.44 (t, J=5.6 Hz, 1H), 7.73 (br s,4H), 7.20–7.30 (m, 6H), 6.67 (s, 1H), 4.61 (s, 2H), 3.81 (t, J=5.4 Hz, 2H), 3.50 (q, J=6.7Hz, 2H), 3.39 (q, J=5.4 Hz, 2H), 2.86 (t, J=6.9 Hz, 2H), 2.07 (s, 3H). Mass spectrum (MALDI-TOF, α-cyano-4-hydroxycinnamic acid matrix) Calcd. for C$_{18}$H$_{25}$N$_7$O$_3$: 388.2 (M+H), 410.2 (M+Na); Found: 388.3, 410.4.

EXAMPLE 2
1-{N-[2-(amidinoaminooxy)ethyl]amino}carbonylmethyl-5-chloro-6-methyl-3-(phenethylamino)-pyrazinone trifluoroacetate

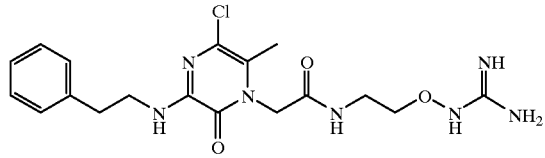

The title compound was prepared from 1-{N-[2-(N',N''-bis(tert-butoxycarbonyl)amidinoaminooxy) ethyl]amino}carbonylmethyl-5-chlor o-6-methyl-3-(phenethylamino)-pyrazinone, as prepared in the step i of Example 1, using the procedure of Example 1, step j. $^1$H-NMR (300 MHz, DMSO-d$_6$) δ 10.96 (s, 1H), 8.46 (br s, 1H), 7.73 (br s, 4H), 7.42 (t, J=5.3 Hz, 1H), 7.18–7.33 (m, 5H), 4.66 (s, 2H), 3.81 (br s, 2H), 3.49 (m, 2H), 3.36 (m, 2H), 2.86 (t, J=7.2 Hz, 2H), 2.18 (s, 3H). Mass spectrum(MALDI-TOF, α-cyano-4-hydroxycinnamic acid matrix) Calcd. for C$_{18}$H$_{24}$ClN$_7$O$_3$: 422.2 (M+H), 444.2 (M+Na); Found: 422.1, 444.0.

EXAMPLE 3

1-{N-[2-(amidinoaminooxy)ethyl]amino}carbonylmethyl-6-methyl-3-(2,2-diphenylethylamino)-pyrazinone trifluoroacetate

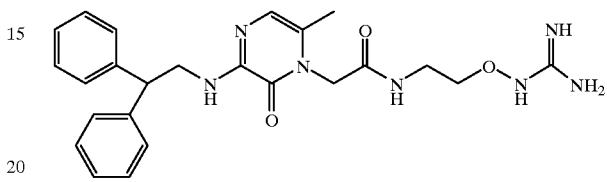

The title compound was prepared from 1-benzyloxycarbonylmethyl-3,5-dichloro-6-methylpyrazinone, as prepared in the step f of Example 1, and 2,2-diphenylethylamine using the procedures of Example 1, steps g–j. $^1$H-NMR (300 MHz, DMSO-d$_6$) δ 10.89 (br s, 1H), 8.42 (t, J=5.5 Hz, 1H), 7.70 (br s, 4H), 7.17–7.31 (m, 10H), 6.74 (br s, 1H), 6.69 (s, 1H), 4.57 (s, 2H), 4.48 (t, J=7.8 Hz, 2H), 3.91 (t, J=6.6 Hz, 2H), 3.79 (t, J=5.4 Hz, 2H), 3.36 (t, J=5.4 Hz, 2H), 2.06 (s, 3H). Mass spectrum (MALDI-TOF, α-cyano-4-hydroxycinnamic acid matrix) Calcd. for C$_{24}$H$_{29}$N$_7$O$_3$: 464.3 (M+H), 486.2 (M+Na); Found: 464.3, 486.3.

EXAMPLE 4

1-{N-[2-(amidinoaminooxy)ethyl]amino}carbonylmethyl-5-chloro-6-methyl-3-(2,2-diphenylethylamino)-pyrazinone trifluoroacetate

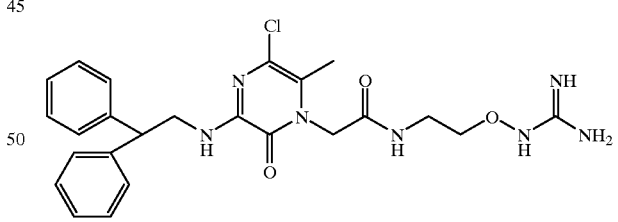

The title compound was prepared from 1-benzyloxycarbonylmethyl-3,5-dichloro-6-methylpyrazinone, as prepared in the step f of Example 1, and 2,2-diphenylethylamine using the procedures of Example 1, steps g–j. $^1$H-NMR (300 MHz, DMSO-d$_6$) δ 10.90 (br s, 1H), 8.41 (br s, 1H), 7.71 (br s, 4H), 7.18–7.32 (m, 10H), 4.63 (s, 2H), 4.52 (t, J=7.7 Hz, 2H), 3.89 (t, J=6.3Hz, 2H), 3.79 (t, J=5.3 Hz, 2H), 3.37 (t, J=5.3 Hz, 2H), 2.17 (s, 3H). Mass spectrum (MALDI-TOF, α-cyano-4-hydroxycinnamic acid matrix) Calcd. for C$_{24}$H$_{28}$ClN$_7$O$_3$: 498.2 (M+H), 520.2 (M+Na); Found: 498.2, 520.2.

EXAMPLE 5
1-{N-[2-(amidinoaminooxy)ethyl]amino}carbonylmethyl-6-methyl-3-(4-methylphenethylamino)-pyrazinone trifluoroacetate

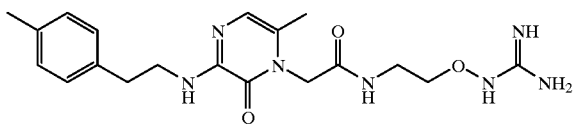

The title compound was prepared from 1-benzyloxycarbonylmethyl-3,5-dichloro-6-methylpyrazinone, as prepared in the step f of Example 1, and 4-methylphenethylamine using the procedures of Example 1, steps g–j. $^1$H-NMR (300 MHz, DMSO-$d_6$) δ 10.92 (s, 1H), 8.44 (t, J=5.6 Hz, 1H), 7.71 (br s, 4H), 7.11 (s, 4H), 6.67 (s, 1H), 4.61 (s, 2H), 3.81 (t, J=5.4 Hz, 2H), 3.50 (m, 2H), 3.38 (i, 2H), 2.81 (t, J=6.9 Hz, 2H), 2.27 (s, 3H), 2.07 (s, 3H). Mass spectrum (MALDI-TOF, α-cyano-4-hydroxycinnamic acid matrix) Calcd. for $C_{19}H_{27}N_7O_3$: 402.2 (M+H), 424.2 (M+Na); Found: 402.1, 424.2.

EXAMPLE 6
1-{N-[2-(amidinoaminooxy)ethyl]amino}carbonylmethyl-6-methyl-3-(4-methoxyphenethylamino)-pyrazinone trifluoroacetate

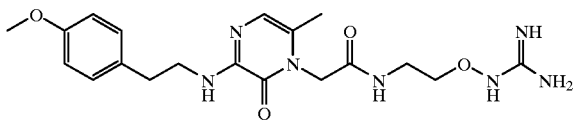

The title compound was prepared from 1-benzyloxycarbonylmethyl-3,5-dichloro-6-methylpyrazinone, as prepared in the step f of Example 1, and 4-methoxyphenethylamine using the procedures of Example 1, steps g–j. $^1$H-NMR (300 MHz, DMSO-$d_6$) δ 10.88 (s, 1H), 8.42 (t, J=5.5 Hz, 1H), 7.68 (br s, 4H), 7.15 (d, J=8.6Hz, 2H), 6.85 (d, J=8.7 Hz, 2H), 6.67 (s, 1H), 4.61 (s, 2H), 3.81 (t, J=5.3 Hz, 2H), 3.72 (s, 3H), 3.50 (m, 2H), 3.38 (m, 2H), 2.79 (t, J=6.9 Hz, 2H), 2.07 (s, 3H). Mass spectrum(MALDI-TOF, α-cyano-4-hydroxycinnamic acid matrix) Calcd. for $C_{19}H_{27}N_7O_4$: 418.2 (M+H), 440.2 (M+Na); Found: 418.3, 440.4.

EXAMPLE 7
1-{N-[2-(amidinoaminooxy)ethyl]amino}carbonylmethyl-6-methyl-3-(1-phenylcyclobutyl) methylamino-pyrazinone trifluoroacetate

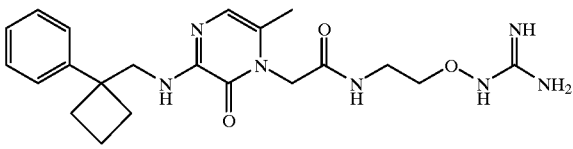

a. (1-Phenylcyclobutyl)methylamine

To a solution of 1-phenylcyclobutanecarbonitrile (0.96 g, 6.09 mmol) in anhydrous tetrahydrofuran (40 mL) was added a 1 N solution of lithium aluminum hydride (LAH) in tetrahydrofuran (12 mL, 12 mmol). After stirring 2 h at ambient temperature, the excess LAH was slowly quenched with water (10 mL) and diluted with additional tetrahydrofuran (20 mL). This was then reacted with 0.25 N aqueous NaOH (5 mL) at ambient temperature for 20 h and filtered, the filtrate concentrated in vacuo, and the residue purified by flash column chromatography (10% methanol in dichloromethane, saturated with ammonia gas) giving the title compound as a yellow oil (0.52 g, 53%). $^1$H NMR (300 MHz, CDCl$_3$) δ 7.32 (m, 2H), 7.19 (m, 1H), 7.10 (m, 2H), 2.93 (s, 2H), 2.38–2.26 (m, 2H), 2.18–2.01 (m, 3H), 1.92–1.82 (m, 1H), 1.14 (bs, 2H).

b. 3-(1-Phenylcyclobutyl)methylamino-5-chloro-6-methyl-1-(benzyloxycarbonylmethyl) pyrazinone A solution of the product of the preceding step (0.52 g, 3.21 mmol) and 1-benzyloxycarbonylmethyl-3,5-dichloro-6-methylpyrazinone (0.36 g, 1.08 mmol), as prepared in step f of Example 1, in ethyl acetate (15 mL) was refluxed for 3 h and the solvent removed in vacuo. The residue was dissolved in dichloromethane, washed with 10% aqueous citric acid and brine, dried over Na$_2$SO$_4$, and filtered. The evaporated filtrate was then purified by flash column chromatography (20% ethyl acetate in hexanes) giving the title compound as a yellow oil (0.35 g, 71%). $^1$H NMR (300MHz, CDCl$_3$) δ 7.32 (m, 7H), 7.17 (m, 3H), 5.86 (t, 1H, J=5.5 Hz), 5.17 (s, 2H), 4.73 (s, 2H), 3.72 (d, 2H, J=5.7 Hz), 2.35 (m, 2H), 2.22 (m, 2H), 2.17 (s, 3H), 1.89 (m, 1H).

c. 3-(1-Phenylcyclobutyl)methylamino-6-methyl-1-carboxymethyl-pyrazinone

The product of the preceding step (0.33 g, 0.74 mmol), 10% palldium(0) on carbon (0.13 g), and solid potassium hydroxide (0.2 g, 3.6 mmol) were dissolved in 1:1:1 mixture of methanol, water, and tetrahydrofuran (60 mL), degassed by bubbling with nitrogen and putting under aspirator pressure, then stirred under a hydrogen balloon at ambient temperature. After 24 h the reaction was filtered over Celite, the filtrate evaporated, and the residue partially purified by flash column chromatography (20% methanol in dichloromethane) giving the title compound (0.16 g, 65%) as a solid that was used without further purification.

d. 1-{N-[2-(N',N"-Bis{tert-butoxycarbonyl}amidinoaminooxy)ethyl]amino}carbonylmethyl-6-methyl-3-(1-phenylcyclobutyl)methylamino-pyrazinone The product of the preceding step (0.16 g, 0.48 mmol), Castro's reagent (0.24 g, 0.54 mmol), and [N,N'-di(tert-butoxycarbonyl)]-2-aminoethoxyguanidine (0.16 g, 0.52 mmol), as prepared in step d of Example 1, were dissolved in N,N-dimethylformamide (10 mL) and reacted with triethylamine (0.25 mL, 1.80 mmol) at ambient temperature. After 24 h the solvent was removed in vacuo, the residue dissolved in dichloromethane, and the solution washed with 10% aqueous citric acid, saturated NaHCO$_3$, and brine, dried over Na$_2$SO$_4$, and filtered. The evaporated filtrate was purified by flash column chromatography (33% ethyl acetate in dichloromethane) giving the title compound as a clear solid (0.11 g, 37%). $^1$H NMR (300 MHz, CDCl$_3$) δ 9.15 (s, 1H), 8.36 (t, 1H, J=5 Hz), 7.57 (s, 1H), 7.32 (m, 2H), 7.18 (m, 3H), 6.66 (s, 1H), 5.77 (i, 1H), 4.72 (s, 2H), 4.11 (m, 2H), 3.71 (d, 2H, J=5.7 Hz), 3.60 (dd, 2H, J=8.8 Hz, 5.0 Hz), 2.36 (m, 2H), 2.26 (m, 3H), 2.12 (s, 3H), 1.90 (m, 1H), 1.51 (s, 9H), 1.46 (s, 9H). Mass spectrum (MALDI-TOF, α-cyano-4-hydroxycinnamic acid matrix) calcd. for $C_{31}H_{45}N_7O_7$: 428.2 (M-2 Boc+H). Found: 428.9.

e. 1-{N-[2-(Amidinoaminooxy)ethyl]amino}carbonylmethyl-6-methyl-3-(1-phenylcyclobutyl)methylamino-pyrazinone trifluoroacetate The product of the preceding step (0.10 g, 0.17 mmol) was dissolved in dichloromethane (5 mL) and reacted with trifluoroacetic acid (2 mL) at ambient temperature. After 6 h the volatiles were removed in vacuo and the residue purified on a Waters silica Sep-Pak (gradient elution: 10–20% methanol in dichloromethane) giving the title compound as a hygroscopic light yellow solid (0.10 g, 100%). $^1$H NMR (300 MHz, CDCl$_3$/CD$_3$OD) δ 7.33 (m, 2H), 7.19 (m, 3H), 6.56 (d, 1H, J=1.0Hz), 4.65 (s, 2H), 3.94 (t, 2H, J=5Hz), 3.75 (s, 2H), 3.48 (t, 2H, J=5 Hz), 2.43 (m, 2H), 2.25 (m, 3H), 2.12 (s, 3H), 1.93 (m, 1H). Mass spectrum (MALDI-TOF, gentisic acid matrix) calcd. for C$_{21}$H$_{29}$N$_7$O$_3$: 428.2 (M+H), 450.2 (M+Na). Found: 428.8, 450.7.

EXAMPLE 8
1-{N-[2-(amidinoaminooxy)ethyl]amino}carbonylmethyl-6-methyl-3-[2-(1-naphthalene) ethyl]amino-pyrazinone hydrochloride

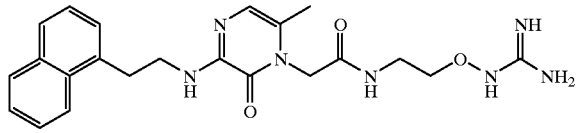

a. 2-(1-Naphthaleneethyl)phthalimide

A solution of 1-naphthaleneethanol (2.51 g, 14.6 mmol), triphenylphosphine (4.57 g, 17.4 mmol), and phthalimide (2.37 g, 16.1 mmol) in tetrahydrofuran (120 mL) was reacted with diethylazodicarboxylate (2.80 mL, 17.8 mmol) at ambient temperature for 2 h. The evaporated product was washed with diethyl ether and dried in a vacuum dessicator overnight giving the title compound (4.34 g, 99%) as an ivory solid. $^1$H NMR (300 MHz, CDCl$_3$) δ 8.31 (d, 1H, J=8.5 Hz), 7.86 (m, 3H), 7.74 (m, 3H), 7.60 (ddd, 1H, J=8.4 Hz, 6.9 Hz, 1.5 Hz), 7.50 (ddd, 1H, J=8.0 Hz, 6.9 Hz, 1.2 Hz), 7.41 (m, 2H), 4.04 (m, 2H), 3.44 (m, 2H).

b. 2-(1-Naphthalene)ethylamine

The product of the preceding step (4.30 g, 14.3 mmol) was dissolved in methanol (30 mL) and reacted with 40% aqueous methylamine (20 mL) at 70° C. for 20 h. The reaction was concentrated in vacuo, the residue dissolved in dichloromethane, and the resulting solution extracted with 10% aqueous HCl and water. The aqueous layer was basified with solid KOH and the resulting solution extracted with dichloromethane. The latter organic layer was washed with brine, dried over Na$_2$SO$_4$, filtered, and the filtrate evaporated giving the title compound as a brown oil (0.83 g, 34%). $^1$H NMR (300 MHz, CDCl$_3$) δ 8.06 (m, 1H), 7.87 (m, 1H), 7.74 (d, 1H, J=8.0 Hz), 7.50 (m, 2H), 7.37 (m, 2H), 3.23 (t, 2H, J=6.6 Hz), 3.11 (t, 2H, J=6.6 Hz).

c. 3-[2-(1-Naphthalene)ethyl]amino-5-chloro-6-methyl-1-(benzyloxycarbonylmethyl) pyrazinone A solution of the product of the preceding step (0.82 g, 4.76 mmol), triethylamine (2.0 mL, 14 mmol), and 1-benzyloxycarbonylmethyl-3,5-dichloro-6-methylpyrazinone (1.05 g, 3.21 mmol), as prepared in step f of Example 1, in ethyl acetate (80 mL) was refluxed for 20 h. After evaporation, the residue was dissolved in dichloromethane and washed with 10% aqueous citric acid, saturated NaHCO$_3$, and brine, dried over Na$_2$SO$_4$, and filtered. The filtrate was then evaporated in vacuo giving the title compound as a tan solid (1.49 g, 68%). $^1$H NMR (300 MHz, CDCl$_3$)δ 8.33 (d, 1H, J=8.6 Hz), 7.86 (dd, 1H, J=8 Hz, 1 Hz), 7.75 (d, 1H, J=7.8 Hz), 7.58 (ddd, 1H, J=8.4 Hz, 6.9 Hz, 1.5 Hz), 7.50 (ddd, 1H, J=8.0 Hz, 6.9 Hz, 1.2 Hz), 7.37 (m, 7H), 6.26 (t, 1H, J=5.9 Hz), 5.22 (s, 2H), 4.80 (s, 2H), 3.78 (m, 2H), 3.40 (m, 2H), 2.24 (s, 3H).

d. 3-[2-(1-Naphthalene)ethyl]amino-6-methyl-1-carboxymethyl-pyrazinone

A mixture of the product of the preceding step (1.48 g, 3.20 mmol), 10% palladium(0) on carbon (500 mg), and solid KOH (2.05 g, 36.5.mmol) in 2:1:1 tetrahydrofuran/methanol/water was bubbled with nitrogen gas, aspirated, and stirred vigorously under hydrogen (balloon) at ambient temperature. After 16 h the reaction was filtered over Celite, the frit washed with methanol/water, and the filtrate evaporated. The residue was treated with 10% aqueous HCl, cooled, and filtered, the precipitate washed with water and ether and dried in vacuo overnight giving the title compound (0.84 g, 78%) as a golden solid that appeared to be a TLC-inseparable mixture of 5-chloro and 5-hydro products by NMR. $^1$H NMR (400 MHz, CDCl$_3$) δ 8.54 (d, 0.5H, J=8.3 Hz), 8.25 (d, 1H, J=8.2 Hz), 7.93 (t, 2H, J=7.1 Hz), 7.82 (t, 2H, J=8.6 Hz), 7.51 (m,7H), 6.75 (s, 1H), 4.77 (s, 1H), 4.74 (s, 2H), 3.79 (m, 2H), 3.56 (m, 1H), 3.40 (m, 2H), 3.31 (m, 1H), 2.25 (s, 1.5H), 2.17 (s, 3H).

e. 1-{N-[2-(N',N"-Bis{tert-butoxycarbonyl}amidinoaminooxy)ethyl]amino}carbonylmethyl-6-methyl-3-[2-(1-naphthalene)ethyl]amino-pyrazinone The product of the preceding step (0.84 g, 2.49 mmol), Casto's reagent (1.15 g, 2.60 mmol), and [N,N'-di(tert-butoxycarbonyl)]-2-aminoethoxyguanidine (0.91 g, 2.55 mmol), as prepared in step d of Example 1, were dissolved in N,N-dimethylformamide (50 mL) and treated with triethylamine (1.0 mL, 7.2 mmol) at ambient temperature. After stirring overnight the reaction was evoprated in vacuo and the residue purified by flash column chromatography (ethyl acetate) giving the title compound (0.79 g, 50%) as a light orange solid. $^1$H NMR (400 MHz, CDCl$_3$) δ 9.17 (s, 1H), 8.41 (m, 1H), 8.13 (d, 1H, J=8.4 Hz), 7.84 (m, 1H), 7.73 (dd, 1H, J=7.5 Hz, 1.6 Hz), 7.58 (m, 1H), 7.50 (m, 2H), 7.37 (m, 3H), 6.72 (d, 1H, J=0.9 Hz), 6.15 (m, 1H), 4.77 (s, 2H), 4.12 (m, 2H), 3.76 (m, 2H), 3.61 (dd, 2H, J=8.7Hz, 5.1 Hz), 3.39 (t, 2H, J=7.3Hz), 2.14 (d, 3H, J=0.7Hz), 1.51 (s, 9H), 1.47 (s, 9H).

f. 1-{N-[2-(Amidinoaminooxy)ethyl]amino}carbonylmethyl-6-methyl-3-[2-(1-naphthalene)ethyl]amino-pyrazinone hydrochloride The product of the preceding step (0.79 g, 1.25 mmol) was dissolved in dichloromethane (10 mL) and reacted with trifluoroacetic acid (5 mL) at ambient temperature overnight. The reaction was concentrated in vacuo, the residue purified by flash column chromatography (15% methanol in dichloromethane, saturated with ammonia gas), and the evaporated column fractions treated with 4N HCl in ethanol and concentrated under high vacuum giving the title compound (0.43 g, 73%) as a pale yellow solid. $^1$H NMR (400 MHz, DMSO-d$_6$) δ 11.1 (s, 1H), 8.71 (t, 1H, J=5.3 Hz), 8.26 (d, 1H, J=8.2 Hz), 7.94 (d, 1H, J=8.1 Hz), 7.83 (d, 1H, J=8.2 Hz), 7.78 (bs, 4H), 7.56 (m, 3H), 7.46 (t, 1H, J=7.5 Hz), 6.73 (s, 1H), 4.69 (s, 2H), 3.80 (m, 4H), 3.42 (m, 4H), 2.14 (s, 3H). Mass spectrum (LCMS, ESI pos.) calcd. for C$_{22}$H$_{27}$N$_7$O$_3$: 438.2 (M+H). Found: 438.2.

EXAMPLE 9
1-{N-[2-(amidinoaminooxy)ethyl]amino}carbonylmethyl-6-methyl-3-(2-phenyl-1-butylamino)-pyrazinone trifluoroacetate

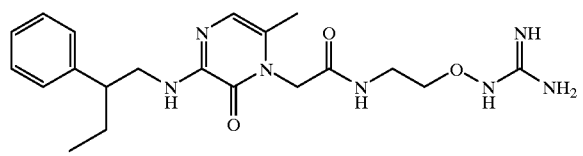

The title compound was prepared as a pale yellow solid from 1-phenyl-cyclopropane carbonitrile, in a manner analogous to Example 7, except that the cyclopropane ring was opened during the catalytic hydrogenation. $^1$H NMR (300 MHz, CDCl$_3$/CD$_3$OD) δ 7.24–7.07 (m, 5H), 6.47 (s, 1H), 3.81 (t, 2H, J=4.7 Hz), 3.62 (dd, 1H, J=13.5 Hz, 6.3 Hz), 3.42 (dd, 1H, J=13.6 Hz, 9.0 Hz), 3.35 (t, 2H, J=4.6 Hz), 2.73 (m, 1H), 2.02 (s, 3H), 1.72–1.44 (m, 2H), 0.69 (t, 3H, J=7.3 Hz). Mass spectrum (MALDI-TOF, gentisic acid matrix) calcd. for C$_{20}$H$_{29}$N$_7$O$_3$: 416.2 (M+H), 438.2 (M+Na). Found: 416.4, 438.4.

EXAMPLE 10
1-{N-[2-(amidinoaminooxy)ethyl]amino}carbonylmethyl-6-methyl-3-(2-[3,4-methylenedioxyphenyl]ethylamino)-pyrazinone trifluoroacetate

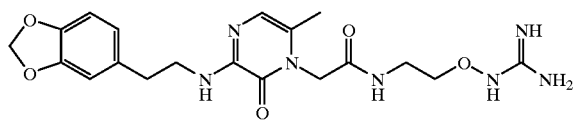

The title compound was prepared as a pale yellow oil from 3,4-methylenedioxyphenethylamine hydrochloride, in a manner analogous to Example 1. $^1$H NMR (300 MHz, CDCl$_3$/CD$_3$OD) δ 6.70 (m, 3H), 6.63 (s, 1H), 5.91 (s, 2H), 4.67 (s, 2H), 3.95 (t, 2H, J=4.8Hz), 3.61 (t, 2H, J=7.3 Hz), 3.49 (t, 2H, J=4.7 Hz), 2.86 (t, 2H, J=7.3 Hz), 2.17 (s, 3H). Mass spectrum (MALDI-TOF, α-cyano-4-hydroxycinnamic acid matrix) calcd. for C$_{19}$H$_{25}$N$_7$O$_5$: 432.2 (M+H), 454.2 (M+Na). Found: 432.6, 454.8.

EXAMPLE 11
1-{N-[2-(amidinoaminooxy)ethyl]amino}carbonylmethyl-6-methyl-3-(2-[2-pyridyl]ethylamino)-pyrazinone trifluoroacetate

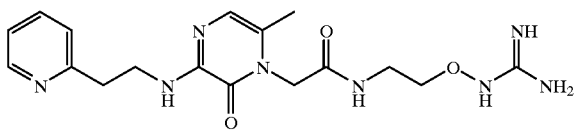

The title compound was prepared as an orange oil from 2-(2-aminoethyl)pyridine, in a manner analogous to Example 1. $^1$H NMR (300 MHz, CDCl$_3$/CD$_3$OD) δ 8.46 (d, 1H, J=4.2 Hz), 7.74 (t, 1H, J=7 Hz), 7.34 (d, 1H, J=7.7 Hz), 7.25 (dd, 1H, J=7.1 Hz, 4.9 Hz), 6.71 (s, 1H), 3.99 (t, 2H, J=4.5 Hz), 3.72 (t, 2H, J=6.7 Hz), 3.54 (m, 2H), 3.11 (t, 2H, J=6.7 Hz), 2.18 (s, 3H). Mass spectrum (MALDI-TOF, gentisic acid matrix) calcd. for C$_{17}$H$_{24}$N$_8$O$_3$: 389.2 (M+H), 411.2 (M+Na). Found: 389.8, 411.6.

EXAMPLE 12
1-{N-[2-(amidinoaminooxy)ethyl]amino}carbonylmethyl-6-methyl-3-(2-[2-methylphenyl]ethylamino)-pyrazinone trifluoroacetate

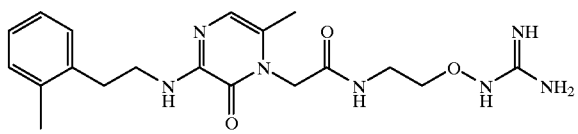

The title compound was prepared as a pale orange solid from 2-methylbenzyl cyanide, in a manner analogous to Example 7. $^1$H NMR (300 MHz, DMSO-d$_6$) δ 11.13 (s, 1H), 8.48 (t, 1H, J=5.5 Hz), 7.83 (bs, 4H), 7.12 (m, 4H), 6.68 (d, 1H, J=1.0 Hz), 4.63 (s, 2H), 3.82 (t, 2H, J=5.4 Hz), 3.47 (m, 2H), 3.39 (q, 2H, J=5 Hz), 2.85 (m,2H), 2.31 (s, 3H), 2.08 (s, 3H). Mass spectrum (LCMS, ESI pos.) calcd. for C$_{19}$H$_{27}$N$_7$O$_3$: 402.2 (M+H). Found: 402.2.

EXAMPLE 13
1-{N-[2-(amidinoaminooxy)ethyl]amino}carbonylmethyl-6-methyl-3-(2-[3-methylphenyl]ethylamino)-pyrazinone hydrochloride

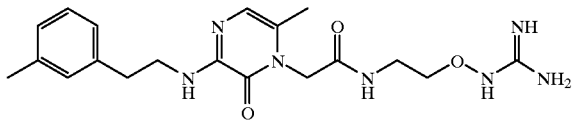

The title compound was prepared as a pale yellow solid from 3-methylbenzyl cyanide, in a manner analogous to Example 7. $^1$H NMR (400 MHz, DMSO-d$_6$) δ 11.16 (s, 1H), 8.74 (t, 1H, J=5.5 Hz), 7.80 (bs, 4H), 7.19 (t, 1H, J=7.5 Hz), 7.16 (s, 1H), 7.12 (d, 1H, J=7.5 Hz), 7.03 (d, 1H, J=7.4 Hz), 6.70 (s, 1H), 4.67 (s, 2H), 3.82 (t, 2H, J=5.2 Hz), 3.69 (m, 2H), 3.39 (q, 2H, J=5.3 Hz), 2.89 (t, 2H, J=7.6 Hz), 2.28 (s, 3H), 2.14 (s, 3H). Mass spectrum (LCMS, ESI pos.) calcd. for C$_{19}$H$_{27}$N$_7$O$_3$: 402.2 (M+H). Found: 402.2.

EXAMPLE 14
1-{N-[2-(amidinoaminooxy)ethyl]amino}carbonylmethyl-6-methyl-3-(2-[2-trifluoromethylphenyl]ethylamino)-pyrazinone hydrochloride

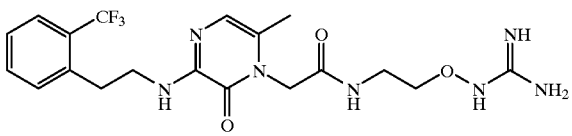

The title compound was prepared as a pale yellow solid from 2-(trifluoromethyl)phenethyl alcohol, in a manner analogous to Example 8. $^1$H NMR (400 MHz, DMSO-d$_6$) δ 11.09 (s, 1H), 8.66 (t, 1H, J=5.5 Hz), 7.76 (bs, 4H), 7.70 (m, 2H), 7.64 (t, 1H, J=7.5 Hz), 7.46 (t, 1H, J=7.6 Hz), 6.72 (s, 1H), 4.67 (s, 2H), 3.82 (t, 2H, J=5.3 Hz), 3.71 (m, 2H), 3.39 (q, 2H, J=5.5 Hz), 3.11 (t, 2H, J=7.3 Hz), 2.13 (s, 3H). Mass spectrum (LCMS, ESI pos.) calcd. for C$_{19}$H$_{24}$N$_7$O$_3$F$_3$: 456.2 (M+H). Found: 456.1.

EXAMPLE 15
1-{N-[2-(amidinoaminooxy)ethyl]amino}carbonylmethyl-6-methyl-3-(2-[3-trifluoromethylphenyl ]ethylamino)-pyrazinone trifluoroacetate

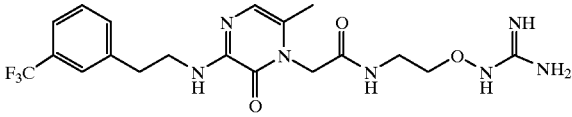

The title compound was prepared as a white solid from 3-(trifluoromethyl)phenethyl alcohol, in a manner analogous to Example 8. $^1$H NMR (400 MHz, DMSO-d$_6$) δ 11.01 (s, 1H), 8.47 (t, 1H, J=5.6 Hz), 7.75 (bs, 4H), 7.57 (m, 4H), 6.68 (s, 11H), 4.62 (s, 2H), 3.81 (t, 2H, J=5.4 Hz), 3.57 (q, 2H, J=6.6 Hz), 3.37 (m, 2H), 2.98 (t, 2H, J=7.3 Hz), 2.10 (s, 3H). Mass spectrum (LCMS, ESI pos.) calcd. for C$_{19}$H$_{24}$N$_7$O$_3$F$_3$: 456.2 (M+H). Found: 456.2.

EXAMPLE 16

1-{N-[2-(amidinoaminooxy)ethyl]amino}carbonylmethyl-6-methyl-3-(2-[4-trifluoromethylphenyl]ethylamino)-pyrazinone trifluoroacetate

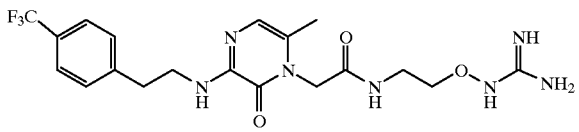

The title compound was prepared as a tan solid from 4-(trifluoromethyl)phenylacetonitrile, in a manner analogous to Example 7. $^1$H NMR (400 MHz, DMSO-d$_6$) δ 10.98 (s, 1H), 8.45 (t, 1H, J=5.5 Hz), 7.74 (bs, 4H), 7.66 (d, 2H, J=8.1 Hz), 7.47 (d, 2H, J=8.0 Hz), 6.68 (s, 1H), 4.62 (s, 2H), 3.81 (t, 2H, J=5.4 Hz), 3.38 (q, 2H, J=5.4 Hz), 2.97 (t, 2H, J=7 Hz), 2.08 (s, 3H). Mass spectrum (LCMS, ESI pos.) calcd. for C$_{19}$H$_{24}$N$_7$O$_3$F$_3$: 456.2 (M+H). Found: 456.2.

EXAMPLE 17

1-{N-[2-(amidinoaminooxy)ethyl]amino}carbonylmethyl-6-methyl-3-(2-[3,5-dimethylphenyl]ethylamino)-pyrazinone trifluoroacetate

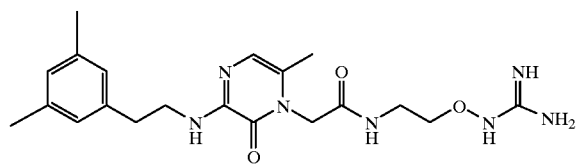

The title compound was prepared as a pale yellow solid from 3,5-dimethylphenylacetonitrile, in a manner analogous to Example 7. $^1$H NMR (400 MHz, DMSO-d$_6$) δ 10.88 (s, 1H), 8.44 (t, 1H, J=5.7 Hz), 7.68 (bs, 4H), 6.84 (s, 3H), 6.68 (s, 1H), 4.61 (s, 2H), 3.81 (t, 2H, J=5.4 Hz), 2.77 (t, 2H, J=7.6 Hz), 2.24 (s, 6H), 2.08 (s, 3H). Mass spectrum (LCMS, ESI pos.) calcd. for C$_{20}$H$_{29}$N$_7$O$_3$: 416.2 (M+H). Found: 416.2.

EXAMPLE 18

1-{N-[2-(amidinoaminooxy)ethyl]amino}carbonylmethyl-6-methyl-3-(2-indanylamino)-pyrazinone hydrochloride

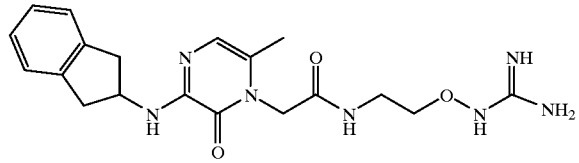

The title compound was prepared as a white solid from 2-aminoindan hydrochloride, in a manner analogous to Example 1. $^1$H NMR (400 MHz, DMSO-d$_6$) δ 10.95 (s, 1H), 8.54 (m, 1H), 7.69 (bs, 4H), 7.17 (m, 4H), 6.71 (s, 1H), 4.64 (s, 2H), 3.81 (t, 2H, J=5.3 Hz), 3.27 (dd, 2H, J=16 Hz, 7.6 Hz), 3.05 (dd, 2H, J=16 Hz, 6.7 Hz),2.11 (s,3H). Mass spectrum (LCMS, ESI pos.) calcd. for C$_{19}$H$_{25}$N$_7$O$_3$: 400.2 (M+H). Found: 400.3.

EXAMPLE 19

1-{N-[2-(amidinoaminooxy)ethyl]amino}carbonylmethyl-6-methyl-3-(2-[3,4-difluorophenyl]ethylamino)-pyrazinone hydrochloride

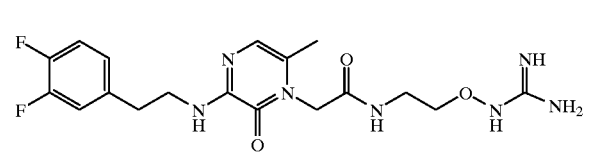

The title compound was prepared as a white solid from 3,4-difluorophenylacetonitrile, in a manner analogous to Example 7. $^1$H NMR (400 MHz, DMSO-d$_6$) δ 11.05 (s, 1H), 8.63 (t, 1H, J=5.5 Hz), 7.74 (bs, 4H), 7.46 (t, 1H, J=10 Hz), 7.36 (dt, 1H, J=10.9 Hz, 8.5 Hz), 7.15 (m, 1H), 6.70 (s, 1H), 4.66 (s, 2H), 3.82 (t, 2H, J=5.4 Hz), 3.66 (m, 2H), 3.38 (m, 2H), 2.91 (t, 2H, J=7.4 Hz), 2.13 (s, 3H). Mass spectrum (LCMS, ESI pos.) calcd. for C$_{18}$H$_{23}$N$_7$O$_3$F$_2$: 424.2 (M+H). Found: 424.2.

EXAMPLE 20

1-{N-[2-(amidinoaminooxy)ethyl]amino}carbonylmethyl-6-methyl-3-(2-[5-indanyl]ethylamino)-pyrazinone hydrochloride

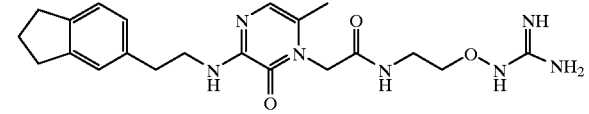

The title compound was prepared as a pale yellow solid from 5-indanyl-acetonitrile (F. Lauria and W. Logemann, U.S. Pat. No. 3,452,085) in a manner analogous to Example 7. $^1$H NMR (400 MHz, DMSO-d$_6$) δ 11.13 (s, 1H), 8.71 (t, 1H, J=5.5 Hz), 7.78 (bs, 4H), 7.19 (s, 1H), 7.14 (d, 1H, J=7.7 Hz), 7.07 (m, 1H), 6.70 (s, 1H), 4.67 (s, 2H), 3.82 (t, 2H, J=5.3 Hz), 3.65 (m, 2H), 2.84 (m, 6H), 2.13 (s, 3H), 1.99 (pentet, 2H, J=7.4 Hz). Mass spectrum (LCMS, ESI pos.) calcd. for C$_{21}$H$_{29}$N$_7$O$_3$: 428.2 (M+H). Found: 428.3.

EXAMPLE 21

1-{N-[2-(amidinoaminooxy)ethyl]amino}carbonylmethyl-6-methyl-3-(2-fluorophenethylamino)-pyrazinone trifluoroacetic acid salt

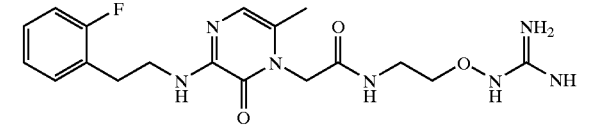

The title compound was prepared from 1-benzyloxycarbonylmethyl-3,5-dichloro-6-methylpyrazinone, as prepared in the step f of Example 1, and 2-fluorophenethylamine using the procedures of Example 1, steps g-j. $^1$H-NMR (300 MHz, DMSO-d$_6$) δ 10.91 (s, 1H), 8.43 (t, J=5.6 Hz, 1H), 7.70 (br s, 4H), 7.30 (m, 2H), 7.15 (m,3H), 6.66 (s, 1H), 4.61 (s, 2H), 3.81 (t, J=5.4 Hz, 2H), 3.37 (m, 4H), 2.90 (t, J=7.2 Hz, 2H), 2.06 (s, 3H). Mass spectrum (MALDI-TOF, α-cyano-4-hydroxycinnamic acid matrix) Calcd. for C$_{18}$H$_{24}$FN$_7$O$_3$: 406.2 (M+H), 428.2 (M+Na); Found: 406.3, 428.3.

EXAMPLE 22

1-{N-[2-(amidinoaminooxy)ethyl]amino}carbonylmethyl-6-methyl-3-(3,4-dimethoxyphenethylamino)-pyrazinone trifluoroacetic acid salt

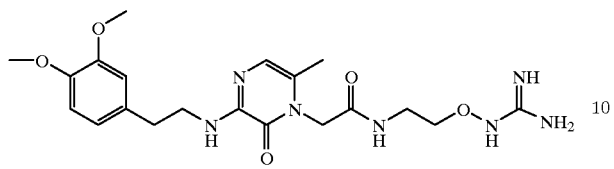

The title compound was prepared from 1-benzyloxycarbonylmethyl-3,5-dichloro-6-methylpyrazinone, as prepared in the step f of Example 1, and 3,4-dimethoxyphenethylamine using the procedures of Example 1, steps g-j. $^1$H-NMR (300 MHz, DMSO-d$_6$) δ 10.95 (s, 1H), 8.44 (t, J=5.6 Hz, 1H), 7.72 (br s, 4H), 6.85 (t, J=8.1 Hz, 2H), 6.73 (d, J=8.1 Hz, 2H), 6.67 (s, 1H), 4.61 (s, 2H), 3.81 (t, J=5.3 Hz, 2H), 3.73 (s, 3H), 3.71 (s, 3H), 3.39 (m, 4H), 2.79 (t, J=7.2 Hz, 2H), 2.07 (s, 3H). Mass spectrum (MALDI-TOF, α-cyano-4-hydroxycinnamic acid matrix) Calcd. for $C_{20}H_{29}N_7O_5$: 448.2 (M+H), 470.2 (M+Na); Found: 448.6, 470.4.

EXAMPLE 23

1-{N-[2-(amidinoaminooxy)ethyl]amino}carbonylmethyl-6-methyl-3-(4-fluorophenethylamino)-pyrazinone trifluoroacetic acid salt

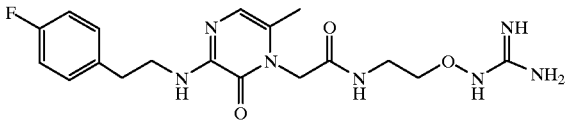

The title compound was prepared from 1-benzyloxycarbonylmethyl-3,5-dichloro-6-methylpyrazinone, as prepared in the step f of Example 1, and 4-fluorophenethylamine using the procedures of Example 1, steps g-j. $^1$H-NMR (300 MHz, DMSO-d$_6$) δ 10.97 (s, 1H), 8.45 (t, J=5.6 Hz, 1H), 7.74 (br s, 4H), 7.26 (m, 3H), 7.15 (t, J=8.8 Hz, 2H), 6.68 (s, 1H), 4.61 (s, 2H), 3.81 (t, J=5.4 Hz, 2H), 3.39 (m, 4H), 2.85 (t, J=7.3 Hz, 2H), 2.07 (s, 3H). Mass spectrum (MALDI-TOF, α-cyano-4-hydroxycinnamic acid matrix) Calcd. for $C_{18}H_{24}FN_7O_3$: 406.2 (M+H), 428.2 (M+Na); Found: 406.6, 428.5.

EXAMPLE 24

1-{N-[2-(amidinoaminooxy)ethyl]amino}carbonylmethyl-6-methyl-3-(4-ethylphenethylamino)-pyrazinone trifluoroacetic acid salt

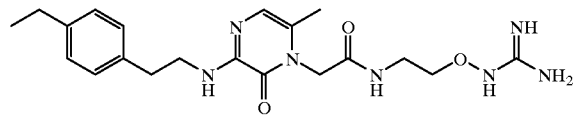

The title compound was prepared from 1-benzyloxycarbonylmethyl-3,5-dichloro-6-methylpyrazinone, as prepared in the step f of Example 1, and 4-ethylphenethylamine using the procedures of Example 7, steps b-e. $^1$H-NMR (300 MHz, DMSO-d$_6$) δ 10.97 (s, 1H), 8.44 (t, J=5.6 Hz, 1H), 7.73 (br s, 4H), 7.18 (m, 1H), 7.14 (s, 4H), 6.67 (s, 1H), 4.61 (s, 2H), 3.81 (t, J=5.2 Hz, 2H), 3.39 (m, 4H), 2.82 (t, J=7.5 Hz, 2H), 2.56 (q, J=7.6 Hz, 2H), 2.07 (s, 3H), 1.16 (t, J =7.5 Hz, 3H). Mass spectrum (MALDI-TOF, α-cyano-4-hydroxycinnamic acid matrix) Calcd. for $C_{20}H_{29}N_7O_3$: 416.2 (M+H), 438.2 (M+Na); Found: 416.2, 439.2.

EXAMPLE 25

1-{N-[2-(amidinoaminooxy)ethyl]amino}carbonylmethyl-6-methyl-3-(2-phenylpropylamino)-pyrazinone trifluoroacetic acid salt

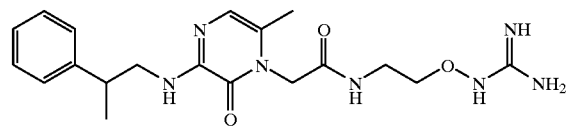

The title compound was prepared from 1-benzyloxycarbonylmethyl-3,5-dichloro-6-methylpyrazinone, as prepared in the step f of Example 1, and (-methylphenethylamine using the procedures of Example 7, steps b-e. $^1$H-NMR (300 MHz, DMSO-d$_6$) δ 10.98 (s, 1H), 8.43 (t, J=5.6 Hz, 1H), 7.74 (br s, 4H), 7.28 (m,5H), 7.20 (m, 1H), 6.66 (s, 1H), 4.59 (s, 2H), 3.80 (t, J=5.4 Hz, 2H), 3.44 (t, J=6.5 Hz, 2H), 3.38 (t, J=5.4 Hz, 2H), 3.13 (q, J =7.1 Hz, 2H), 2.06 (s, 3H), 1.19 (d, J=7.0 Hz, 3H). Mass spectrum (MALDI-TOF, (-cyano-4-hydroxycinnamic acid matrix) Calcd. for $C_{19}H_{27}N_7O_3$: 402.2 (M+H), 424.2 (M+Na); Found: 402.4, 424.5.

EXAMPLE 26

1-{N-[2-(amidinoaminooxy)ethyl]amino}carbonylmethyl-6-methyl-3-(3,4-dimethylphenethylamino)-pyrazinone trifluoroacetic acid salt

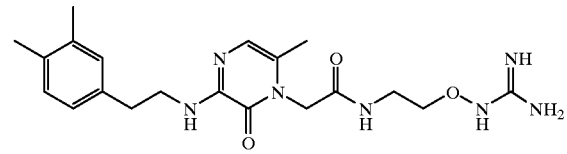

The title compound was prepared from 3,4-dimethylbenzyl cyanide using the procedures of Example 7, steps a-e. $^1$H-NMR (300 MHz, DMSO-d$_6$) δ 11.10 (s, 1H), 8.47 (t, J=5.5 Hz, 1H), 7.81 (br s, 4H), 7.55 (m, 1H), 7.03 (t, J=7.9 Hz, 2H), 6.94 (d, J=7.8 Hz, 1H), 6.68 (s, 1H), 4.62 (s, 2H), 3.82 (t, J=5.3 Hz, 2H), 3.48 (m, 2H), 3.38 (m, 2H), 2.78 (t, J=7.5 Hz, 2H), 2.19 (s, 3H), 2.17 (s, 3H), 2.08 (s, 3H). Mass spectrun (MALDI-TOF, α-cyano-4-hydroxycinnamic acid matrix) Calcd. for $C_{20}H_{29}N_7O_3$: 416.2 (M+H), 438.2 (M+Na); Found: 416.0, 437.9.

EXAMPLE 27
1-{N-[2-(amidinoaminooxy)ethyl]amino}carbonylmethyl-6-methyl-3-(2-naphthaleneethylamino)-pyrazinone trifluoroacetic acid salt

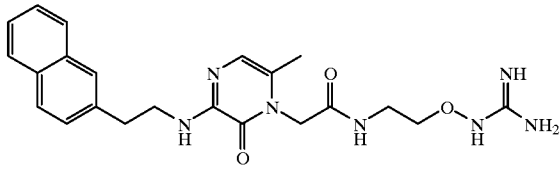

The title compound was prepared from 2-naphthaleneethanol using the procedures of Example 8, steps a-f. $^1$H-NMR (400 MHz, DMSO-$d_6$) δ 10.90 (s, 1H), 8.43 (t, J=5.5 Hz, 1H), 7.87 (m, 3H), 7.85 (s, 1H), 7.69 (br s, 4H), 7.47 (m, 3H), 6.69 (s, 1H), 4.61 (s, 2H), 3.80 (t, J=5.4 Hz, 2H), 3.61 (m, 4H), 3.04 (t, J=7.2 Hz, 2H), 2.07 (s, 3H). Mass spectrum (LCMS, ESI) Calcd. for $C_{22}H_{27}N_7O_3$: 438.2 (M+H); Found: 438.2.

EXAMPLE 28
1-{N-[2-(amidinoaminooxy)ethyl]amino}carbonylmethyl-6-methyl-3-(2,2-diphenylpropylamino)-pyrazinone trifluoroacetic acid salt

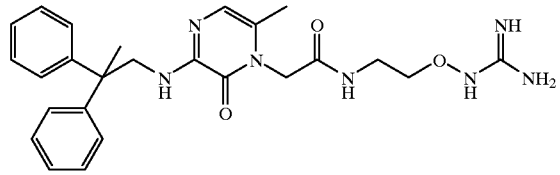

The title compound was prepared from 1-benzyloxycarbonylmethyl-3,5-dichloro-6-methylpyrazinone, as prepared in the step f of Example 1, and 2,2-diphenylpropylamine hydrochloride using the procedures of Example 1, steps g-j. $^1$H-NMR (400 MHz, DMSO-$d_6$) δ 10.89 (s, 1H), 8.41 (t, J=5.4 Hz, 1H), 7.70 (br s, 4H), 7.32 (m, 4H), 7.26 (m, 6H), 6.68 (s, 1H), 5.75 (m, 1H), 4.56 (s, 2H), 4.00 (d, J=5.0Hz, 2H), 3.79 (t, J=5.4 Hz, 2H), 3.36 (m,2H), 2.05 (s, 3H), 1.67 (s, 3H). Mass spectrum (LCMS, ESI) Calcd. for $C_{25}H_{31}N_7O_3$: 478.2 (M+H); Found: 478.2.

EXAMPLE 29
1-{N-[2-(amidinoaminooxy)ethyl]amino}carbonylmethyl-6-methyl-3-(2-(3-indolyl)-ethylamino)-pyrazinone trifluoroacetic acid salt

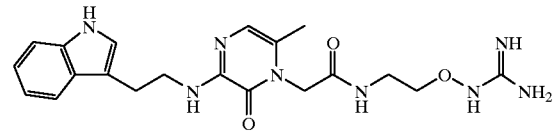

The title compound was prepared from 1-benzyloxycarbonylmethyl-3,5-dichloro-6-methylpyrazinone, as prepared in the step f of Example 1, and tryptamine using the procedures of Example 1, steps g-j. $^1$H-NMR (400 MHz, DMSO-$d_6$) δ 10.98 (s, 1H), 8.44 (t, J=5.6 Hz, 1H), 7.74 (br s, 4H), 7.00–7.60 (m, 6H), 6.69 (s, 1H), 4.62 (s, 2H), 3.81 (t, J=5.3 Hz, 2H), 3.39 (m, 4H), 2.97 (t, J=7.4 Hz, 2H), 2.08 (s, 3H). Mass spectrum (LCMS, ESI) Calcd. for $C_{24}H_{26}N_8O_3$: 427.2 (M+H); Found: 427.3.

EXAMPLE 30
1-{N-[2-(amidinoaminooxy)ethyl]amino}carbonylmethyl-6-methyl-3-(2-[1-(4-methylnaphthalene)]ethylamino)-pyrazinone trifluoroacetate

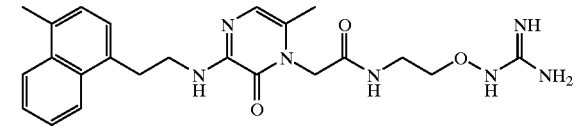

The title compound was prepared as a white solid from 1-(4-methylnaphthalene)acetonitrile, in a manner analogous to Example 7. $^1$H NMR (400 MHz, DMSO-$d_6$) δ 10.94 (s, 1H), 8.45 (t, J=5.6 Hz, 1H), 8.33 (d, J=7.2 Hz, 1H), 8.04 (d, J=7.1 Hz, 1H), 7.72 (br s, 4H), 7.58 (m, 2H), 7.28 (s, 2H), 6.73 (s, 1H), 4.63 (s, 2H), 3.82 (t, J=5.4 Hz, 2H), 3.57 (m, 2H), 3.40 (t, J=6.4 Hz, 2H), 3.29 (t, J=7.3 Hz, 2H), 2.62 (s, 3H), 2.09 (s, 3H). Mass spectrum (MALDI-TOF, α-cyano-4-hydroxycinnamic acid matrix) Calcd. for $C_{23}H_{29}N_7O_3$: 452.2 (M+H), 474.2 (M+Na); Found: 452.2, 474.3.

EXAMPLE 31
1-{N-[2-(amidinoaminooxy)ethyl]amino}carbonylmethyl-6-methyl-3-(2-[2,4-difluorophenyl]ethylamino)-pyrazinone trifluoroacetate

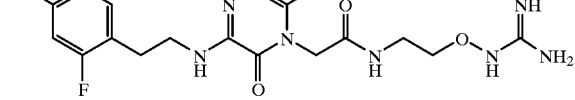

The title compound was prepared as a white solid from 2,4-difluorophenylethanol, in a manner analogous to Example 8. $^1$H NMR (400 MHz, DMSO-$d_6$) δ 11.03 (s, 1H), 8.46 (t, J=5.6 Hz, 1H), 7.77 (br s, 4H), 7.34 (q, J=7.8Hz, 1H), 7.18 (t, J=9.5Hz, 1H), 7.03 (t, J=8.0 Hz, 1H), 6.67 (s, 1H), 4.62 (s, 2H), 3.81 (t, J=5.4 Hz, 2H), 3.51 (m, 2H), 3.39 (t, J=5.5 Hz, 2H), 2.89 (t, J =7.1 Hz, 2H), 2.08 (s, 3H). Mass spectrum (MALDI-TOF, α-cyano-4-hydroxycinnamic acid matrix) Calcd. for $C_{19}H_{23}F_2N_7O_3$: 424.2 (M+H), 446.2 (M+Na); Found: 424.3, 446.5.

EXAMPLE 32
1-{N-[2-(amidino-N'-methylaminooxy)ethyl]amino}carbonylmethyl-6-methyl-3-(2-[4-methylphenyl]ethylamino)-pyrazinone hydrochloride

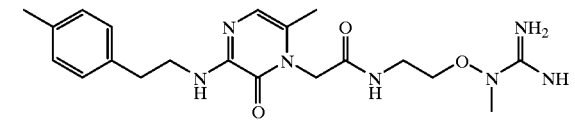

To a mixture of the product of Example 5 (0.09 g, 0.19 mmol) and sodium bicarbonate (0.53 g, 6.30 mmol) in N,N-dimethylformamide (10 mL) was added iodomethane (0.04 mL, 0.64 mmol). After stirring 2 d at ambient temperature, the solution was concentrated in vacuo, the residue treated with pH 1 brine, and basified with solid KOH. The resulting precipitate was filtered, washed with water, and taken off the filter with methanol. The evaporated filtrate was dissolved in 1:1 methanol/dichloromethane, filtered and the filtrate evaporated, the residue treated with 2 mL of 4 N HCl in ethanol, dissolved in methanol/ dichloromethane, and filtered again. The filtrate was then concentrated in vacuo giving the title compound as a yellow solid (0.08 g, 86%). $^1$H NMR (400 MHz, DMSO-d$_6$) δ 8.62 (t, 1H, J=5.3 Hz), 7.90 (bs, 3H), 7.18 (d, 2H, J=7.9 Hz), 7.11 (d, 2H, J=7.9Hz), 6.70 (s, 1H), 4.64 (s, 2H), 3.91 (t, 2H, J=5.2 Hz), 3.39 (q, 2H, J=5.2 Hz), 3.25 (s, 3H), 2.86 (t, 2H, J=7.5 Hz), 2.27 (s, 3H), 2.12 (s, 3H). Mass spectrum (LCMS, ESI pos.) calcd. for $C_{20}H_{29}N_7O_3$: 416.2 (M+H). Found: 416.2; MS/MS found 374.1 (M-C(=NH)NH$_2$).

EXAMPLE 33

1-{N-[2-(amidinoaminooxy)ethyl]amino}carbonylmethyl-6-methyl-3-(2,2-difluoro-2-phenylethylamino)-pyrazinone trifuoroacetic acid salt

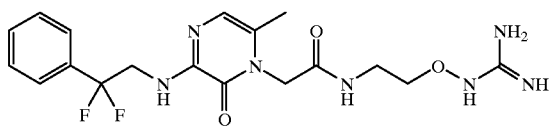

The title compound was prepared from 1-benzyloxycarbonylmethyl-3,5-dichloro-6-methylpyrazinone, as prepared in step f of Example 1, and 2,2-difluoro-2-phenylethylamine using the procedures of Example 1, steps g-j. $^1$H-NMR (400 MHz, DMSO-d$_6$) δ 10.89 (s, 1H), 8.46 (t, J=5.5 Hz, 1H), 7.69 (br s, 4H), 7.53 (m, 2H), 7.50 (m, 3H), 6.84 (t, J=6.5 Hz, 1H), 6.64 (s, 1H), 4.62 (s, 2H), 4.06 (dt, J=6.5, 14.4 Hz, 2H), 3.81 (t, J=5.4 Hz, 2H), 3.38 (m, 2H), 2.06 (s, 3H). Mass spectrum (LCMS, ESI) Calcd. for $C_{18}H_{23}F_2N_7O_3$: 424.3 (M+H); Found 424.4.

EXAMPLE 34

Tablet Preparation

Tablets containing 25.0, 50.0, and 100.0 mg, respectively, of the following active compounds are prepared as illustrated below:

a. 1-{N-[2-(amidinoaminooxy)ethyl] amino}carbonylmethyl-6-methyl-3-(4-methoxyphenethylamino)pyrazinone; and b. 1-{N-[2-(amidinoaminooxy)ethyl] amino}carbonylmethyl-6-methyl-3-(2,2-diphenylethylamino)pyrazinone.

| TABLET FOR DOSES CONTAINING FROM 25–100 MG OF THE ACTIVE COMPOUND | | | |
|---|---|---|---|
| | Amount-mg | | |
| Active Compound | 25.0 | 50.0 | 100.00 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 35

Intravenous Solution Preparation

An intravenous dosage form of the above-indicated active compounds is prepared as follows:

| | |
|---|---|
| Active Compound | 0.5–10.0 mg |
| Sodium Citrate | 5–50 mg |
| Citric Acid | 1–15 mg |
| Sodium Chloride | 1–8 mg |
| Water for Injection (USP) | q.s. to 1 ml |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md. (1994).

EXAMPLE 36

In vitro Inhibition of Purified Enzymes

Reagents: All buffer salts were obtained from Sigma Chemical Company (St. Louis, Mo.), and were of the highest purity avalable. The enzyme substrates, N-benzoyl-Phe—Val—Arg-p-nitroanilide (Sigma B7632), N-benzoyl-Ile—Glu—Gly—Arg-p-nitroanilide hydrochloride (Sigma B2291), N-p-Tosyl-Gly—Pro—Lys-p-nitroanilide (Sigma T6140), N-succinyl-Ala—Ala—Pro—Phe-p-nitroanilide (Sigma S7388) and N-CBZ-Val—Gly—Arg-p-nitroanilide (Sigma C7271) were obtained from Sigma. N-succinyl-Ala—Ala—Pro—Arg-p-nitroanilide (BACHEM L-1720) and N-succinyl-Ala—Ala—Pro—Val-p-nitroanilide (BACHEM L-1770) were obtained from BACHEM (King of Prussia, Pa.).

Human α-thrombin, human factor Xa and human plasmin were obtained from Enzyme Research Laboratories (South Bend, Ind.). Bovine α-chymotrypsin (Sigma C4129), bovine trypsin (Sigma T8642) and human kidney cell urokinase (Sigma U5004) were obtained from Sigma. Human leukocyte elastase was obtained from Elastin Products (Pacific, Mo.).

$K_i$ Determinations: All assays are based on the ability of the test compound to inhibit the enzyme catalyzed hydrolysis of a peptide-p-nitroanililide substrate. In a typical $K_i$ determination, substrate is prepared in DMSO, and diluted into an assay buffer consisting of 50 mM HEPES, 200 mM NaCl, pH 7.5. The final concentrations for each of the substrates is listed below. In general, substrate concentrations are lower than the experimentally determined value for K. Test compounds are prepared as a 1.0 mg/ml solution in DMSO. Dilutions are prepared in DMSO yielding 8 final concentrations encompassing a 200 fold concentration range. Enzyme solutions are prepared at the concentrations listed below in assay buffer.

In a typical $K_i$ determination, into each well of a 96 well plate is pipetted 280 mL of substrate solution, 10 mL of test compound solution, and the plate allowed to thermally equilibrate at 37° C. in a Molecular Devices plate reader for >15 minutes. Reactions were initiated by the addition of a 10 mL aliquot of enzyme and the absorbance increase at 405 nm is recorded for 15 minutes. Data corresponding to less than 10% of the total substrate hydrolysis were used in the calculations. The ratio of the velocity (rate of change in absorbance as a function of time) for a sample containing no test compound is divided by the velocity of a sample containing test compound, and is plotted as a function of test compound concentration. The data are fit to a linear regression, and the value of the slope of the line calculated. The inverse of the slope is the experimentally determined K value.

Thrombin: Thrombin activity was assessed as the ability to hydrolyze the substrate N-succinyl-Ala—Ala—Pro—Arg-p-nitroanilide. Substrate solutions were prepared at a concentration of 32 mM (32 mM<<Km=180 mM) in assay buffer. Final DMSO concentration was 4.3%. Purified human α-thrombin was diluted into assay buffer to a concentration of 15 nM. Final reagent concentrations were: [thrombin]=0.5 nM, [substrate N-succinyl-Ala—Ala—Pro—Arg-p-nitroanilide]=32 mM.

Factor X [FXa]: FXa activity was assessed as the ability to hydrolyze the substrate N-benzoyl-Ile—Glu—Gly—Arg-p-nitroanilide hydrochloride. Substrate solutions were prepared at a concentration of 51 mM (51<<$K_m$=1.3 mM) in assay buffer. Final DMSO concentration was 4.3%. Purified activated human Factor X was diluted into assay buffer to a concentration of 300 nM. Final reagent concentrations were: [FXa]=10 nM, [N-benzoyl-Ile—Glu—Gly—Arg-p-nitroanilide hydrochloride]=51 mM.

Plasmin: Plasmin activity was assessed as the ability to hydrolyze the N-p-Tosyl-Gly—Pro—Lys-p-nitroanilide. Substrate solutions were prepared at a concentration of 37 mM (37 mM<<$K_m$=243 mM) in assay buffer. Final DMSO concentration was 4.3%. Purified human plasmin was diluted into assay buffer to a concentration of 240 nM. Final reagent concentrations were: [Plasmin]=8 nM, [N-p-Tosyl-Gly—Pro—Lys-p-nitroanilide]=37 mM.

Chymotrypsin: Chymotrypsin activity was assessed as the ability to hydrolyze N-succinyl-Ala—Ala—Pro—Phe-p-nitroanilide. Substrate solutions were prepared at a concentration of 14 mM (14 mM<<$K_m$=62 mM) in assay buffer. Final DMSO concentration was 4.3%. Purified bovine chymotrypsin was diluted into assay buffer to a concentration of 81 nM. Final reagent concentrations were: [Chymotrypsin]=2.7 nM, [N-succinyl-Ala—Ala—Pro—Phe-p-nitroanilide]=14 mM.

Trypsin: Trypsin activity was assessed as the ability to hydrolyze N-benzoyl-Phe—Val—Arg-p-nitroanilide. Substrate solutions were prepared at a concentration of 13 mM (13 mM<<$K_m$=291 mM) in assay buffer. Final DMSO concentration was 4.3%. Purified bovine trypsin was diluted into assay buffer to a concentration of 120 nM. Final reagent concentrations were: [Trypsin]=4 nM, [N-benzoyl-Phe—Val—Arg-p-nitroanilide]=13 mM.

Elastase: Elastase activity was assessed as the ability to hydrolyze N-succinyl-Ala—Ala—Pro—Val-p-nitroanilide. Substrate solutions were prepared at a concentration of 19 mM (19 mM<<$K_m$=89 mM) in assay buffer. Final DMSO concentration was 4.3%. Purified human leukocyte elastase was diluted into assay buffer to a concentration of 750 nM. Final reagent concentrations were: [Elastase]=25 nM, [N-succinyl-Ala-Ala-Pro-Val-p-nitroanilide]=19 mM.

Urokinase: Urokinase activity was assessed as the ability to hydrolyze N-CBZ-Val—Gly—Arg-p-nitroanilide. Substrate solutions were prepared at a concentration of 100 mM (100 mM<$K_m$=1.2 mM) in assay buffer. Final DMSO concentration was 4.3%. Purified human kidney urokinase was diluted into assay buffer to a concentration of 1.2 mM. Final reagent concentrations were: [Urokinase]=40 nM, and [N-CBZ-Val-Gly-Arg-p-nitroanilide]=100 mM.

The results of the compound of Examples 1 through 6 are shown in the following table.

TABLE 1

| | Assay, $K_i$ (μM) (Thrombin) | | | | | |
|---|---|---|---|---|---|---|
| Compound (Eg. No.) | 1 | 2 | 3 | 4 | 5 | 6 |
| $K_i$ (thrombin) | 0.046 | 0.330 | 0.006 | 0.085 | 0.020 | 0.013 |

The results indicate that the compounds of the present invention are potent and highly selective inhibitors of thrombin.

Having now fully described this invention, it will be understood to those of ordinary skill in the art that the same can be performed within a wide and equivalent range of conditions, formulations, and other parameters without affecting the scope of the invention or any embodiment thereof. All patents and publications cited herein are fully incorporated by reference herein in their entirety.

What is claimed is:

1. A thromboresistant surface, comprising a compound of Formula I:

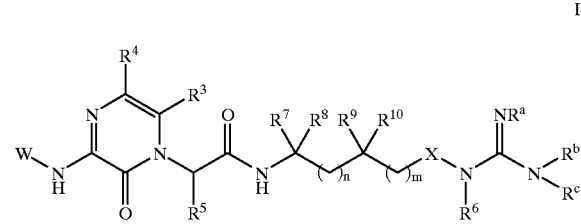

or a hydrate or pharmaceutically acceptable salt thereof; wherein:

W is hydrogen, $R^1$, $R^1OCO$, $R^1CO$, $R^1(CH_2)_sNHCO$, or $(R^1)_2CH(CH_2)_sNHCO$, wherein s is 0–4;

$R^1$ is
  $R^2$,
  $R^2(CH_2)_tC(R^{12})_2$, wherein t is 0–3 and each $R_{12}$ is the same or different,
  $(R^2)(OR^{12})CH(CH_2)_p$, wherein p is 1–4,
  $(R^2)_2(OR^{12})C(CH_2)_p$, wherein p is 1–4,
  $R^2C(R^{12})_2(CH_2)_t$, wherein t is 0–3, and each $R^{12}$ is the same or different, and wherein $(R^{12})_2$, together with the C to which they are attached, can also form a 3- to 7-membered cycloalkyl ring,
  $R^2CH_2C(R^{12})_2(CH_2)_q$, wherein q is 0–2, and each $R^{12}$ is the same or different, and wherein $(R^{12})_2$, together with the C to which they are attached, can also form a 3- to 7-membered cycloalkyl ring,
  $R^2CF_2C(R^{12})_2(CH_2)_q$, wherein q is 0–2, and each $R^{12}$ is the same or different, and wherein $(R^{12})_2$, together with the C to which they are attached, can also for a 3- to 7-membered cycloalkyl ring,
  $(R^2)_2CH(CH_2)_r$, wherein r is 0–4, and each $R_2$ is the same or different, and wherein $(R_2)_2$, together with the C to which they are attached, can also form a $C_{3-7}$ cycloalkyl, $C_{7-12}$ bicyclic alkyl, $C_{10-16}$ tricyclic alkyl, or a 5- to 7- membered, saturated or unsaturated, mono- or bi-cyclic, heterocyclic ring, having from one to three heteroatoms selected from N, O, and S,
  $R^2O(CH_2)_p$, wherein p is 2–4;
  $(R^2)_2CF(CH_2)_r$, wherein r is 0–4 and each $R^{12}$ is the same of different, and wherein $(R^{12})_2$, together with the C to which they are attached, can also form a 3-to 7-membered cycloalkyl, $C_{7-12}$ bicyclic alkyl, $C_{10-16}$ trycyclic alkyl, or a 5- to 7-membered mono- or bicyclic heterocyclic ring which can be saturated or unsaturated, and which contains from one to three heteroatoms selected from the group consisting of N, O and S,

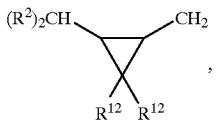

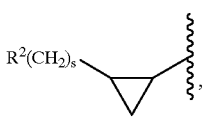

where s is 0 or 1, or
$R^2$ $CF_2C(R^{12})_2$;
$R^2$ is
phenyl, naphthyl or biphenyl, each of which is optionally substituted with one or more of $C_{1-4}$ alkyl, $C_{1-4}$ alkoxy, halogen, hydroxy, $CF_3$, $OCF_3$, COOH, $CONH_2$, or $SO_2NH_2$,
a 5- to 7-membered, saturated or unsaturated, mono- or a 9- to 10-membered bicyclic ring optionally having from one to four heteroatoms selected from N, O, or S, and optionally substituted with halogen or hydroxy,
$C_{1-7}$ alkyl, optionally substituted with one or more of hydroxy, COOH, amino, aryl, $C_{3-7}$ cycloalkyl, $CF_3$, $N(CH_3)_2$, —$C_{1-3}$ alkylaryl or heterocycle,
$CF_3$,
$C_{3-7}$ cycloalkyl, optionally substituted with aryl,
$C_{7-12}$ bicyclic alkyl, or
$C_{10-16}$ tricyclic alkyl;
$R^3$ is
hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —$CO_9R^x$, —$CH_2$ $OR^x$, or $OR^x$, wherein $R^x$, in each instance, is independently one of hydrogen, optionally unsaturated alkyl, or optionally unsaturated cycloalkyl;
$R^4$ is
hydrogen or halogen;
$R^{12}$ is
hydrogen,
phenyl, naphthyl or biphenyl, each of which is optionally substituted with one or more of $C_{1-4}$ alkyl, $C_{1-4}$ alkoxy, halogen, hydroxy, $CF_3$, $OCF_3$, COOH, or $CONH_2$,
a 5- to 7-membered mono- or a 9- to 10-membered bi-cyclic, saturated or unsaturated, heterocyclic ring having from one to four heteroatoms selected from N, O, or S,
$C_{1-4}$ alkyl, optionally substituted with one or more of hydroxy, COOH, amino, aryl or heterocycle,
$CF_3$,
$C_{3-7}$ cycloalkyl,
$C_{7-12}$ bicyclic alkyl, or $C_{10-16}$ tricyclic alkyl;

$R^5$ is hydrogen, $C_{1-4}$ alkyl, or $C_{2-4}$ alkenyl;
$R^6$ is hydrogen, alkyl, alkenyl, aralkyl, aryl, hydroxyalkyl, aminoalkyl, monoalkylamino($C_{2-10}$) alkyl, dialkylamino($C_{2-10}$)alkyl, or carboxyalkyl;
$R^7$, $R^8$, $R^9$, $R^{10}$ are independently hydrogen, alkyl, aralkyl, aryl, hydroxyalkyl, aminoalkyl, monoalkylaminoalkyl, dialkylaminoalkyl, or carboxyalkyl,
or $R^7$ and $R^8$, together with the C to which they are attached, form a 3- to 8-membered cycloalkyl group, and $R^9$ and $R^{10}$ are as defined above,
or $R^9$ and $R^{10}$, together with the C to which they are attached, form a 3- to 8-membered cycloalkyl group, and $R^7$ and $R^8$ are as defined above,
or $R^7$ and $R^9$, together with the C to which they are attached, form a 3- to 8-membered cycloalkyl group, and $R^8$ and $R^{10}$ are as defined above;
X is oxygen, —$NR^{11}$—, or —CH=N—, wherein $R^{11}$ is hydrogen, alkyl, cycloalkyl, or aryl and said alkyl, cycloalkyl and aryl are optionally substituted with amino, monoalkylamino, dialkylamino, alkoxy, hydroxy, carboxy, alkoxycarbonyl, aryloxycarbonyl, aralkoxycarbonyl, aryl, heteroaryl, acetylamino, cyano, or trifluoromethyl; $R^a$, $R^b$ and $R^c$ are independently hydrogen, alkyl, hydroxy, alkoxy, aryloxy, aralkoxy, alkoxycarbonyl, cyano, or —$CO_2R^w$, wherein
$R^w$ is alkyl, cycloalkyl, phenyl, benzyl,

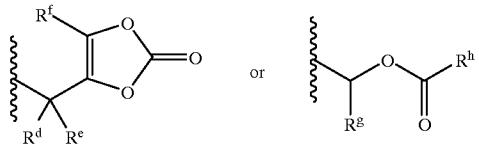

where $R^d$ and $R^e$ are independently hydrogen, $C_{1-6}$ alkyl, $C_{2-6}$ alkenyl or phenyl, $R^f$ is hydrogen, $C_{1-6}$ alkyl, $C_{2-6}$ alkenyl or phenyl, $R^g$ is hydrogen, $C_{1-6}$ alkyl, $C_{2-6}$ alkenyl or phenyl, and $R^h$ is aralkyl or $C_{1-6}$ alkyl;
n is zero to 8; and
m is zero to 6.

2. A thromboresistant surface according to claim 1, wherein
$R^3$ is hydrogen, $C_{1-4}$ alkyl, $C_{3-7}$ cycloalkyl or $CF_3$;
m is from zero to 4; and
n is from zero to 4.

3. A thromboresistant surface according to claim 2, wherein $R^3$ is $C_{1-4}$ alkyl.

4. A thromboresistant surface according to claim 2, wherein $R^4$ is hydrogen or halogen.

5. A thromboresistant surface according to claim 4, wherein W is H or $R^1$.

6. A thromboresistant surface according to claim 5, wherein
$R^1$ is
$R^2$,
$R^2(CH_2)_tC(R^{12})_2$, wherein t is 0–3 and each $R^{12}$ can be the same or different,
$R^2C(R^{12})_2(CH_2)_t$, wherein t is 0–3, each $R^{12}$ can be the same or different and wherein $(R^{12})_2$ can also form a 3- to 7-membered cycloalkyl ring with the C to which they are attached,
$R^2CH_2C(R^{12})_2(CH_2)_q$, wherein q is 0–2, and each $R^{12}$ is the same or different, and wherein $(R^{12})_2$, together with the C to which they are attached, can also form a 3- to 7-membered cycloalkyl ring, ($R^2$)CH(CH$_2$)$_r$, wherein r is 0–4, $R^2$ can be the same or different and wherein ($R^2$)$_2$ can also form, together with the C to which they are attached, a C$_{3-7}$ cycloalkyl, C$_{7-12}$ bicycloalkyl, C$_{10-16}$ tricycloalkyl or 5- to 7-membered saturated or unsaturated mono or bicyclic heterocycle having from one to three heteroatoms selected from N, O or S, $R^2$CF$_2$C($R^{12}$)$_2$(CH$_2$)$_q$, wherein q is 0–2, and each $R^{12}$ is the same or different, and wherein ($R^{12}$)$_2$, together with the C to which they are attached, can also form a 3- to 7-membered cycloalkyl ring, or $R^2$ O(CH$_2$)$_p$, wherein p is 2–4;

$R^2$ is
phenyl or naphthyl, each of which is optionally substituted with one or more of C$_{1-4}$ alkyl, C$_{1-4}$ alkoxy, halogen, hydroxy CF$_3$, OCF$_3$ or SO$_2$NH$_2$, a 5- to 7-membered monocyclic or 9- to 10-membered bicyclic, saturated or unsaturated, ring having from zero to 4 heteroatoms selected from N, O and S, and wherein said ring is optionally substituted with halogen or hydroxy, C$_{1-7}$ alkyl optionally substituted with one or more of hydroxy, COOH, C$_{3-7}$ cycloalkyl, CF$_3$, N(CH$_3$)$_2$, —C$_{1-3}$ alkaryl or heterocycle, CF$_3$, or C$_{3-7}$ cycloalkyl, optionally substituted with aryl; and $R^{12}$ is
hydrogen, or
C$_{1-4}$ alkyl, optionally substituted with one or more of hydroxy, COOH, amino, aryl or heterocycle.

7. A thromboresistant surface according to claim 6, wherein $R^3$ is hydrogen, CH$_3$ or CH$_2$CH$_3$;

$R^4$ is hydrogen or chloro; and

W is PhCH$_2$CH$_2$, (CH$_3$)$_3$C, HOOCCH$_2$, CF$_3$CH$_2$, (CH$_3$)$_2$N(CH$_2$)$_2$, PhCH$_2$O(CH$_2$)$_2$, PhCH(CH$_3$), PhCH$_2$CH(COOH), CH$_3$(CH$_2$)$_5$, PhCH$_2$, H, CH$_3$(CH$_2$)$_4$, CH$_3$CH$_2$CH(CH$_3$)CH$_2$, (Ph)$_2$CHCH$_2$, PhCH$_2$CH(CH$_3$), PhCH(CH$_3$)CH$_2$, (CH$_3$)$_2$CH, PhCH(OH)CH$_2$, PhC(CH$_3$)$_2$CH$_2$, (Ph)$_2$CHCH$_2$, or W is

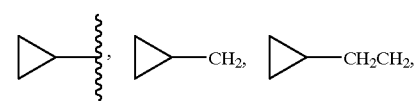

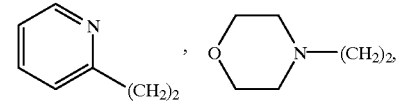

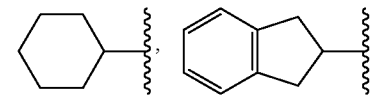

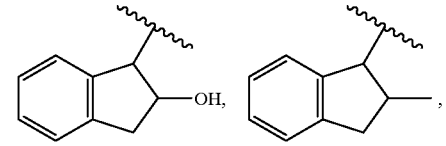

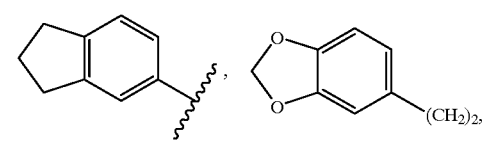

-continued

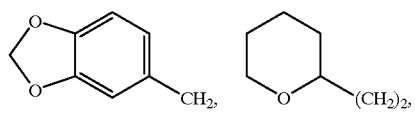

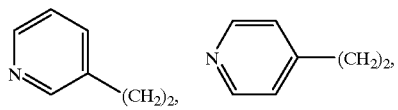

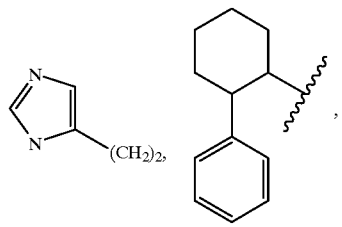

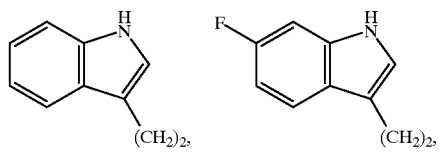

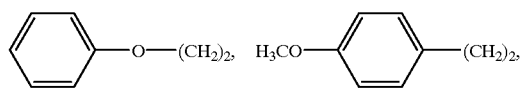

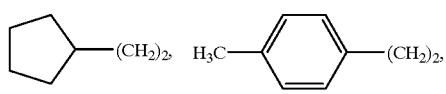

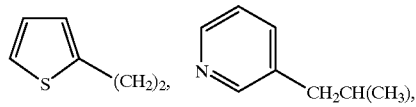

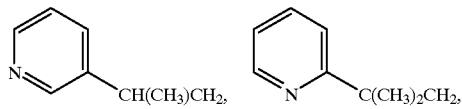

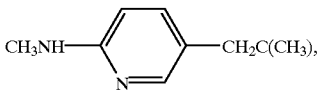

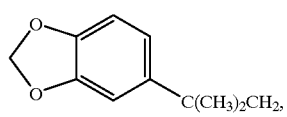

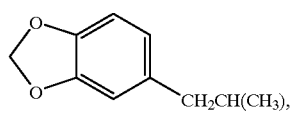

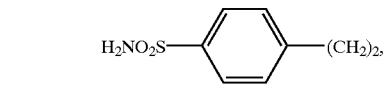

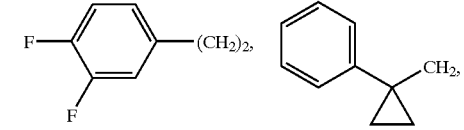

-continued

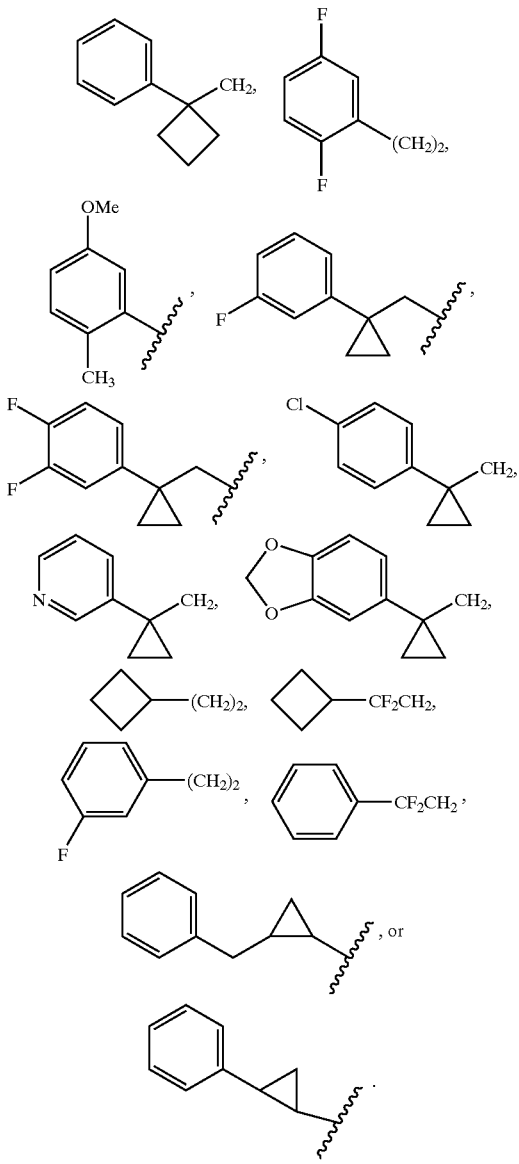

8. A thromboresistant surface according to claim 1, wherein $R^5$ is hydrogen.

9. A thromboresistant surface according to claim 1, wherein X is $NR^{11}$ or —CH=N— where $R^{11}$ is hydrogen or $C_{1-6}$ alkyl, optionally substituted by one to three of amino, monoalkylamino, dialkylamino, alkoxy, hydroxy, alkoxycarbonyl, aryloxycarbonyl, aralkoxycarbonyl, carboalkoxy, phenyl, cyano, trifluoromethyl, acetylamino, pyridyl, thiophenyl, furyl, pyrrolyl or imidazolyl.

10. A thromboresistant surface according to claim 1, wherein X is oxygen.

11. A thromboresistant surface according to claim 1, wherein $R^6$ is hydrogen or $C_{1-6}$ alkyl.

12. A thromboresistant surface according to claim 1, wherein $R^7$, $R^8$, $R^9$ and $R^{10}$ are independently one of hydrogen, $C_{1-6}$ alkyl, $C_{6-10}$ ary($C_{1-6}$)alkyl, $C_{6-10}$ aryl, $C_{2-10}$ hydroxyalkyl or $C_{2-7}$ carboxyalkyl.

13. A thromboresistant surface according to claim 12, wherein $R^7$, $R^8$, $R^9$ and $R^{10}$ are independently one of hydrogen, methyl, ethyl, propyl, n-butyl, benzyl, phenylethyl, 2-hydroxyethyl, 3-hydroxypropyl, 4-hydroxybutyl, 2-carboxymethyl, 3-carboxyethyl or 4-carboxypropyl, or wherein either $R^7$ and $R^8$ or $R^9$ and $R^{10}$ form a 3- to 7-membered carbocyclic ring with the C to which they are attached.

14. A thromboresistant surface according to claim 1, wherein $R^a$, $R^b$ and $R^c$ are independently one of hydrogen, $C_{1-6}$ alkyl, $C_{1-6}$ alkoxy, cyano, or —$CO_2R^w$ where $R^w$, in each instance, is $C_{1-4}$ alkyl, $C_{4-7}$ cycloalkyl or benzyloxycarbonyl.

15. A thromboresistant surface according to claim 14, wherein $R^a$, $R^b$ and $R^c$ are independently one of hydrogen, methyl, ethyl, propyl, n-butyl, hydroxy, methoxy, ethoxy, cyano, —$CO_2CH_3$, —$CO_2CH_2CH_3$ or —$CO_2CH_2CH_2CH_3$.

16. A thromboresistant surface according to claim 15, wherein $R^a$, $R^b$ and $R^c$ are each hydrogen.

17. A thromboresistant surface according to claim 14, wherein $R^a$, $R^b$ and $R^c$ are independently one of

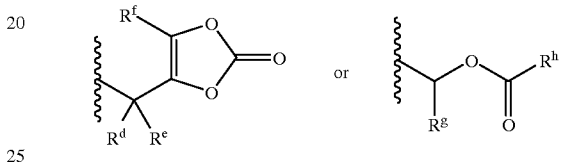

where $R^d$–$R^h$ are defined as in claim 1.

18. A thromboresistant surface according to claim 17, wherein
$R^d$, $R^e$ and $R^g$ are each hydrogen;
$R^f$ is methyl; and
$R^h$ is benzyl or tert-butyl.

19. A thromboresistant surface according to claim 1, wherein said compound is of Formula II, III or IV:

II

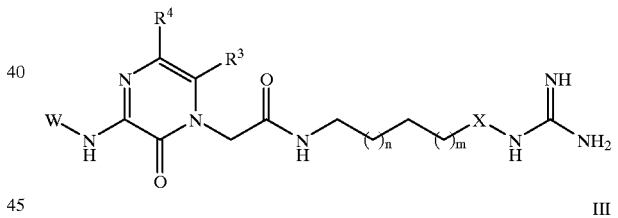

III

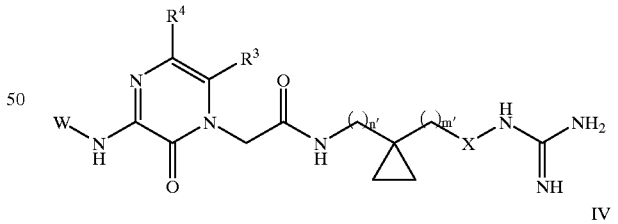

IV

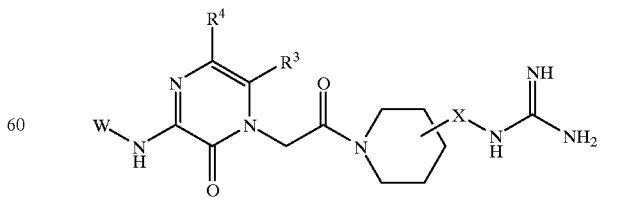

or a hydrate or pharmaceutically acceptable salt thereof, wherein n' and m' are each independently 0–3, and $R^3$, $R^4$, W, X, n and m are as defined in claim 1.

20. A thromboresistant surface according to claim 19, wherein
W is PhCH$_2$CH$_2$, (CH$_3$)$_3$C, HOOCCH$_2$, CF$_3$CH$_2$, (CH$_3$)$_2$(CH$_2$)$_2$, PhCH$_2$O(CH$_2$)$_2$, PhCH(CH$_3$), PhCH$_2$CH(COOH), CH$_3$(CH$_2$)$_5$, PhCH$_2$, H, CH$_3$(CH$_2$)$_4$, CH$_3$CH$_2$CH(CH$_3$)CH$_2$, (Ph)$_2$CHCH$_2$, PhCH$_2$CH(CH$_3$), PhCH(CH$_3$)CH$_2$, (CH$_3$)$_2$CH, PhCH(OH)CH$_2$, PhC(CH$_3$)$_2$CH$_2$, (Ph)$_2$CHCH$_2$, or W is
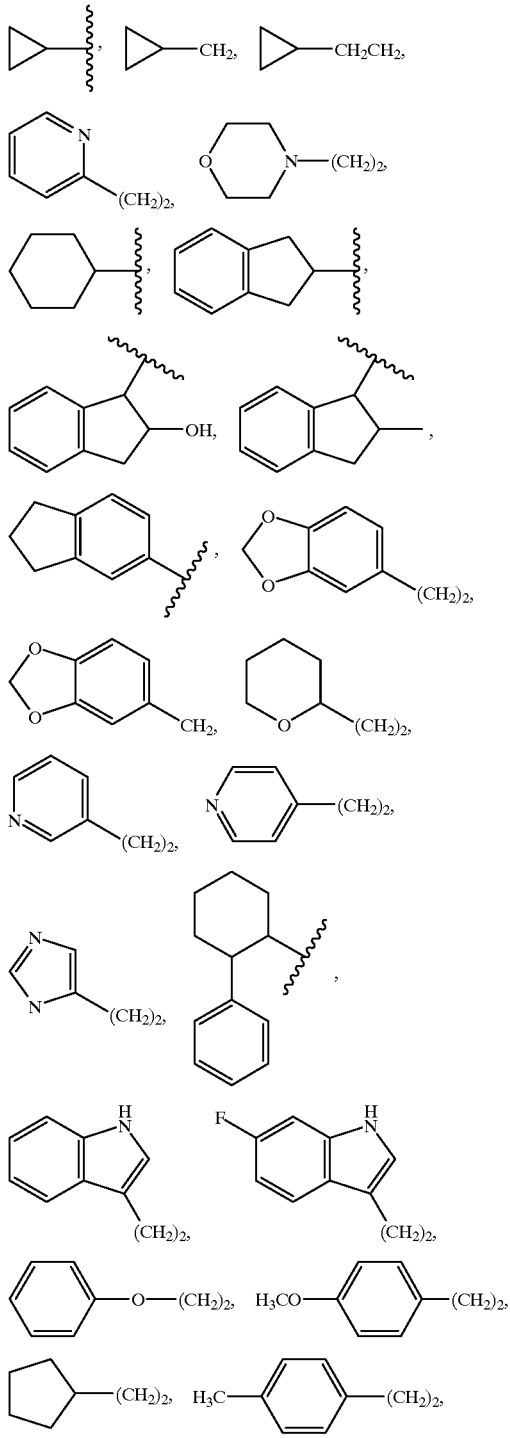
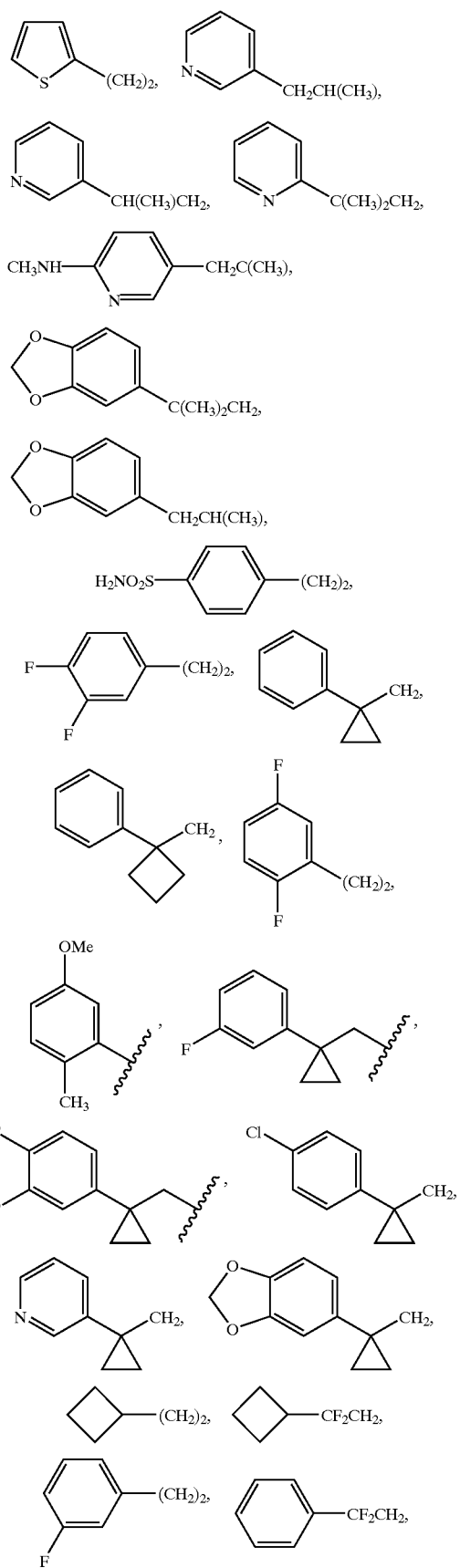

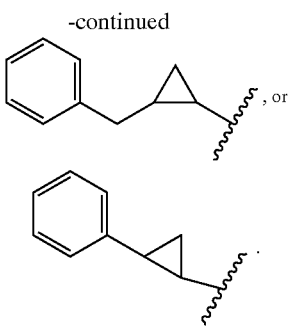

21. A thromboresistant surface according to claim 1, wherein said compound is one of 1-{N-[2-(amidinoaminooxy)ethyl]amino}carbonylmethyl-6-methyl-3-(phenethylamino)-pyrazinone, 1-{N-[2-(amidinoaminooxy)ethyl]amino}carbonylmethyl-6-methyl-3-(2,2-diphenylethylamino)-pyrazinone, 1-{N-[2-(amidinoaminooxy)ethyl]amino}carbonylmethyl-6-methyl-3-(4-methylphenethylamino)-pyrazinone, 1-{N-[2-(amidinoaminooxy)ethyl]amino}carbonylmethyl-6-methyl-3-(4-methoxyphenethylamino)-pyrazinone, 1-{N-[2-(amidinoaminooxy)ethyl]amino}carbonylmethyl-6-methyl-3-(1-phenylcyclobutyl)methylamino-pyrazinone, 1-{N-[2-(amidinoaminooxy)ethyl]amino}carbonylmethyl-6-methyl-3-[2-(1-naphthalene)ethyl]amino-pyrazinone, 1-{N-[2-(amidinoaminooxy)ethyl]amino}carbonylmethyl-6-methyl-3-(2-phenyl-1-butylamino)-pyrazinone, 1-{N-[2-(amidinoaminooxy)ethyl]amino}carbonylmethyl-6-methyl-3-(2-[3,4-methylenedioxyphenyl]ethylamino)-pyrazinone, 1-{N-[2-(amidinoaminooxy)ethyl]amino}carbonylmethyl-6-methyl-3-(2-[2-pyridyl]ethylamino)-pyrazinone, 1-{N-[2-(amidinoaminooxy)ethyl]amino}carbonylmethyl-6-methyl-3-(2-[2-methylphenyl]ethylamino)-pyrazinone, 1-{N-[2-(amidinoaminooxy)ethyl]amino}carbonylmethyl-6-methyl-3-(2-[3-methylphenyl]ethylamino)-pyrazinone, 1-{N-[2-(amidinoaminooxy)ethyl]amino}carbonylmethyl-6-methyl-3-(2-[2-trifluoromethylphenyl]ethylamino)-pyrazinone, 1-{N-[2-(amidinoaminooxy)ethyl]amino}carbonylmethyl-6-methyl-3-(2-[3-trifluoromethylphenyl]ethylamino)-pyrazinone, 1-{N-[2-(amidinoaminooxy)ethyl]amino}carbonylmethyl-6-methyl-3-(2-[4-trifluoromethylphenyl]ethylamino)-pyrazinone, 1-{N-[2-(amidinoaminooxy)ethyl]amino}carbonylmethyl-6-methyl-3-(2-[3,5-dimethylphenyl]ethylamino)-pyrazinone, 1-{N-[2-(amidinoaminooxy)ethyl]amino}carbonylmethyl-6-methyl-3-(2-indanylamino)-pyrazinone, 1-{N-[2-(amidinoaminooxy)ethyl]amino}carbonylmethyl-6-methyl-3-(2-[3,4-difluorophenyl]ethylamino)-pyrazinone, 1-{N-[2-(amidinoaminooxy)ethyl]amino}carbonylmethyl-6-methyl-3-(2-[5-indanyl]ethylamino)-pyrazinone, 1-{N-[2-(amidinoaminooxy)ethyl]amino}carbonylmethyl-6-methyl-3-(2-fluorophenethylamino)-pyrazinone, 1-{N-[2-(amidinoaminooxy)ethyl]amino}carbonylmethyl-6-methyl-3-(3,4-dimethoxyphenethylamino)-pyrazinone, 1-{N-[2-(amidinoaminooxy)ethyl]amino}carbonylmethyl-6-methyl-3-(4-fluorophenethylamino)-pyrazinone, 1-{N-[2-(amidinoaminooxy)ethyl]amino}carbonylmethyl-6-methyl-3-(4-ethylphenethylamino)-pyrazinone, 1-{N-[2-(amidinoaminooxy)ethyl]amino}carbonylmethyl-6-methyl-3-(2-phenylpropylamino)-pyrazinone, 1-{N-[2-(amidinoaminooxy)ethyl]amino}carbonylmethyl-6-methyl-3-(3,4-dimethylphenethylamino)-pyrazinone, 1-{N-[2-(amidinoaminooxy)ethyl]amino}carbonylmethyl-6-methyl-3-(2-naphthaleneethylamino)-pyrazinone, 1-{N-[2-(amidinoaminooxy)ethyl]amino}carbonylmethyl-6-methyl-3-(2,2-diphenylpropylamino)-pyrazinone, 1-{N-[2-(amidinoaminooxy)ethyl]amino}carbonylmethyl-6-methyl-3-(2-(3-indolyl)-ethylamino-pyrazinone, 1-{N-[2-(amidinoaminooxy)ethyl]amino}carbonylmethyl-6-methyl-3-(2-[1-(4-methylnaphthalene)]ethylamino)-pyrazinone, 1-{N-[2-(amidinoaminooxy)ethyl]amino}carbonylmethyl-6-methyl-3-(2-[2,4-difluorophenyl]ethylamino)-pyrazinone.

1-{N-[2-(amidino-N'-methylaminooxy)ethyl]amino}carbonylmethyl-6-methyl-3-(2-[4-methylphenyl]ethylamino)-pyrazinone, 1-{N-[2-(amidinoaminooxy)ethyl]amino}carbonylmethyl-5-chloro-6-methyl-3-(phenethylamino)-pyrazinone, 1-{N-[2-(amidinoaminooxy)ethyl]amino}carbonylmethyl-5-chloro-6-methyl-3-(2,2-diphenylethylamino)-pyrazinone, 1-{N-[2-(amidinohydrazino)ethyl]amino}carbonylmethyl-6-methyl-3-(phenethyl)-pyrazinone, 1-{N-[2-(amidinohydrazino)ethyl]amino}carbonylmethyl-6-methyl-3-(1-methyl-2-phenylethyl)-pyrazinone, 1-{N-[2-(amidinohydrazino)ethyl]amino}carbonylmethyl-6-ethyl-3-(phenethyl)-pyrazinone, 1-{N-[2-(amidinohydrazino)ethyl]amino}carbonylmethyl-6-methyl-3-(4-methylphenylethyl)-pyrazinone, 1-{N-[2-(amidinoaminooxy)ethyl]amino}carbonylmethyl-6-methyl-3-(1-methyl-2-(4-methylamino-3-pyridyl)ethyl-pyrazinone, 1-{N-[2-(amidinoaminooxy)ethyl]amino}carbonylmethyl-6-methyl-3-(1-methyl-2-(3-pyridyl)ethyl-pyrazinone, 1-{N-[2-(amidinoaminooxy)ethyl]amino}carbonylmethyl-6-methyl-3-(2-cyclopropyl-2-(3,4-dimethoxyphenyl)ethyl)-pyrazinone, 1-{N-[2-(amidinoaminooxy)ethyl]amino}carbonylmethyl-6-methyl-3-(2-cyclobutylethyl)-pyrazinone, 1-{N-[2-(amidinoaminooxy)ethyl]amino}carbonylmethyl-6-methyl-3-(2-cyclobutyl-2,2-difluoroethyl)-pyrazinone, 1-{N-[2-(amidinoaminooxy)ethyl]amino}carbonylmethyl-6-methyl-3-(2-(3-fluorophenyl)ethyl)-pyrazinone, 1-{N-[2-(amidinoaminooxy)ethyl]amino}carbonylmethyl-6-methyl-3-(2,2-difluoro-2-phenylethyl)-pyrazinone, 1-{N-[2-(amidinoaminooxy)ethyl]amino}carbonylmethyl-6-methyl-3-(2-phenylcyclopropyl)-pyrazinone, 1-{N-[2-(amidinoaminooxy)ethyl]amino}carbonylmethyl-6-methyl-3-(2-(4-chlorophenyl)-2-cyclopropylethyl)-pyrazinone, 1-{N-[2-(amidinoaminooxy)ethyl]amino}carbonylmethyl-6-methyl-3-(2-cyclopropyl-2-(3-pyridyl)ethyl)-pyrazinone, 1-{N-[2-(amidinoaminooxy)ethyl]amino}carbonylmethyl-6-methyl-3-(2-benzylcylopropyl)-pyrazinone, 1-{N-[2-(amidinoaminooxy)ethyl]amino}carbonylmethyl-6-methyl-3-(2-cyclopropyl-2-(3-fluorophenyl)ethyl)-pyrazinone, 1-{N-[2-(amidinoaminooxy)ethyl]amino}carbonylmethyl-6-methyl-3-(2-cyclopropyl-2-(3,4-difluorophenyl)ethyl)-pyrazinone, or 1-{N-[2-(amidinoaminooxy)ethyl]amino}carbonylmethyl-6-methyl-3-(2,2-difluoro-2-phenylethylamino)-pyrazinone, and pharmaceutically acceptable salts thereof.

22. A thromboresistant surface according to claim 1, wherein said surface is a stent.

23. A thromboresistant medical device selected form the group consisting of a stent, a catheter, a blood dialysis machine, a syringe, and a tube, comprising a compound of Formula I:

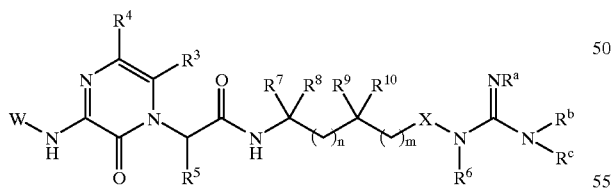

I or a hydrate or pharmaceutically acceptable salt thereof; wherein:

W is hydrogen, $R^1$, $R^1OCO$, $R^1CO$, $R^1(CH_2)_sNHCO$, or $(R^1)_2CH(CH_2)_sNHCO$, wherein s is 0–4;

$R^1$ is $R^2$, $R^2$, $R^2(CH_2)_tC(R^{12})_2$, wherein t is 0–3 and each $R^{12}$ is the same or different, $(R^2)(OR^{12})CH(CH_2)_p$, wherein p is 1–4, $(R^2)_2(OR^{12})C(CH_2)_p$, wherein p is 1–4, $R^2C(R^{12})_2(CH_2)_t$, wherein t is 0–3, and each $R^{12}$ is the same or different, and wherein $(R^{12})_2$, together with the C to which they are attached, can also form a 3- to 7-membered cycloalkyl ring, $R^2CH_2C(R^{12})_2(CH_2)_q$, wherein q is 0–2, and each $R^{12}$ is the same or different, and wherein $(R^{12})_2$, together with the C to which they are attached, can also form a 3- to 7-membered cycloalkyl ring, $R^2CF_2C(R^{12})_2(CH_2)_q$, wherein q is 0–2, and each $R^{12}$ is the same or different, and wherein $(R^{12})_2$, together with the C to which they are attached, can also for a 3- to 7-membered cycloalkyl ring, $(R^2)_2CH(CH_2)_r$, wherein r is 0–4, and each $R^2$ is the same or different, and wherein $(R^2)_2$, together with the C to which they are attached, can also form a $C_{3-7}$ cycloalkyl, $C_{7-12}$ bicyclic alkyl, $C_{10-16}$ tricyclic alkyl, or a 5- to 7-membered, saturated or unsaturated, mono- or bi-cyclic, heterocyclic ring, having from one to three heteroatoms selected from N, O, and S, $R^2O(CH_2)_p$, wherein p is 2–4;

$(R^2)_2CF(CH_2)_r$, wherein r is 0–4 and each $R^{12}$ is the same of different, and wherein $(R^{12})_2$, together with the C to which they are attached, can also form a 3- to 7-membered cycloalkyl, $C_{7-12}$ bicyclic alkyl, $C_{10-16}$ trycyclic alkyl, or a 5- to 7-membered mono- or bicyclic heterocyclic ring which can be saturated or unsaturated, and which contains from one to three heteroatoms selected from the group consisting of N, O and S,

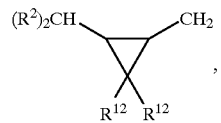

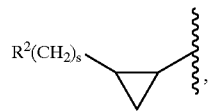

where s is 0 or 1, or $(R^2)CF_2C(R^{12})_2$;

$R^2$ is phenyl, naphthyl or biphenyl, each of which is optionally substituted with one or more of $C_{1-4}$ alkyl, $C_{1-4}$ alkoxy, halogen, hydroxy, $CF_3$, $OCF_3$, COOH, $CONH_2$, or $SO_2NH_2$, a 5- to 7-membered, saturated or unsaturated, mono- or a 9- to 10-membered bi- cyclic ring optionally having from one to four heteroatoms selected from N, O, or S, and optionally substituted with halogen or hydroxy, $C_{1-7}$ alkyl, optionally substituted with one or more of hydroxy, COOH, amino, aryl, $C_{3-7}$ cycloalkyl, $CF_3$, $N(CH_3)_2$, —$C_{1-3}$ alkylaryl or heterocycle, $CF_3$, $C_{3-7}$ cycloalkyl, optionally substituted with aryl, $C_{7-12}$ bicyclic alkyl, or $C_{10-16}$ tricyclic alkyl;

$R^3$ is hydrogen, alkyl, cycloalkyl, alkenyl, alkynyl, optionally substituted aryl, optionally substituted aralkyl, optionally substituted heteroaryl, trifluoromethyl, halogen, hydroxyalkyl, cyano, nitro, carboxamido, —CO$_2$R$^x$, —CH$_2$OR$^x$, or OR$^x$, wherein R$^x$, in each instance, is independently one of hydrogen, optionally unsaturated alkyl, or optionally unsaturated cycloalkyl;

R$^4$ is
hydrogen or halogen;

R$^{12}$ is
hydrogen,
phenyl, naphthyl or biphenyl, each of which is optionally substituted with one or more of C$_{1-4}$ alkyl, C$_{1-4}$ alkoxy, halogen, hydroxy, CF$_3$, OCF$_3$, COOH, or CONH$_2$,
a 5- to 7-membered mono- or a 9- to 10-membered bi-cyclic, saturated or unsaturated, heterocyclic ring having from one to four heteroatoms selected from N, O, or S, C$_{1-4}$ alkyl, optionally substituted with one or more of hydroxy, COOH, amino, aryl or heterocycle,
CF$_3$,
C$_{3-7}$ cycloalkyl,
C$_{7-12}$ bicyclic alkyl, or
C$_{1-16}$ tricyclic alkyl;

R$^5$ is hydrogen, C$_{1-4}$ alkyl, or C$_{2-4}$ alkenyl;

R$^6$ is hydrogen, alkyl, alkenyl, aralkyl, aryl, hydroxyalkyl, aminoalkyl, monoalkylamino(C$_{2-10}$)alkyl, dialkylamino(C$_{2-10}$)alkyl, or carboxyalkyl;

R$^7$, R$^8$, R$^9$, R$^{10}$ are independently hydrogen, alkyl, aralkyl, aryl, hydroxyalkyl, aminoalkyl, monoalkylaminoalkyl, dialkylaminoalkyl, or carboxyalkyl, or R$^7$ and R$^8$, together with the C to which they are attached, form a 3- to 8-membered cycloalkyl group, and R$^9$ and R$^{10}$ are as defined above, or R$^9$ and R$^{10}$, together with the C to which they are attached, form a 3- to 8-membered cycloalkyl group, and R$^7$ and R$^8$ are as defined above, or R$^7$ and R$^9$, together with the C to which they are attached, form a 3- to 8-membered cycloalkyl group, and R$^8$ and R$^{10}$ are as defined above; X is oxygen, —NR$^{11}$—, or —CH=N—, wherein R$^{11}$ is hydrogen, alkyl, cycloalkyl, or aryl and said alkyl, cycloalkyl and aryl are optionally substituted with amino, monoalkylamino, dialkylamino, alkoxy, hydroxy, carboxy, alkoxycarbonyl, aryloxycarbonyl, aralkoxycarbonyl, aryl, heteroaryl, acetylamino, cyano, or trifluoromethyl;

R$^a$, R$^b$ and R$^c$ are independently hydrogen, alkyl, hydroxy, alkoxy, aryloxy, aralkoxy, alkoxycarbonyl, cyano, or —CO$_2$R$^w$, wherein
R$^w$ is alkyl, cycloalkyl, phenyl, benzyl,

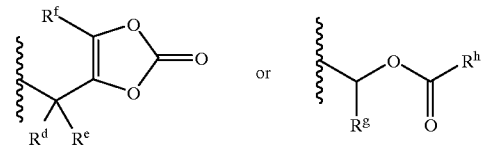

where R$^d$ and R$^e$ are independently hydrogen, C$_{1-6}$ alkyl, C$_{2-6}$ alkenyl or phenyl, R$^f$ is hydrogen, C$_{1-6}$ alkyl, C$_{2-6}$ alkenyl or phenyl, R$^g$ is hydrogen, C$_{1-6}$ alkyl, C$_{2-6}$ alkenyl or phenyl, and R$^h$ is aralkyl or C$_{1-6}$ alkyl;

n is zero to 8; and
m is zero to 6,
wherein R$^1$ comprises a radioactive atom.

24. A thromboresistant medical device according to claim 23, wherein said compound is covalently attached to or embedded within a polymer coated onto said device.

25. A thromboresistant medical device according to claim 24, wherein said polymer is selected from the group consisting of polyvinylpyrrolidone, polyhydroxypropylmethacrylamide-phenol, polyhydroxyethyl-aspartamide-phenol, polyethyleneoxide-polylysine substituted with palmitoyl residues, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

* * * * *

UNITED STATES PATENT AND TRADEMARK OFFICE
CERTIFICATE OF CORRECTION

PATENT NO.     : 6,514,978 B2                                              Page 1 of 4
DATED          : February 4, 2003
INVENTOR(S)    : Lu et al.

It is certified that error appears in the above-identified patent and that said Letters Patent is hereby corrected as shown below:

Column 5,
Line 17, please delete "–$C_{1-3}$ alkylaryl," and insert therein -- $C_{1-3}$ alkaryl, --.

Column 7,
Line 12, please delete "–$C_{1-3}$ alkylaryl," and insert therein -- $C_{1-3}$ alkaryl, --.

Column 10,
Line 35, please delete "$R^w$" and insert therein -- $R^f$ --.

Column 11,
Line 18, please delete "NH is attached to" and insert therein -- N is attached to --.

Column 15,
Line 11, please delete "diethylenetrimine-N,N,N',N",N"-pentaacetic acid"
and insert therein -- diethylenetriamine-N,N,N',N",N"-pentaacetic acid --.

Columns 17 & 18,
Scheme 2, please delete "$R_3CHO$," and insert therein -- $R^3CHO$, --.

Column 35,
Lines 61-64, please delete "1-{N-[2-(N',N"-bis(tertbutoxycarbonyl)amidinoaminooxy) ethyl]amino}carbonylmethyl-5-chlor o-6-methyl-3-(phenethylamino)-pyrazinone," and insert therein -- 1-{N-[2-(N',N"-bis(tert-butoxycarbonyl) amidinoaminooxy)ethyl] amino}carbonylmethyl-5-chloro-6-methyl-3-(phenethylamino)-pyrazinone, --.

Column 44,
Line 5, please delete

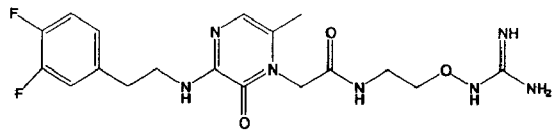

and insert therein

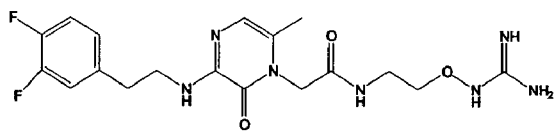

UNITED STATES PATENT AND TRADEMARK OFFICE
CERTIFICATE OF CORRECTION

PATENT NO.   : 6,514,978 B2
DATED        : February 4, 2003
INVENTOR(S)  : Lu et al.

It is certified that error appears in the above-identified patent and that said Letters Patent is hereby corrected as shown below:

Column 44 cont'd,
Line 30, please delete and insert therein

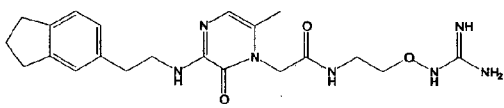

Line 50, please delete

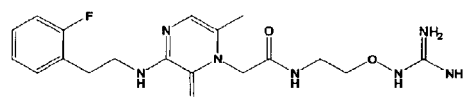

and insert therein

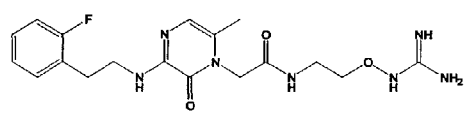

Column 48,
Line 50, please delete

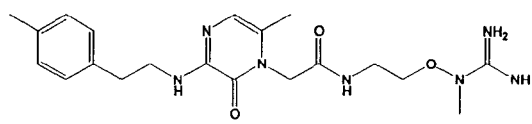

and insert therein

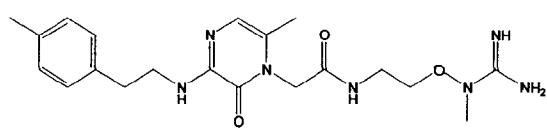

UNITED STATES PATENT AND TRADEMARK OFFICE
CERTIFICATE OF CORRECTION

PATENT NO. : 6,514,978 B2
DATED : February 4, 2003
INVENTOR(S) : Lu et al.

It is certified that error appears in the above-identified patent and that said Letters Patent is hereby corrected as shown below:

Column 52,
Line 37, please delete "$R^1(CH_2)_5NHCO$," and insert therein -- $R^1(CH_2)_8NHCO$, --.
Line 41, please delete "each $R_{12}$" and insert therein -- each $R^{12}$ --.
Line 55, please delete "can also for" and insert therein -- can also form --.
Line 57, please delete "each $R_2$" and insert therein -- each $R^2$ --.
Line 58, please delete "wherein $(R_2)_2$," and insert therein -- wherein $(R^2)_2$,--.
Line 67, please delete "same of different" and insert therein -- same or different --.

Column 53,
Line 3, please delete "trycyclic" and insert therein -- tricyclic --.
Line 47, please delete "–$CO_9R^x$," and insert therein -- –$CO_2R^x$, --.

Column 55,
Line 16, please delete "hydroxy" and insert therein -- hydroxy, --.
Line 24, please delete "–$C_{1-3}$ alkaryl" and insert therein -- $C_{1-3}$ alkaryl --.

Column 57,
Line 63, please delete "$C_{6-10}$ary($C_{1-6}$)alkyl," and insert therein -- $C_{6-10}$ar($C_{1-6}$)alkyl, --.

Column 59,
Lines 5-6, please delete "$(CH_3)_2(CH_2)_2$," and insert therein -- $(CH_3)_2N(CH_2)_2$, --.

Column 62,
Lines 36-38, please delete "1-{N-[2-(amidinoaminooxy)ethyl}amino}carbonylmethyl-6-methyl-3-(2-[2,4-difluorophenyl]ethylamino)-pyrazinone." and insert therein -- 1-{N-[2-(amidinoaminooxy) ethyl]amino}carbonylmethyl-6-methyl-3-(2-[2,4-difluorophenyl]ethylamino)-pyrazinone, --.

Column 63,
Line 42, please delete "form" and insert therein -- from --.
Line 63, please delete "$R^2$,".

Column 64,
Line 12, please delete "also for" and insert therein -- also form --.
Line 27, please delete "trycyclic" and insert therein -- tricyclic --.
Line 60, please delete "–$C_{1-3}$ alkylaryl," and insert therein -- $C_{1-3}$ alkylaryl, --.
Line 62, please insert a carriage return after "aryl," so that "$C_{7-12}$ bicyclic alkyl, or" appears as one continuous line.

UNITED STATES PATENT AND TRADEMARK OFFICE
CERTIFICATE OF CORRECTION

PATENT NO. : 6,514,978 B2
DATED : February 4, 2003
INVENTOR(S) : Lu et al.

It is certified that error appears in the above-identified patent and that said Letters Patent is hereby corrected as shown below:

Column 65,
Line 18, please insert a carriage return after "N, O, orS," so that "$C_{1-4}$Alkyl" and the terms thereafter appear on the next line below "N, O, or S,"
Line 25, please delete "$C_{1-16}$ tricyclic alkyl;" and insert therein -- $C_{10-16}$ tricyclic alkyl; --.
Line 42, please insert a carriage return after "as defined above;" so that "X is oxygen," and the terms thereafter appear on the next line below "as defined above;"

Column 66,
Line 20, please delete "where $R^d$ and $R^{c}$" and insert therein -- where $R^d$ and $R^e$ --.

Signed and Sealed this

Twenty-ninth Day of July, 2003

JAMES E. ROGAN
*Director of the United States Patent and Trademark Office*